United States Patent
Nakaie et al.

(10) Patent No.: US 10,147,885 B2
(45) Date of Patent: Dec. 4, 2018

(54) ANILINE DERIVATIVES AND USES THEREOF

(71) Applicant: NISSAN CHEMICAL INDUSTRIES, LTD., Tokyo (JP)

(72) Inventors: Naoki Nakaie, Funabashi (JP); Taichi Nakazawa, Funabashi (JP); Seiya Terai, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/552,864

(22) PCT Filed: Feb. 17, 2016

(86) PCT No.: PCT/JP2016/054519
§ 371 (c)(1),
(2) Date: Aug. 23, 2017

(87) PCT Pub. No.: WO2016/136544
PCT Pub. Date: Sep. 1, 2016

(65) Prior Publication Data
US 2018/0240974 A1    Aug. 23, 2018

(30) Foreign Application Priority Data
Feb. 24, 2015 (JP) .................. 2015-033810

(51) Int. Cl.
| | |
|---|---|
| *H01L 51/00* | (2006.01) |
| *C07C 211/61* | (2006.01) |
| *C09D 5/24* | (2006.01) |
| *C07C 211/58* | (2006.01) |
| *C07D 209/88* | (2006.01) |
| *H01L 51/56* | (2006.01) |
| *H01L 51/50* | (2006.01) |

(52) U.S. Cl.
CPC .......... *H01L 51/006* (2013.01); *C07C 211/58* (2013.01); *C07C 211/61* (2013.01); *C07D 209/88* (2013.01); *C09D 5/24* (2013.01); *H01L 51/0061* (2013.01); *C07C 2603/26* (2017.05); *C07C 2603/97* (2017.05); *H01L 51/0003* (2013.01); *H01L 51/0056* (2013.01); *H01L 51/0058* (2013.01); *H01L 51/0072* (2013.01); *H01L 51/5088* (2013.01); *H01L 51/56* (2013.01)

(58) Field of Classification Search
CPC ............. H01L 51/006; H01L 51/0061; H01L 51/0072; H01L 51/0056; H01L 51/0058; H01L 51/0003; H01L 51/5088; H01L 51/56; C07D 209/88; C07C 211/58; C07C 211/61; C07C 2603/97; C07C 2603/26; C09D 5/24
See application file for complete search history.

(56) References Cited

U.S. PATENT DOCUMENTS

| | | | |
|---|---|---|---|
| 2005/0208334 A1* | 9/2005 | Lee | ................. C09B 57/008 428/690 |
| 2007/0285004 A1* | 12/2007 | Miki | ................. C07C 211/54 313/504 |
| 2008/0029742 A1 | 2/2008 | Yoshimoto et al. | |

(Continued)

FOREIGN PATENT DOCUMENTS

| | | |
|---|---|---|
| EP | 2 950 361 A1 | 12/2015 |
| JP | 2005-276832 A | 10/2005 |
| JP | 2010-97964 A | 4/2010 |
| JP | 2012-140434 A | 7/2012 |
| WO | WO 2006/025342 A1 | 3/2006 |

(Continued)

OTHER PUBLICATIONS

International Search Report for PCT/JP2016/054519 (PCT/ISA/210) dated May 17, 2016.

(Continued)

*Primary Examiner* — Karen Kusumakar
(74) *Attorney, Agent, or Firm* — Birch, Stewart, Kolasch & Birch, LLP

(57) ABSTRACT

Aniline derivatives such as those represented by the formulas shown, for example, have good solubility in organic solvents, and are able to provide organic electroluminescent elements having excellent longevity when thin films containing said aniline derivatives as charge transporting substances are used for hole injection layers.

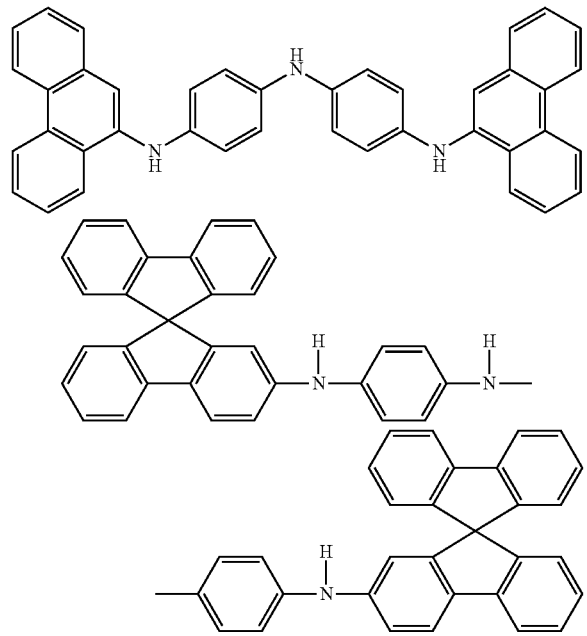

11 Claims, No Drawings

(56) References Cited

U.S. PATENT DOCUMENTS

2010/0159279 A1  6/2010  Kato et al.
2010/0230639 A1  9/2010  Yamada et al.

FOREIGN PATENT DOCUMENTS

| WO | WO 2008/032616 A1 | 3/2008 |
| WO | WO 2008/129947 A1 | 10/2008 |
| WO | WO 2010/058777 A1 | 5/2010 |
| WO | WO 2014/115865 A1 | 7/2014 |

OTHER PUBLICATIONS

Written Opinion of the International Searching Authority for PCT/JP2016/054519 (PCT/ISA/237) dated May 17, 2016.

* cited by examiner

ANILINE DERIVATIVES AND USES THEREOF

TECHNICAL FIELD

The present invention relates to aniline derivatives and their use.

BACKGROUND ART

Charge-transporting thin films consisting of organic compounds are used as light-emitting layers and charge-injecting layers in organic electroluminescent (EL) devices. In particular, a hole-injecting layer is responsible for transferring charge between an anode and a hole-transporting layer or a light-emitting layer, and thus serves an important function in achieving low-voltage driving and high brightness in organic EL devices.

Processes for forming the hole-injecting layer are broadly divided into dry processes such as vapor deposition and wet processes such as spin coating. Comparing these different processes, wet processes are better able to efficiently produce thin films having a high flatness over a large area. Hence, with the progress currently underway toward larger-area organic EL displays, there exists a desire for a hole-injecting layer that can be formed by a wet process.

In view of these circumstances, the inventors have developed charge-transporting materials which can be employed in various wet processes and which moreover give thin films that, when used as hole-injecting layers for organic EL devices, are capable of achieving excellent EL device characteristics. The inventors have also developed compounds which have a good solubility in organic solvents used in such charge-transporting materials (see, for example, Patent Documents 1 to 4).

PRIOR ART DOCUMENTS

Patent Documents

Patent Document 1: WO 2008/032616
Patent Document 2: WO 2008/129947
Patent Document 3: WO 2006/025342
Patent Document 4: WO 2010/058777

SUMMARY OF THE INVENTION

Problems to be Solved by the Invention

It is therefore an object of this invention to provide aniline derivatives which, as with the hitherto developed art disclosed in the above patent publications, exhibit good solubility in organic solvents and, when formed into a thin film and used as a hole-injecting layer, enable organic EL devices endowed with excellent longevity characteristics to be achieved.

Means for Solving the Problems

The inventors have conducted extensive investigations, as a result of which they have discovered that certain aniline derivatives have an excellent solubility in organic solvents and that thin films exhibiting high charge transportability can be obtained from varnishes prepared by dissolving such aniline derivatives in organic solvents. The inventors have also found that when such a thin film is used as a hole-injecting layer in an organic EL device, it is possible to obtain a device having a good longevity.

Accordingly, the invention provides:
1. An aniline derivative of formula (1)

[Chemical Formula 1]

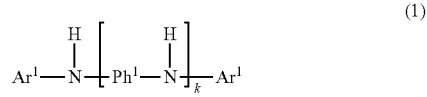

wherein $Ph^1$ is a group of formula (P1)

[Chemical Formula 2]

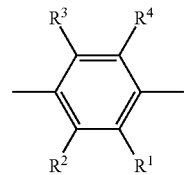

(wherein $R^1$ to $R^4$ are each independently a hydrogen atom, a halogen atom, a nitro group, a cyano group or an alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with a halogen atom); each $Ar^1$ is independently any moiety of formulas (A1) to (A34) below

[Chemical Formula 3]

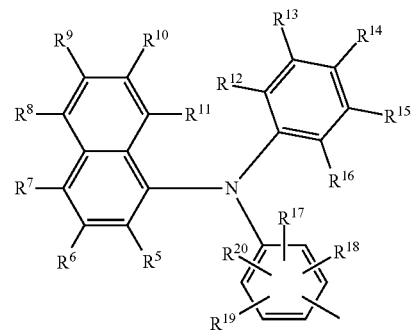

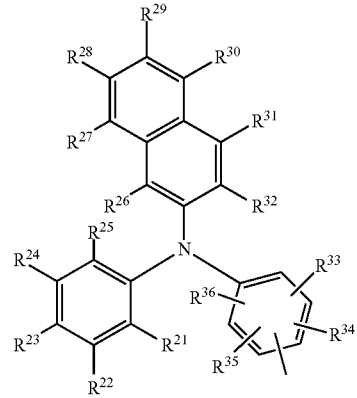

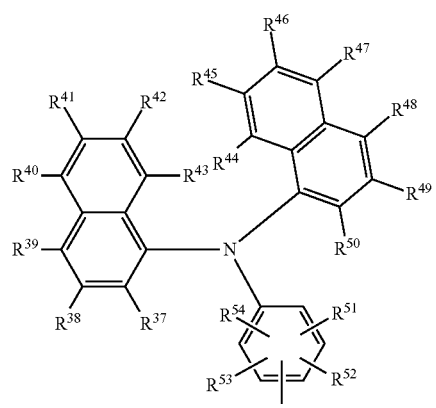
(A3)
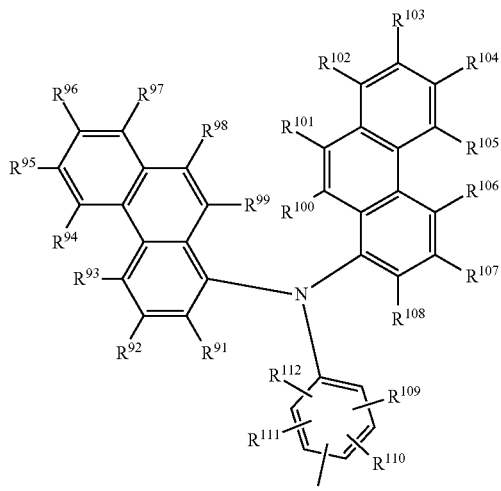
(A6)
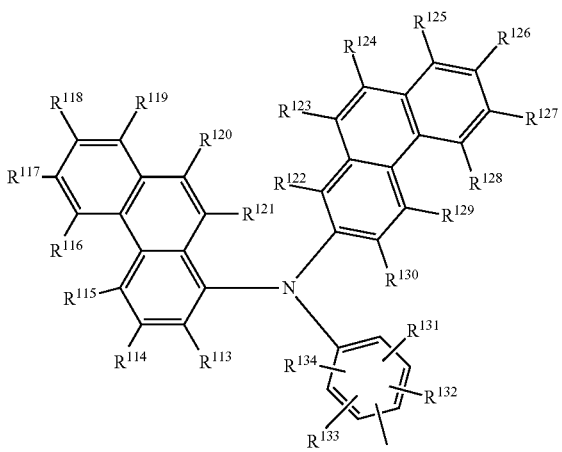
(A7)
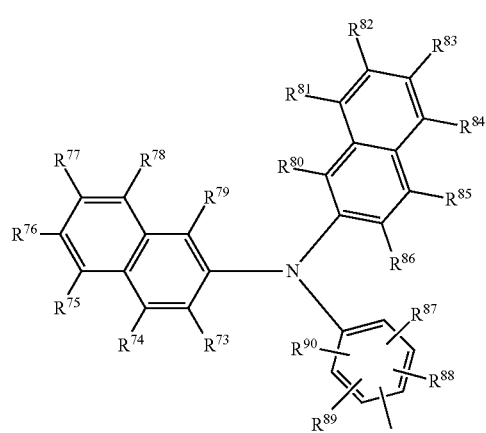
(A5)
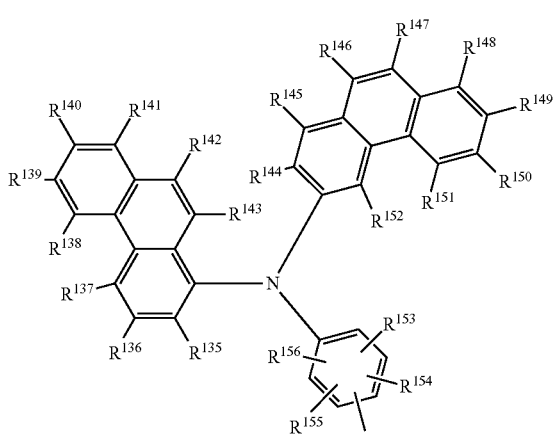
(A8)

(A9)
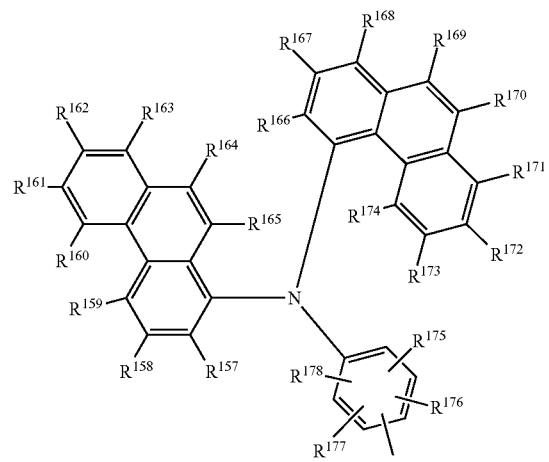
(A10)
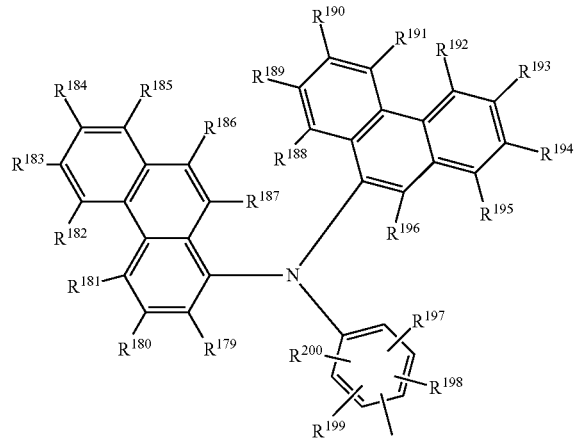
[Chemical Formula 4]
(A11)
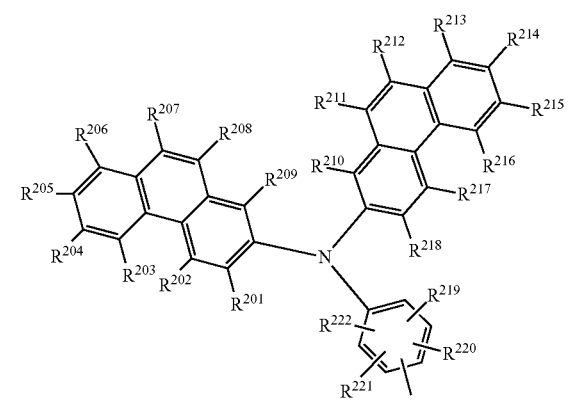
(A12)
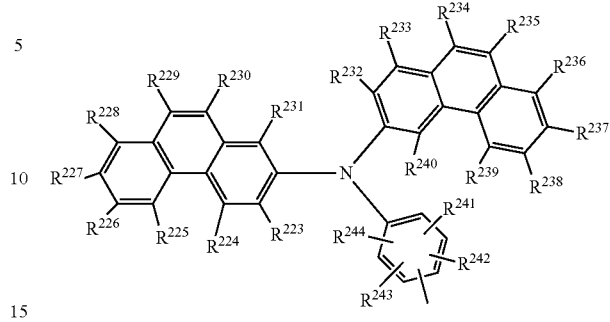
(A13)
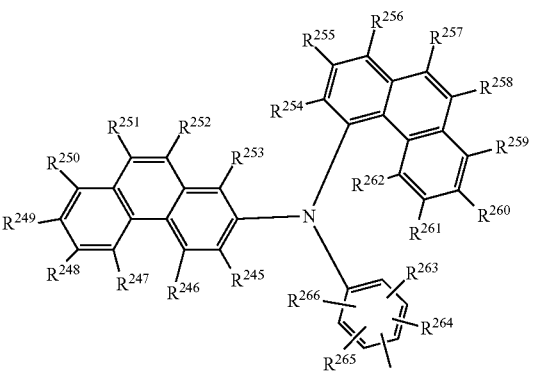
(A14)
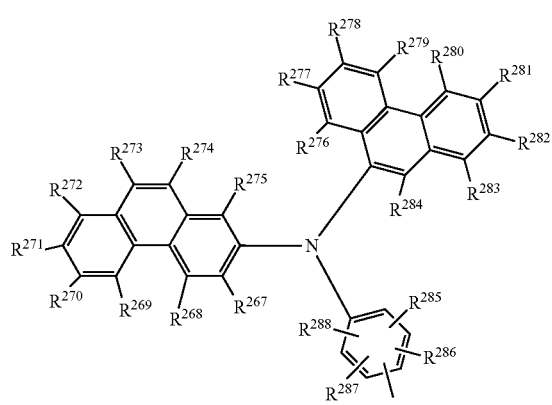
(A15)
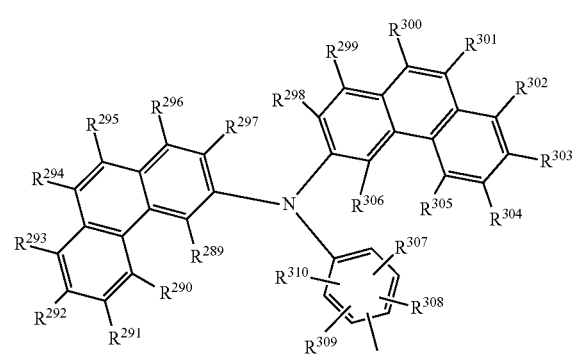

-continued
(A16)
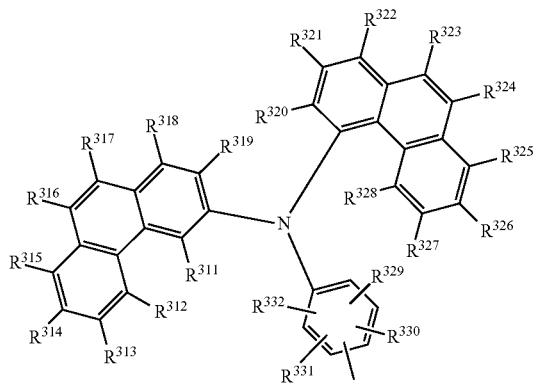
(A17)
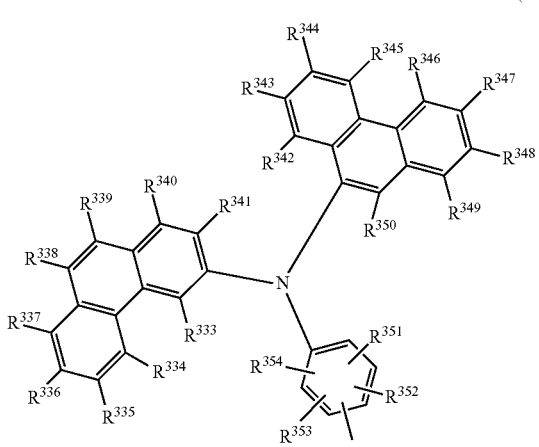
(A18)
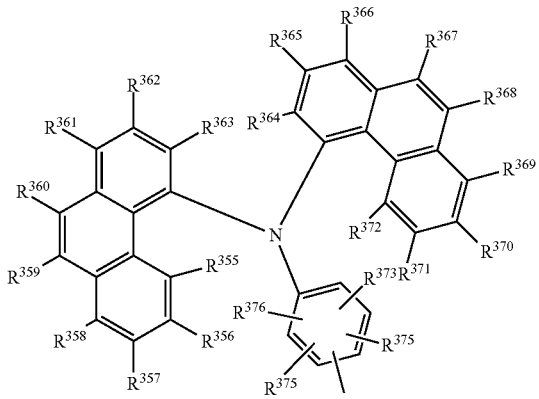
[Chemical Formula 5]
(A19)
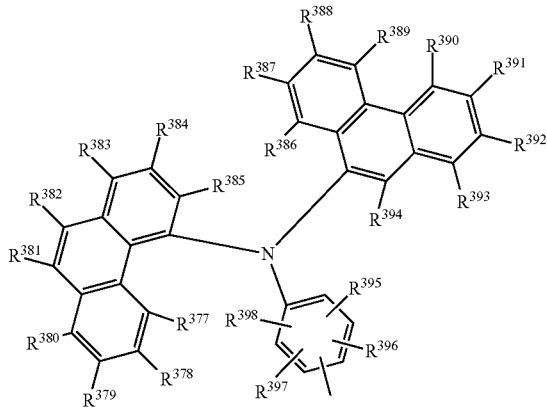
(A20)
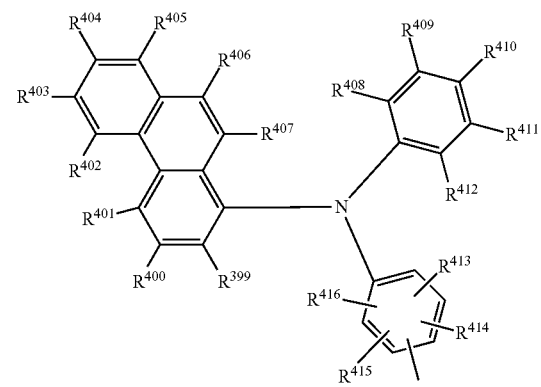
(A21)
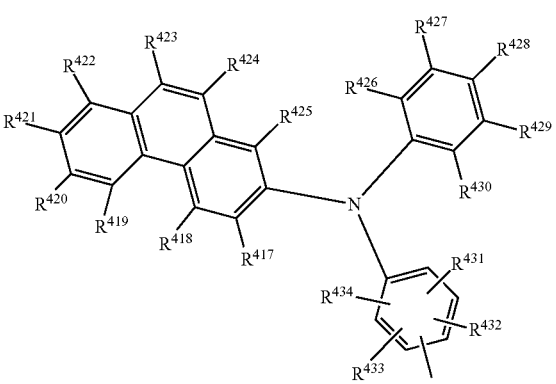
(A22)
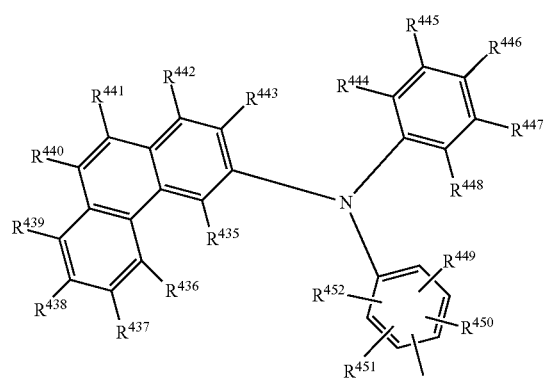

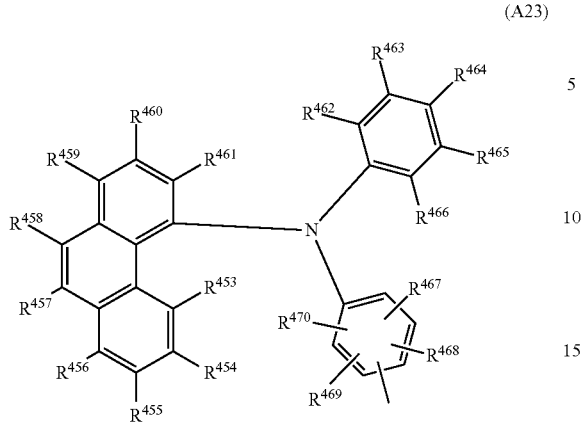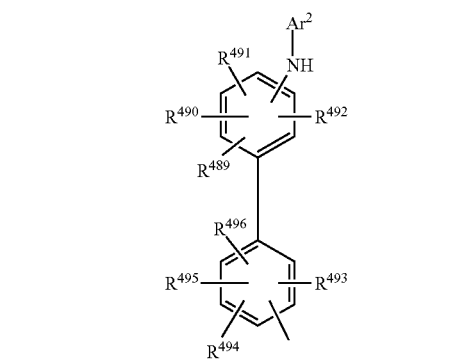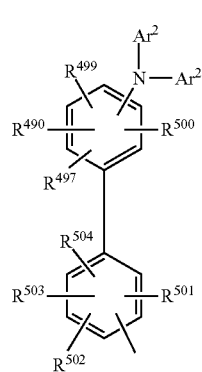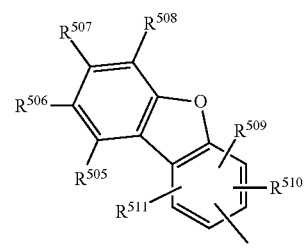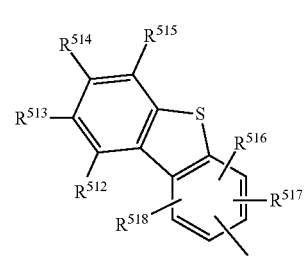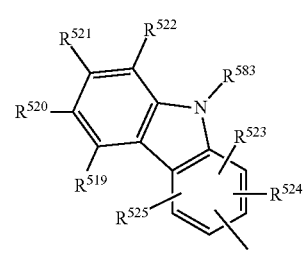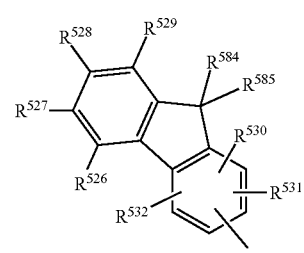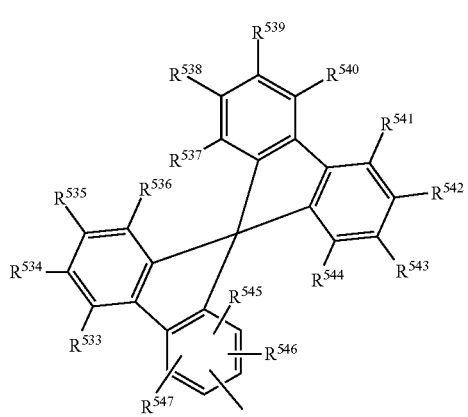

-continued

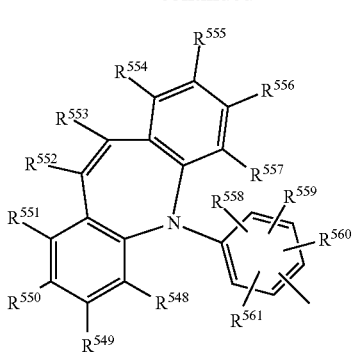
(A32)

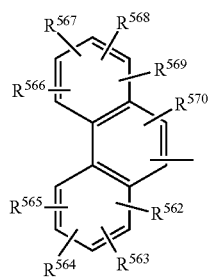
(A33)

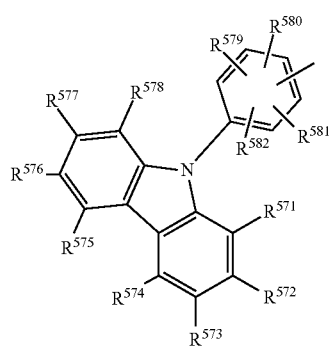
(A34)

(wherein $R^5$ to $R^{582}$ are each independently a hydrogen atom, a halogen atom, a nitro group, a cyano group, or a diphenylamino group, alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with a halogen atom; each $Ar^2$ is independently an aryl group of 6 to 20 carbon atoms which may be substituted with a di($C_{6-20}$ aryl)amino group; $R^{583}$ is a hydrogen atom, an alkyl group of 1 to 20 carbon atoms, alkenyl group of 2 to 20 carbon atoms or alkynyl group of 2 to 20 carbon atoms which may be substituted with $Z^1$, or an aryl group of 6 to 20 carbon atoms or heteroaryl group of 2 to 20 carbon atoms which may be substituted with $Z^4$; $R^{584}$ and $R^{585}$ are each independently an aryl group of 6 to 20 carbon atoms or a heteroaryl group of 2 to 20 carbon atoms which may be substituted with $Z^4$; $Z^1$ is a halogen atom, a nitro group, a cyano group, or an aryl group of 6 to 20 carbon atoms or heteroaryl group of 2 to 20 carbon atoms which may be substituted with $Z^2$; $Z^2$ is a halogen atom, a nitro group, a cyano group, or an alkyl group of 1 to 20 carbon atoms, alkenyl group of 2 to 20 carbon atoms or alkynyl group of 2 to 20 carbon atoms which may be substituted with $Z^3$; $Z^3$ is a halogen atom, a nitro group or a cyano group; $Z^4$ is a halogen atom, a nitro group, a cyano group, or an alkyl group of 1 to 20 carbon atoms, alkenyl group of 2 to 20 carbon atoms or alkynyl group of 2 to 20 carbon atoms which may be substituted with $Z^5$; and $Z^5$ is a halogen atom, a nitro group, a cyano group, or an aryl group of 6 to 20 carbon atoms or heteroaryl group of 2 to 20 carbon atoms which may be substituted with $Z^3$); and k is an integer from 2 to 10;

2. The aniline derivative of 1 above, wherein $R^1$ to $R^4$ are all hydrogen atoms;

3. The aniline derivative of 1 or 2 above, wherein $R^5$ to $R^{582}$ are all hydrogen atoms;

4. A charge-transporting substance consisting of the aniline derivative of any of 1 to 3 above;

5. A charge-transporting material comprising the charge-transporting substance of 4 above;

6. A charge-transporting varnish comprising the charge-transporting substance of 4 above and an organic solvent;

7. The charge-transporting varnish of 6 above, further comprising a dopant substance;

8. The charge-transporting varnish of 7 above, wherein the dopant substance is an arylsulfonic acid compound;

9. A charge-transporting thin film produced using the charge-transporting varnish of any of 6 to 8 above;

10. An organic electroluminescent device comprising the charge-transporting thin film of 9 above; and 11. A method for producing a charge-transporting thin film, comprising the step of coating a substrate with the charge-transporting varnish of any of 6 to 8 above and evaporating off the solvent.

Advantageous Effects of the Invention

The aniline derivative of the invention dissolves readily in organic solvents. By dissolving this together with a dopant in an organic solvent, a charge-transporting varnish can be easily prepared.

Thin films produced from the charge-transporting varnish of the invention exhibit high charge transportability and therefore can be suitably used as thin films for electronic devices such as organic EL devices. In particular, by using such a thin film as a hole-injecting layer in an organic EL device, organic EL devices of excellent longevity can be obtained.

The charge-transporting varnish of the invention can reproducibly form thin films having excellent charge-transporting properties, even using various wet processes capable of film formation over a large area, such as spin coating and slip coating, and therefore is capable of fully accommodating recent advances in the field of organic EL devices.

Embodiment for Carrying Out the Invention

The invention is described more fully below.

The aniline derivative according to this invention has formula (1).

[Chemical Formula 7]

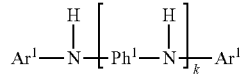

(1)

Ph¹ in formula (1) above is a group of formula (P1) below.

[Chemical Formula 8]

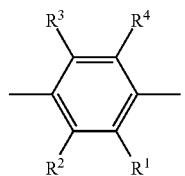
(P1)

Here, R¹ to R⁴ are each independently a hydrogen atom, a halogen atom, a nitro group, a cyano group or an alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with a halogen atom.

The halogen atom is exemplified by fluorine, chlorine, bromine and iodine atoms.

The alkyl group of 1 to 20 carbon atoms may be linear, branched or cyclic. Examples include linear or branched alkyl groups of 1 to 20 carbon atoms, such as methyl, ethyl, n-propyl, isopropyl, n-butyl, isobutyl, s-butyl, t-butyl, n-pentyl, n-hexyl, n-heptyl, n-octyl, n-nonyl and n-decyl groups; and cyclic alkyl groups of 3 to 20 carbon atoms, such as cyclopropyl, cyclobutyl, cyclopentyl, cyclohexyl, cycloheptyl, cyclooctyl, cyclononyl, cyclodecyl, bicyclobutyl, bicyclopentyl, bicyclohexyl, bicycloheptyl, bicyclooctyl, bicyclononyl and bicyclodecyl groups.

Examples of the alkenyl group of 2 to 20 carbon atoms include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl and n-1-eicosenyl groups.

Examples of the alkynyl group of 2 to 20 carbon atoms include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl and n-1-eicosynyl groups.

Examples of aryl groups of 6 to 20 carbon atoms include phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl groups.

Examples of heteroaryl groups of 2 to 20 carbon atoms include 2-thienyl, 3-thienyl, 2-furanyl, 3-furanyl, 2-oxazolyl, 4-oxazolyl, 5-oxazolyl, 3-isooxazolyl, 4-isooxazolyl, 5-isooxazolyl, 2-thiazolyl, 4-thiazolyl, 5-thiazolyl, 3-isothiazolyl, 4-isothiazolyl, 5-isothiazolyl, 2-imidazolyl, 4-imidazolyl, 2-pyridyl, 3-pyridyl and 4-pyridyl groups.

In particular, R¹ to R⁴ are each preferably a hydrogen atom, a fluorine atom, a cyano group, an alkyl group of 1 to 20 carbon atoms which may be substituted with a halogen atom, an aryl group of 6 to 20 carbon atoms which may be substituted with a halogen atom, or a heteroaryl group of 2 to 20 carbon atoms which may be substituted with a halogen atom; more preferably a hydrogen atom, a fluorine atom, a cyano group, an alkyl group of 1 to 10 carbon atoms which may be substituted with a halogen atom, or a phenyl group which may be substituted with a halogen atom; even more preferably a hydrogen atom or a fluorine atom; and most preferably a hydrogen atom.

Groups which are preferred as Ph¹ include, but not limited to, the following.

[Chemical Formula 9]

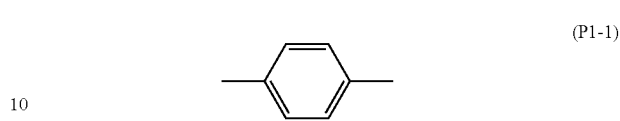
(P1-1)

Each Ar¹ in formula (1) is independently any moiety of above formulas (A1) to (A34).

In particular, formulas (A1) to (A26) and (A29) to (A34) are preferably moieties of groups (A1') to (A26') and (A29') to (A34') below.

Of these, from the standpoint of the balance between the solubility of the aniline compound in organic solvents and the charge transportability of the resulting thin film, (A1'), (A2'), (A25'), (A26') and (A29') are preferred, with (A1'), (A2') and (A29') being more preferred.

Also, as mentioned above, each Ar¹ in formula (1) is independently a moiety of any of formulas (A1) to (A34), although in terms of the ease of compound synthesis and other considerations, it is preferable for the two Ar¹ groups in formula (1) to be identical groups.

[Chemical Formula 10]

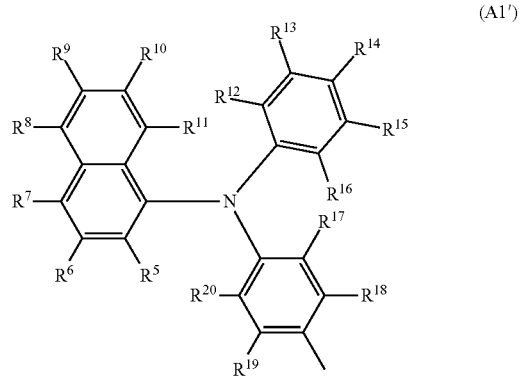
(A1')

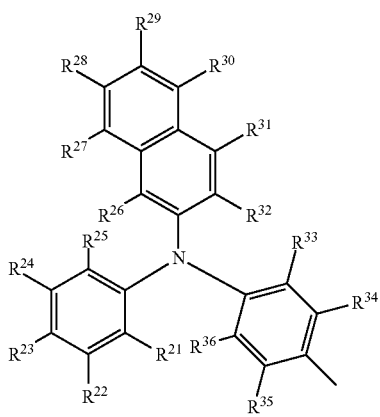
(A2')

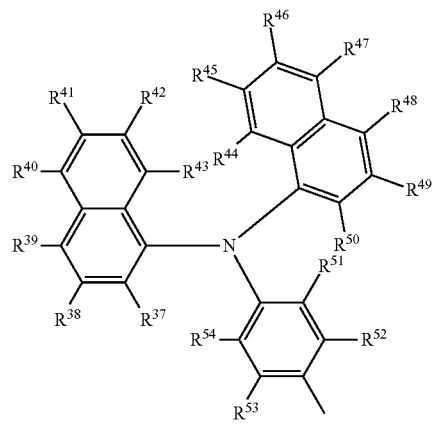
(A3')
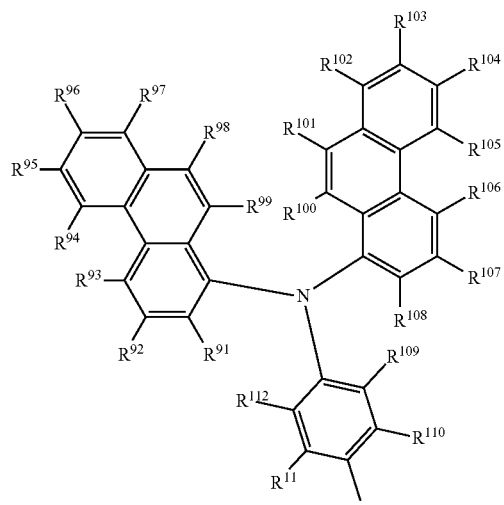
(A6')
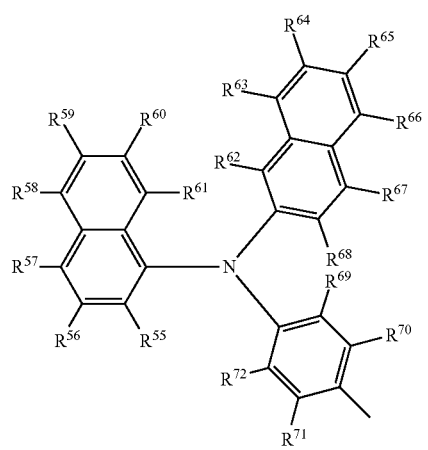
(A4')
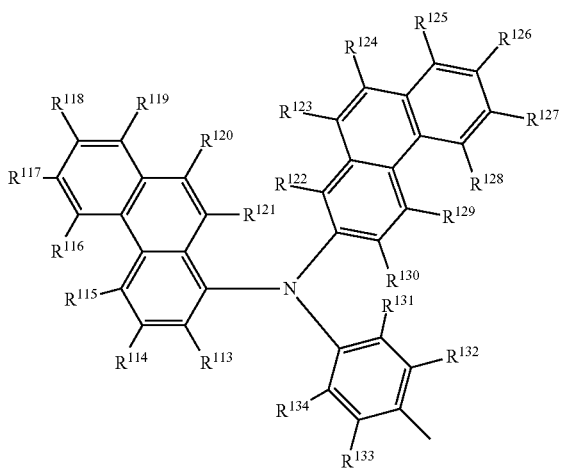
(A7')
(A5')
(A8')

-continued
(A9′)
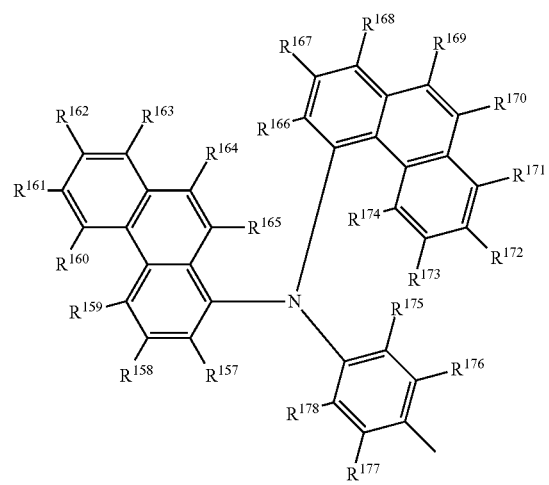
(A10′)
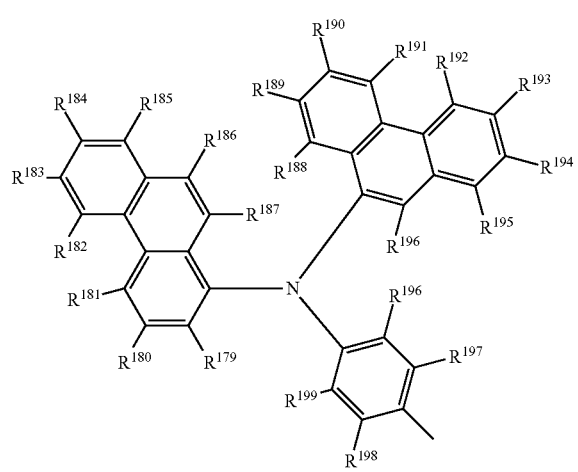
[Chemical Formula 11]
(A11′)
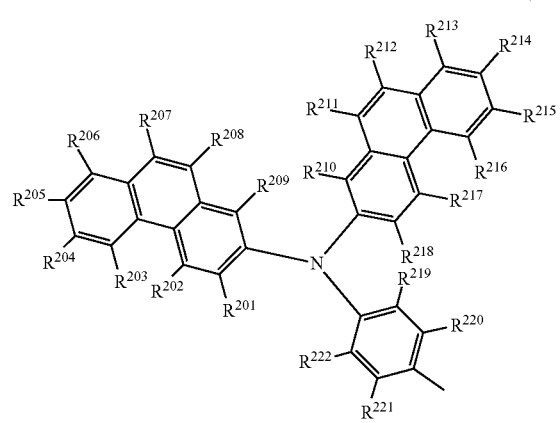
-continued
(A12′)
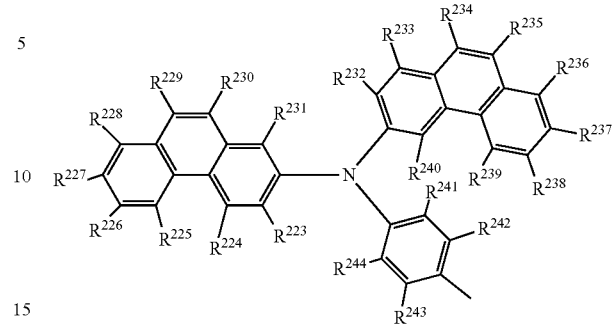
(A13′)
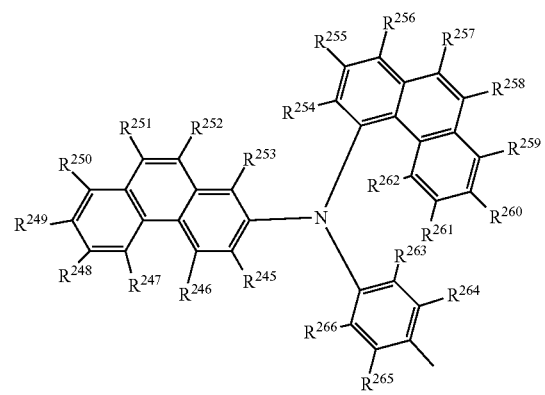
(A14′)
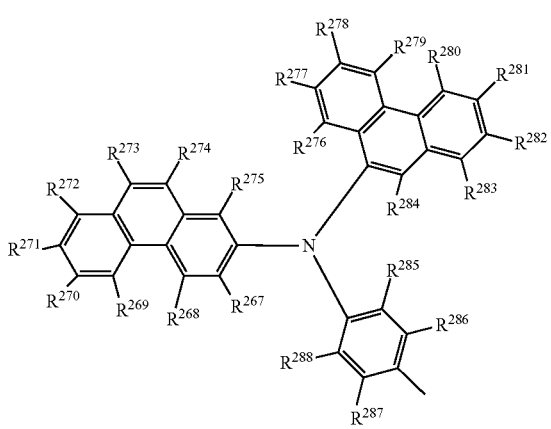
(A15′)
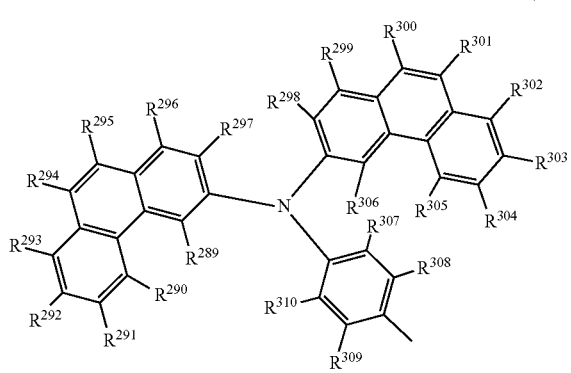

-continued
(A16′)
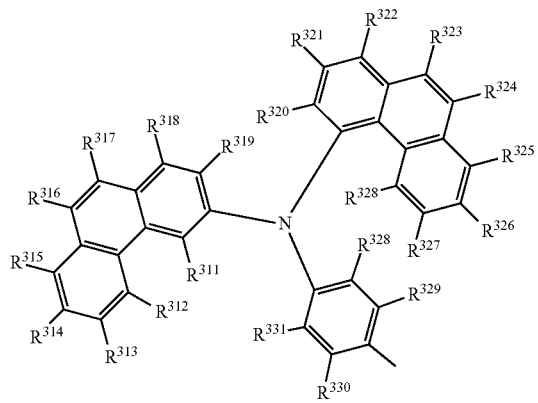
(A17′)
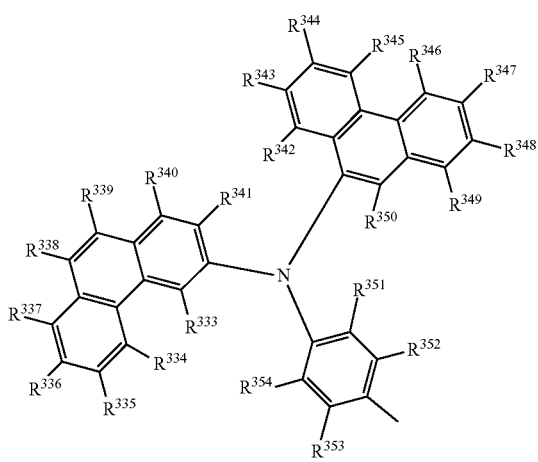
(A18′)
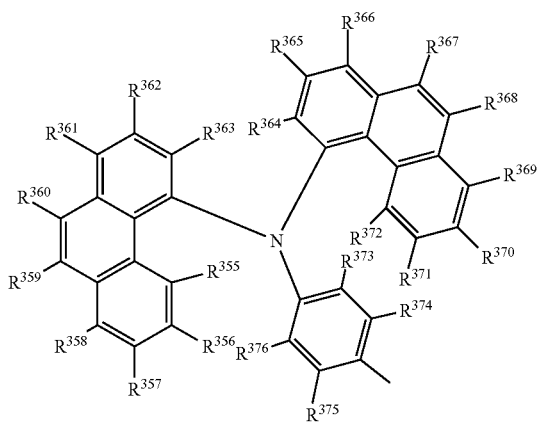
[Chemical Formula 12]
(A19′)
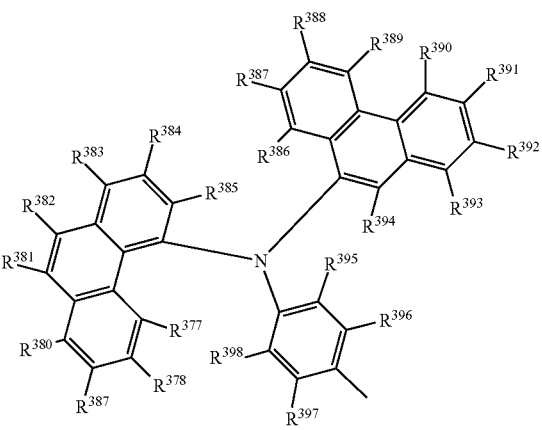
(A20′)
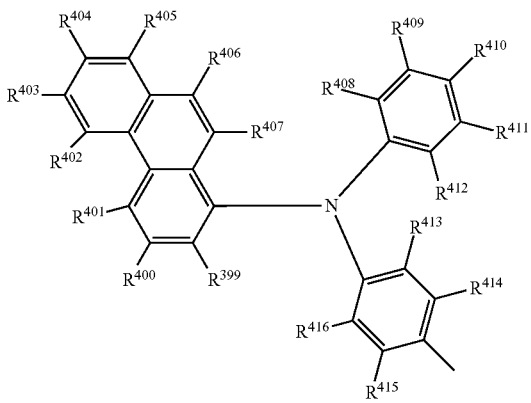
(A21′)
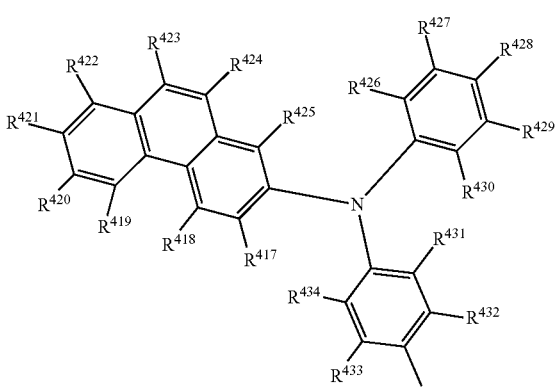

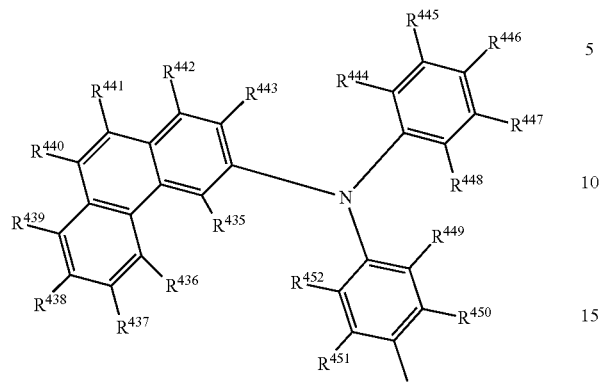
(A22′)
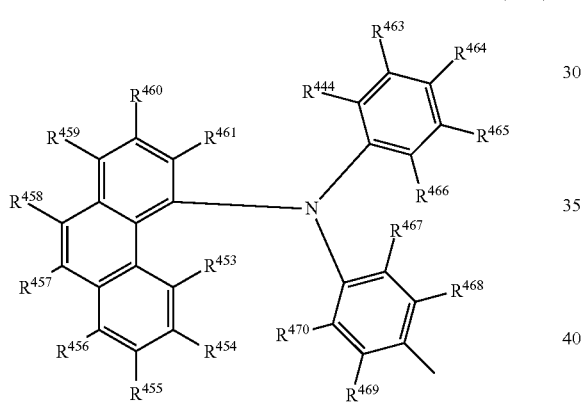
(A23′)
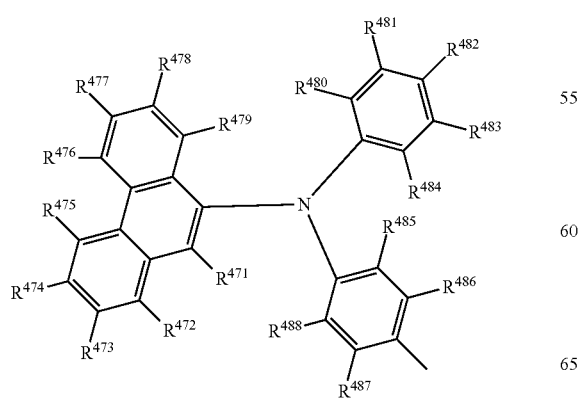
(A24′)
[Chemical Formula 13]
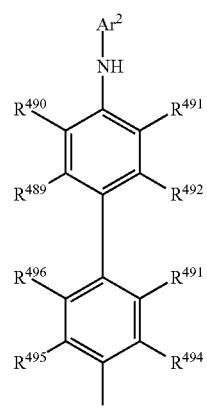
(A25′)
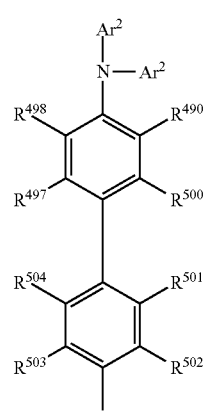
(A26′)
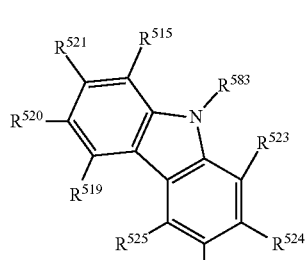
(A29′)
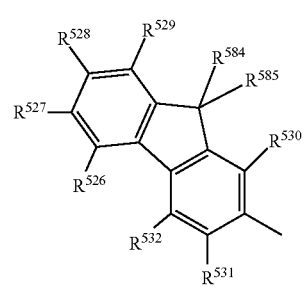
(A30′)

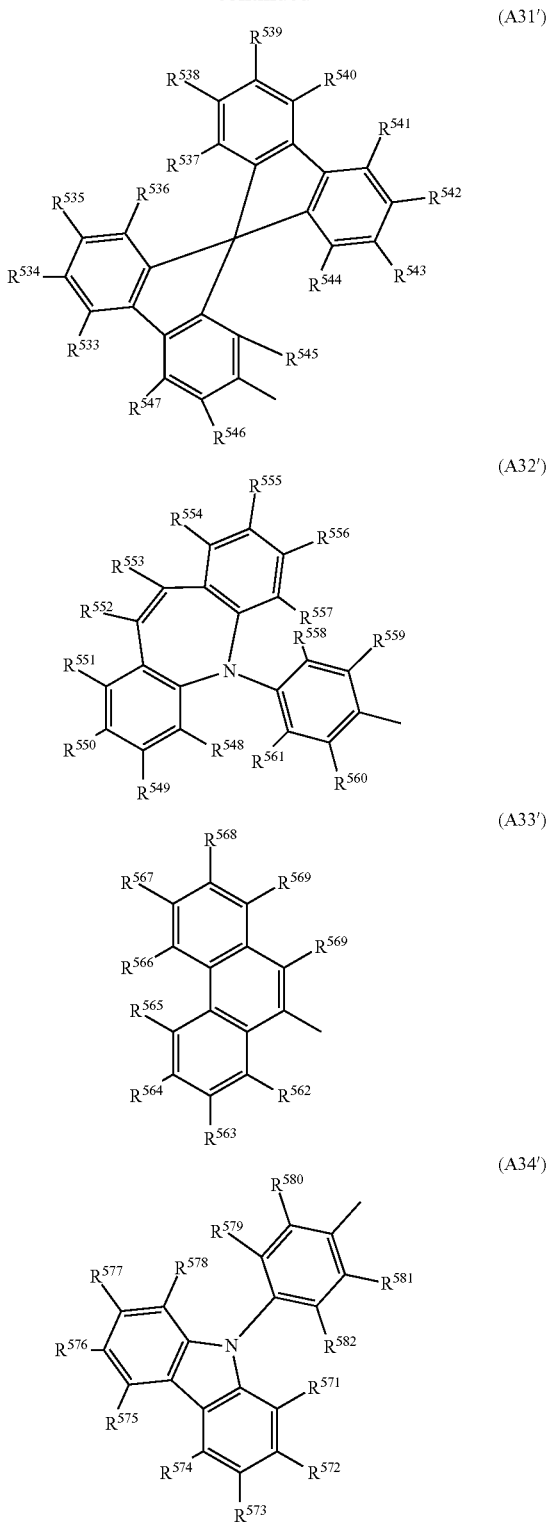

(A31')
(A32')
(A33')
(A34')

$R^5$ to $R^{582}$ are each independently a hydrogen atom, a halogen atom, a nitro group, a cyano group, or a diphenylamino group, alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with a halogen atom. $R^{583}$ is a hydrogen atom, an alkyl group of 1 to 20 carbon atoms, alkenyl group of 2 to 20 carbon atoms or alkynyl group of 2 to 20 carbon atoms which may be substituted with $Z^1$, or an aryl group of 6 to 20 carbon atoms or heteroaryl group of 2 to 20 carbon atoms which may be substituted with $Z^4$. $R^{584}$ and $R^{585}$ are each independently an aryl group of 6 to 20 carbon atoms or a heteroaryl group of 2 to 20 carbon atoms which may be substituted with $Z^4$. $Z^1$ is a halogen atom, a nitro group, a cyano group, or an aryl group of 6 to 20 carbon atoms or heteroaryl group of 2 to 20 carbon atoms which may be substituted with $Z^2$. $Z^2$ is a halogen atom, a nitro group, a cyano group, or an alkyl group of 1 to 20 carbon atoms, alkenyl group of 2 to 20 carbon atoms or alkynyl group of 2 to 20 carbon atoms which may be substituted with $Z^3$. $Z^3$ is a halogen atom, a nitro group or a cyano group. $Z^4$ is a halogen atom, a nitro group, a cyano group, or an alkyl group of 1 to 20 carbon atoms, alkenyl group of 2 to 20 carbon atoms or alkynyl group of 2 to 20 carbon atoms which may be substituted with $Z^5$. $Z^5$ is a halogen atom, a nitro group, a cyano group, or an aryl group of 6 to 20 carbon atoms or heteroaryl group of 2 to 20 carbon atoms which may be substituted with $Z^3$.

These halogen atoms, alkyl groups of 1 to 20 carbon atoms, alkenyl groups of 2 to 20 carbon atoms, alkynyl groups of 2 to 20 carbon atoms, aryl groups of 6 to 20 carbon atoms and heteroaryl groups of 2 to 20 carbon atoms are exemplified in the same way as described above for $R^1$ and $R^2$.

In particular, $R^5$ to $R^{582}$ are each preferably a hydrogen atom, a fluorine atom, a cyano group, a diphenylamino group which may be substituted with a halogen atom, an alkyl group of 1 to 20 carbon atoms which may be substituted with a halogen atom, an aryl group of 6 to 20 carbon atoms which may be substituted with a halogen atom, or a heteroaryl group of 2 to 20 carbon atoms which may be substituted with a halogen atom; more preferably a hydrogen atom, a fluorine atom, a cyano group, an alkyl group of 1 to 10 carbon atoms which may be substituted with a halogen atom, or a phenyl group which may be substituted with a halogen atom; even more preferably a hydrogen atom, a fluorine atom, a methyl group or a trifluoromethyl group; and most preferably a hydrogen atom.

$R^{583}$ is preferably a hydrogen atom, an aryl group of 6 to 20 carbon atoms which may be substituted with $Z^4$, a heteroaryl group of 2 to 20 carbon atoms which may be substituted with $Z^4$, or an alkyl group of 1 to 20 carbon atoms which may be substituted with $Z^1$; more preferably a hydrogen atom, an aryl group of 6 to 14 carbon atoms which may be substituted with $Z^4$, a heteroaryl group of 2 to 14 carbon atoms which may be substituted with $Z^4$, or an alkyl group of 1 to 10 carbon atoms which may be substituted with $Z^1$; even more preferably a hydrogen atom, an aryl group of 6 to 14 carbon atoms which may be substituted with $Z^4$, a nitrogen-containing heteroaryl group of 2 to 14 carbon atoms which may be substituted with $Z^4$, or an alkyl group of 1 to 10 carbon atoms which may be substituted with $Z^1$; and still more preferably a hydrogen atom, a phenyl group which may be substituted with $Z^4$, a 1-naphthyl group which may be substituted with $Z^4$, a 2-naphthyl group which may be substituted with $Z^4$, a 2-pyridyl group which may be substituted with $Z^4$, a 3-pyridyl group which may be substituted with $Z^4$, a 4-pyridyl group which may be substituted with $Z^4$, or a methyl group which may be substituted with $Z'$.

$R^{584}$ and $R^{585}$ are each preferably an aryl group of 6 to 14 carbon atoms which may be substituted with $Z^4$ or a heteroaryl group of 2 to 14 carbon atoms which may be substituted with $Z^4$, more preferably an aryl group of 6 to 14 carbon atoms which may be substituted with $Z^4$, and even more preferably a phenyl group which may be substituted with $Z^4$, a 1-naphthyl group which may be substituted with $Z^4$, or a 2-naphthyl group which may be substituted with $Z^4$.

In $R^{583}$, the substituent $Z^1$ is preferably a halogen atom or an aryl group of 6 to 20 carbon atoms which may be substituted with $Z^2$, more preferably a halogen atom or a phenyl group which may be substituted with $Z^2$, and most preferably does not exist (e.g., is non-substituting).

In $R^{584}$ and $R^{585}$, the substituent $Z^4$ is preferably a halogen atom or an alkyl group of 1 to 20 carbon atoms which may be substituted with $Z^5$, more preferably a halogen atom or an alkyl group of 1 to 4 carbon atoms which may be substituted with $Z^5$, and most preferably does not exist (e.g., is non-substituting).

Also, $Z^2$, $Z^3$ and $Z^5$ are preferably halogen atoms, more preferably fluorine atoms, and most preferably do not exist (i.e., are non-substituting).

Each $Ar^2$ is independently an aryl group of 6 to 20 carbon atoms which may be substituted with a di($C_{6-20}$ aryl)amino group.

The aryl group of 6 to 20 carbon atoms is exemplified in the same way as described above for $R^1$. Examples of di($C_{6-20}$ aryl)amino groups include diphenylamino, 1-naphthylphenylamino, di(1-naphthyl)amino, 1-naphthyl-2-naphthylamino and di(2-naphthyl)amino groups.

$Ar^2$ is preferably a phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, p-(diphenylamino)phenyl, p-(1-naphthylphenylamino)phenyl, p-(di(1-naphthyl)amino)phenyl, p-(1-naphthyl-2-naphthylamino)phenyl or p-(di(2-naphthyl)amino)phenyl group; and more preferably a p-(diphenylamino)phenyl group.

Examples of groups that are preferred as $Ar^1$ include, but are not limited to, the following.

[Chemical Formula 14]

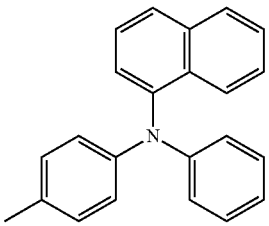
(A1-1)

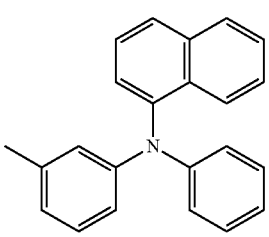
(A1-2)

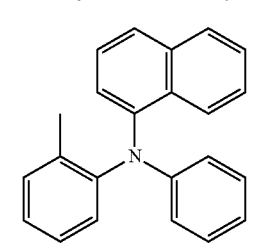
(A1-3)

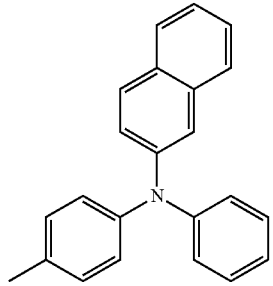
(A2-1)

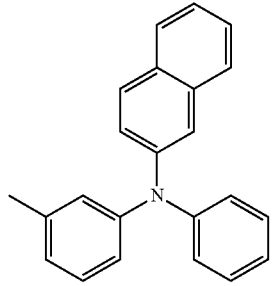
(A2-2)

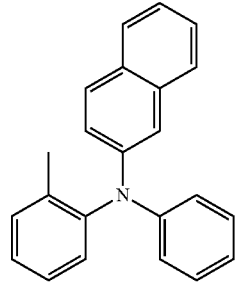
(A2-3)

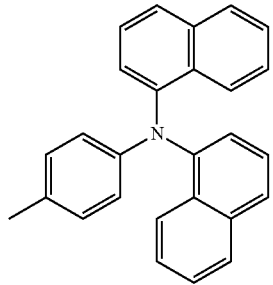
(A3-1)

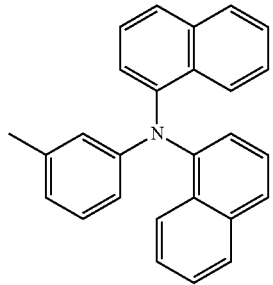
(A3-2)

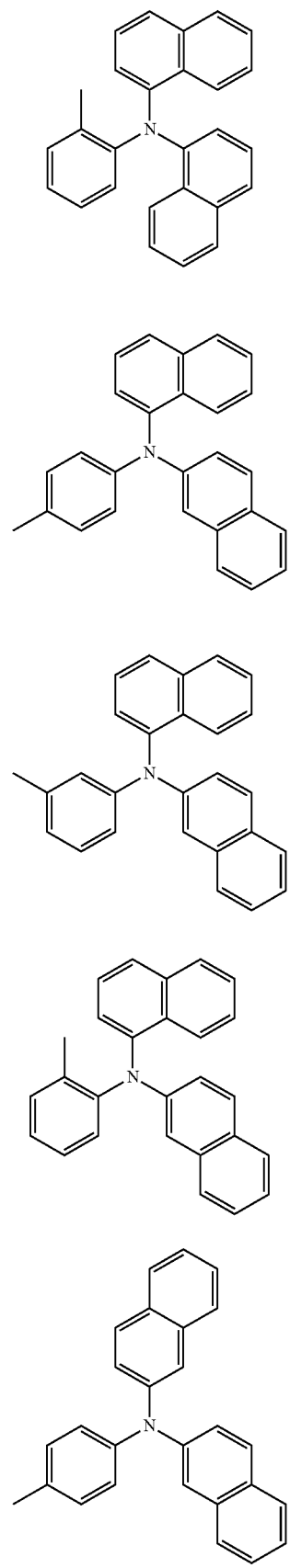
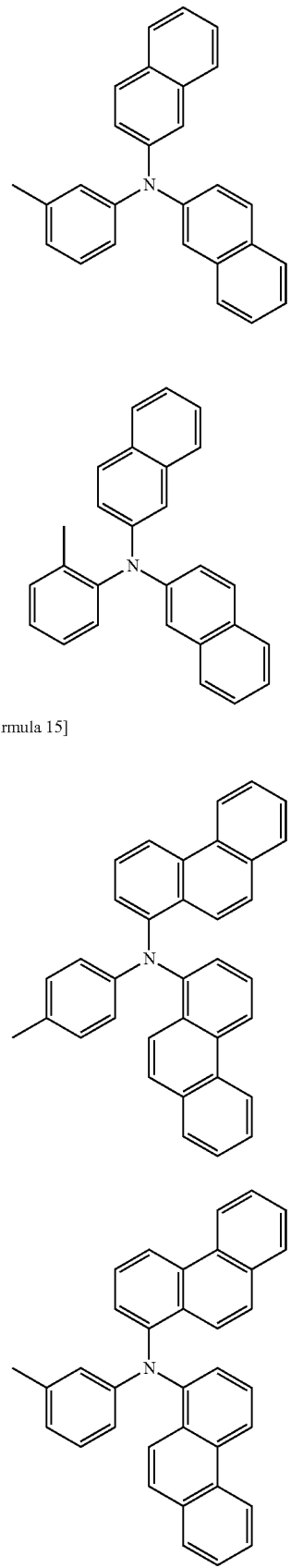
[Chemical Formula 15]

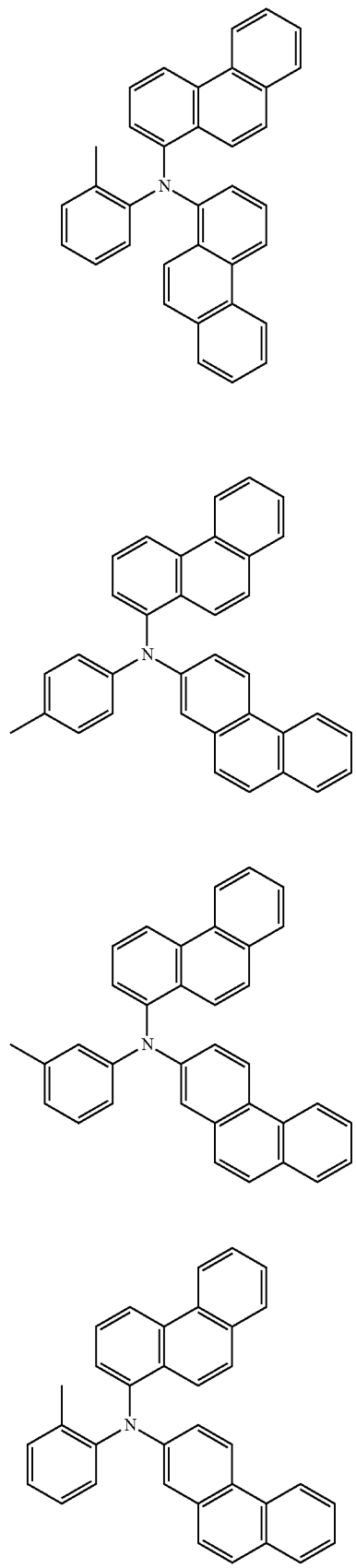
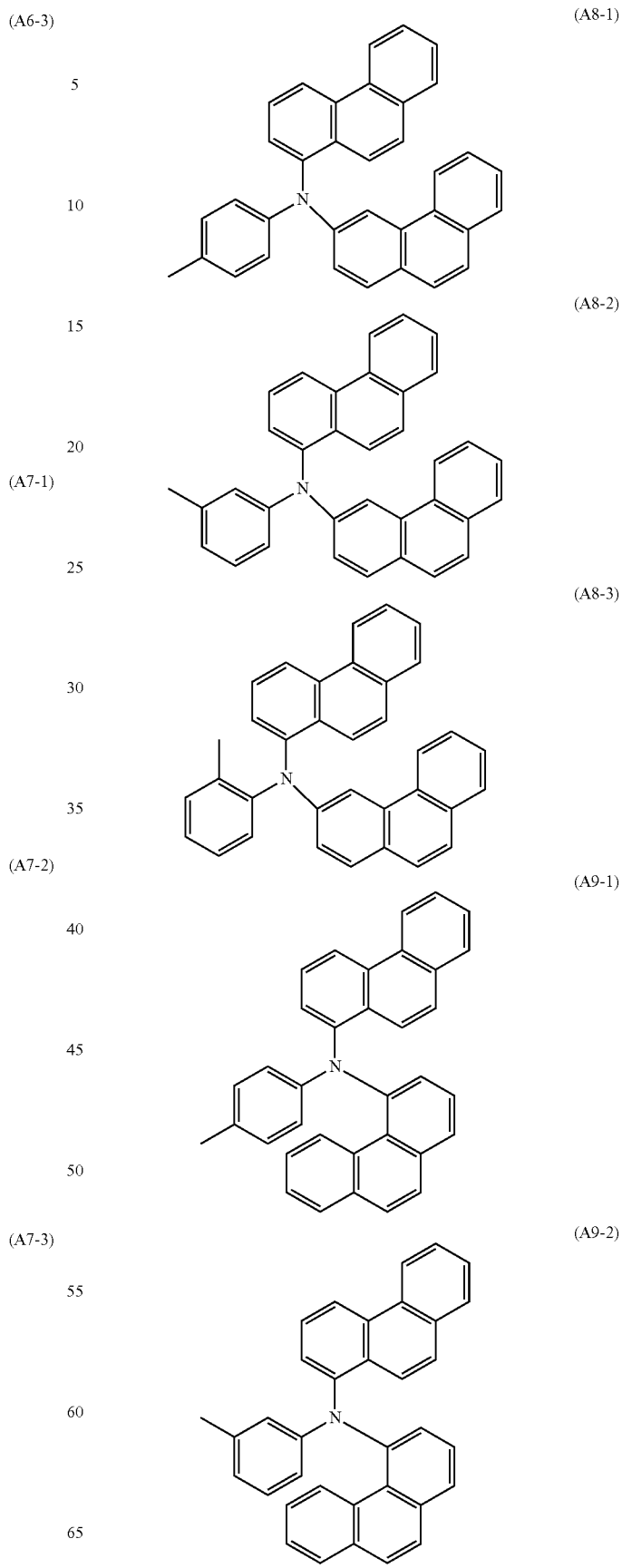

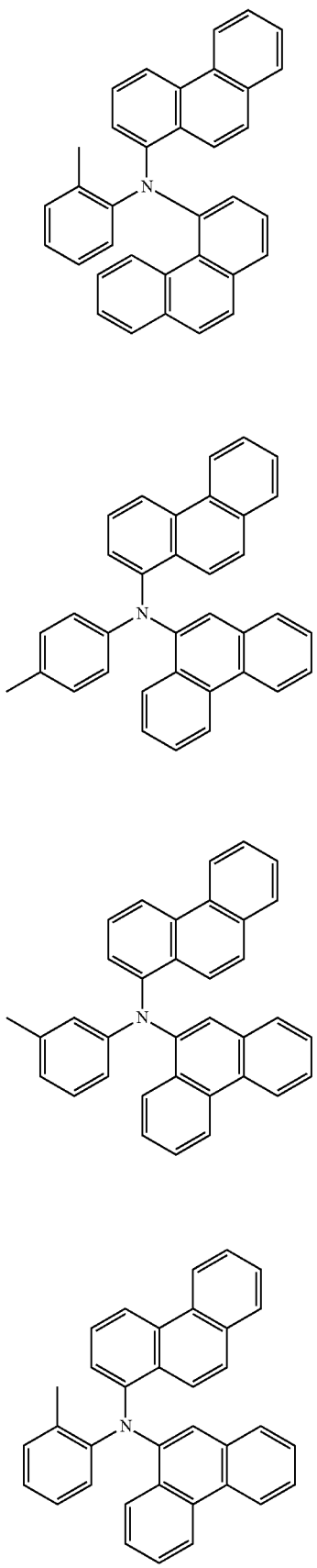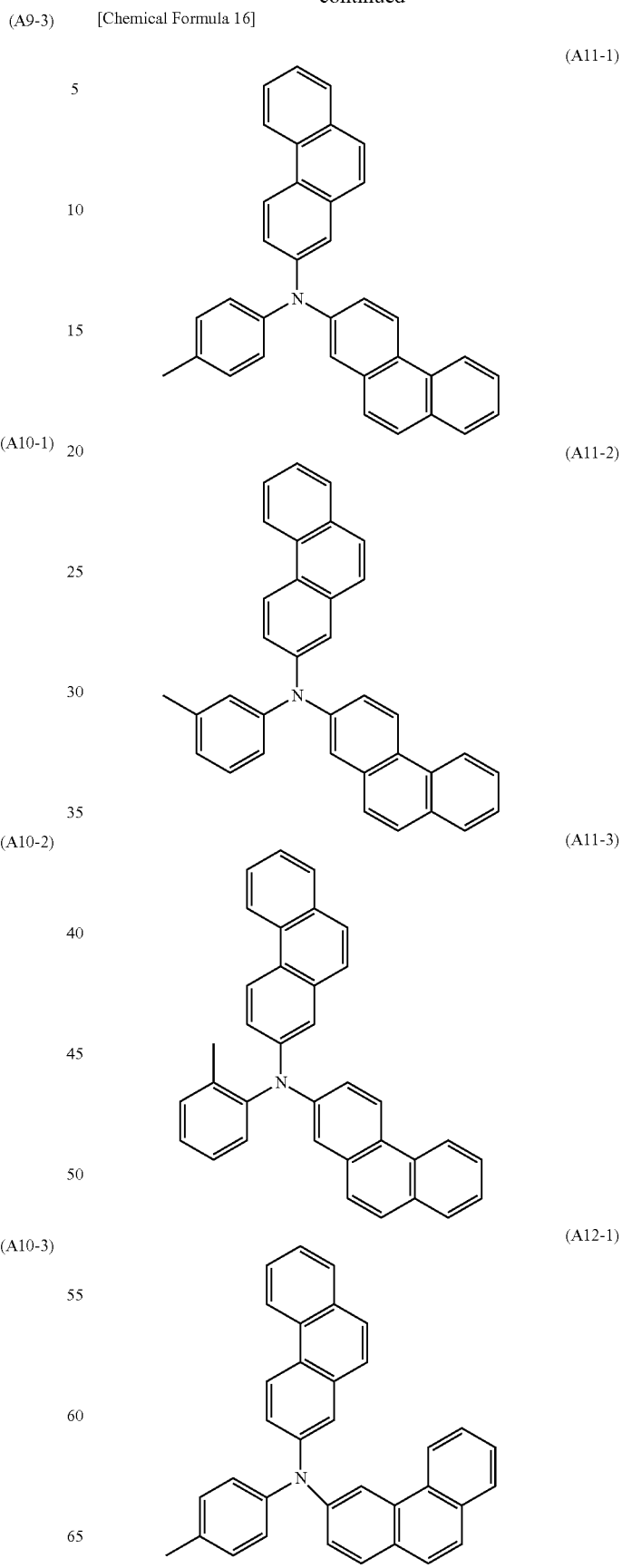

(A12-2)
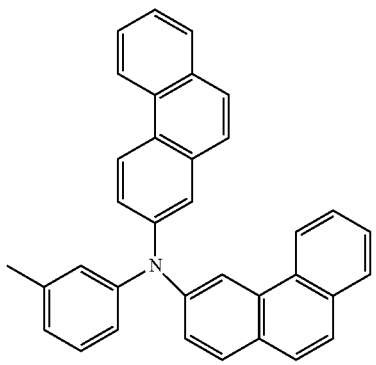
(A12-3)
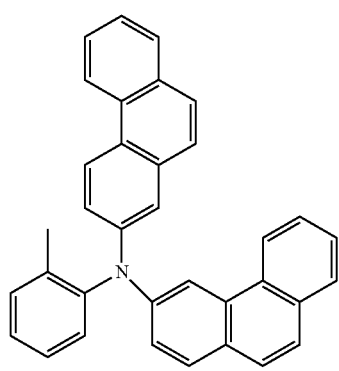
(A13-1)
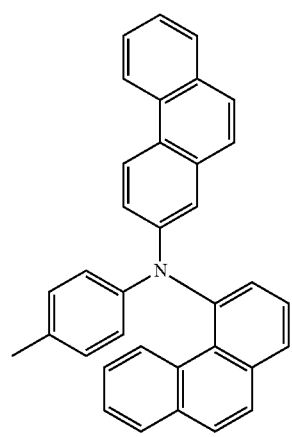
(A13-2)
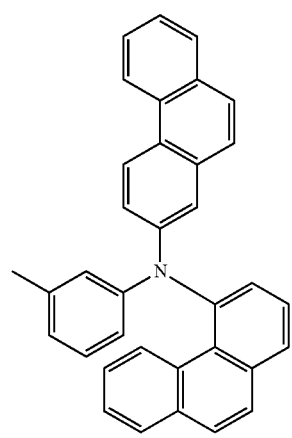
(A13-3)
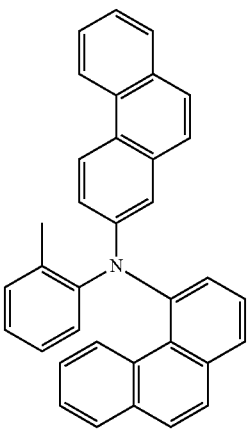
(A14-1)
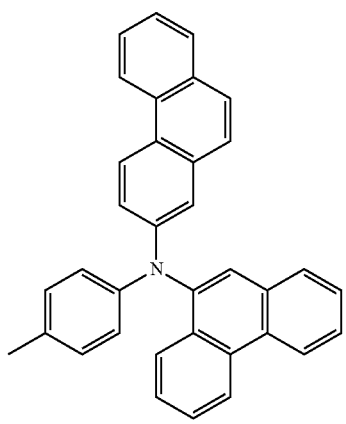
(A14-2)
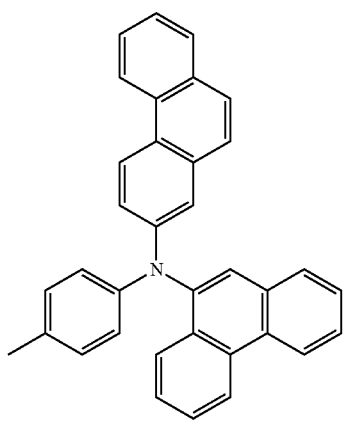

(A14-3)
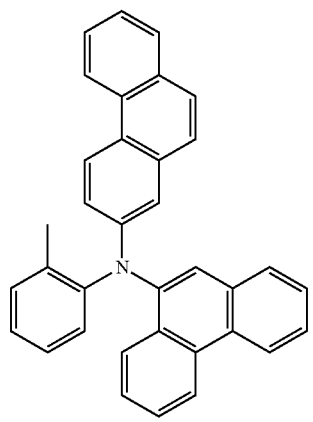
[Chemical Formula 17]
(A15-1)
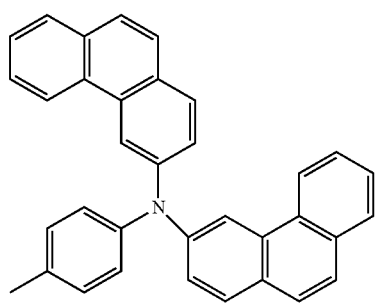
(A15-2)
(A15-3)
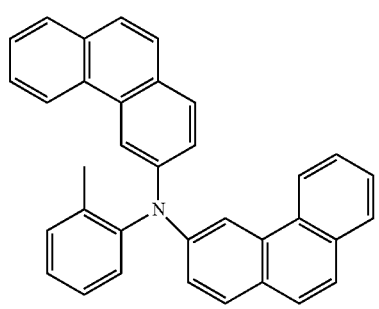
(A16-1)
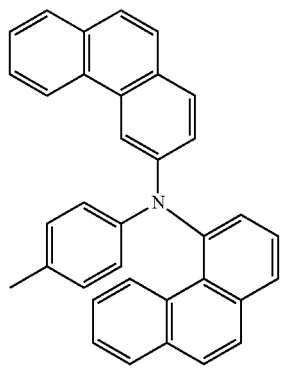
(A16-2)
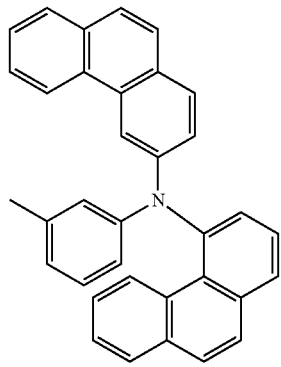
(A16-3)
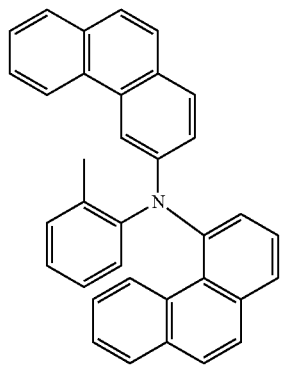
(A17-1)
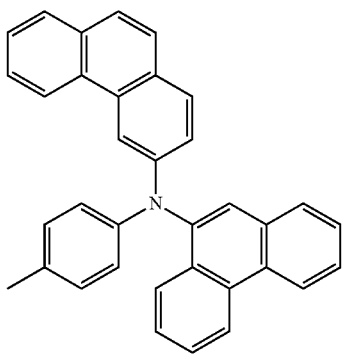

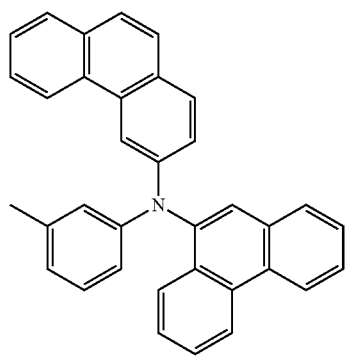
(A17-2)
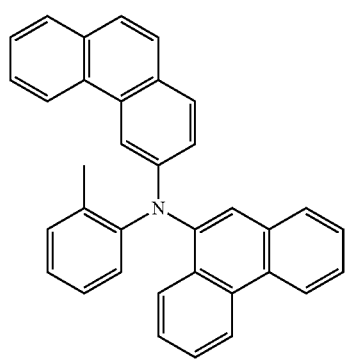
(A17-3)
[Chemical Formula 18]
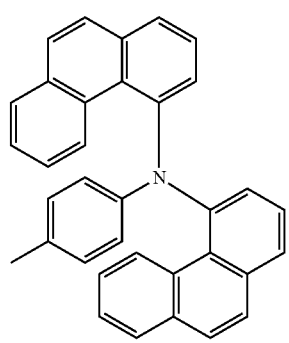
(A18-1)
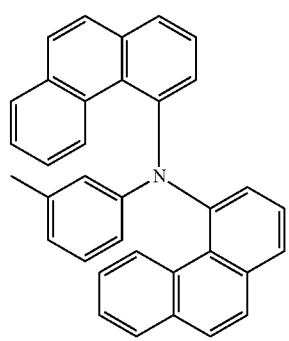
(A18-2)
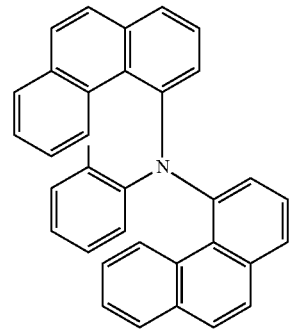
(A18-3)
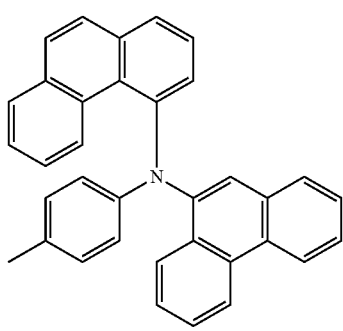
(A19-1)
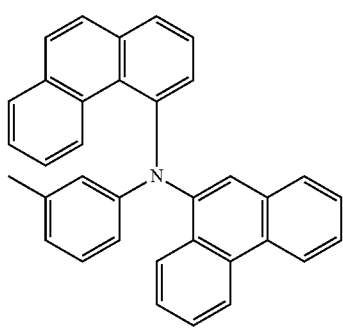
(A19-2)
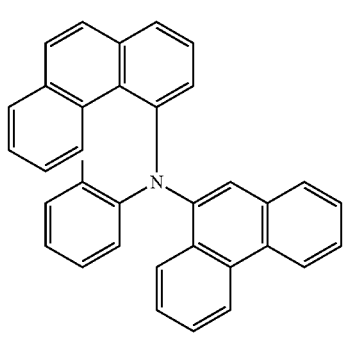
(A19-3)
[Chemical Formula 19]
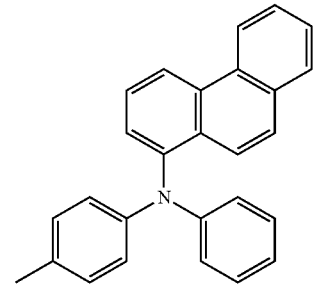
(A20-1)

(A20-2)
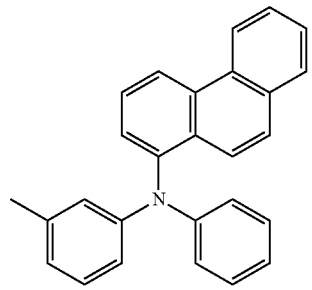
(A20-3)
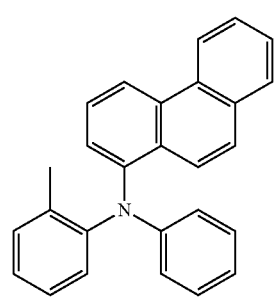
(A21-1)
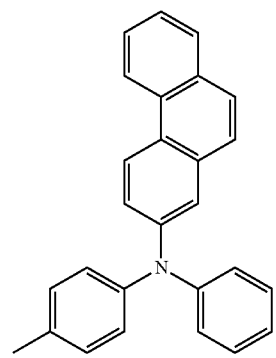
(A21-2)
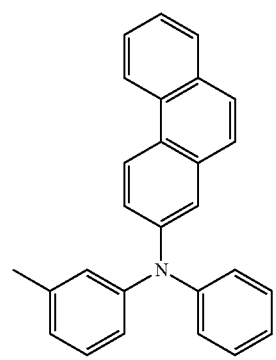
(A21-3)
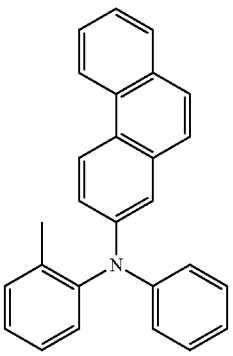
(A22-1)
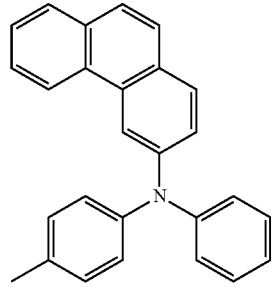
(A22-2)
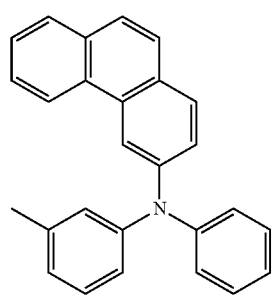
(A22-3)
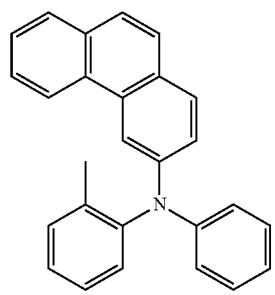
(A23-1)
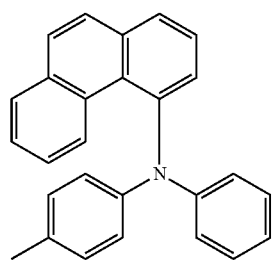

[Chemical Formula 20]
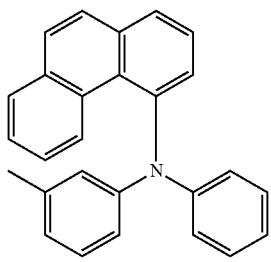 (A23-2)
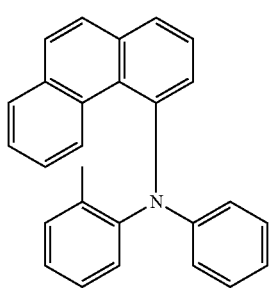 (A23-3)
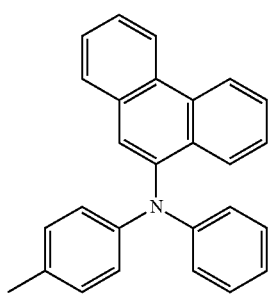 (A24-1)
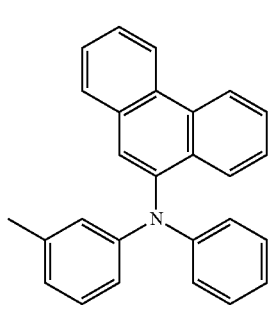 (A24-2)
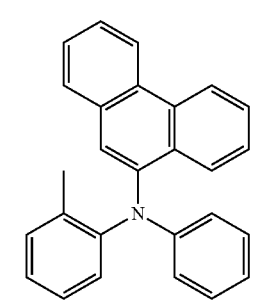 (A24-3)
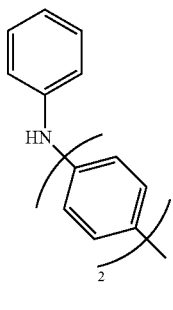 (A25-1)
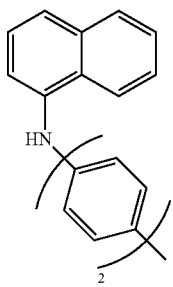 (A25-2)
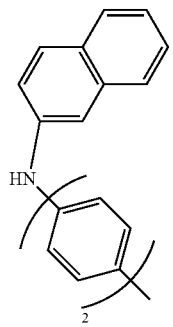 (A25-3)
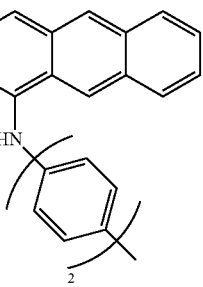 (A25-4)
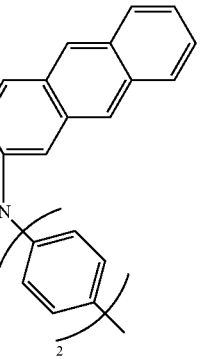 (A25-5)

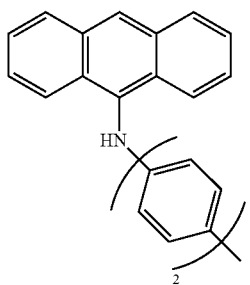
(A25-6)
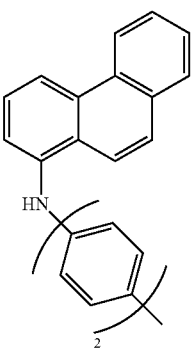
(A25-7)
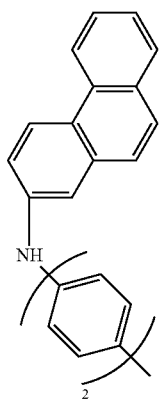
(A25-8)
(A25-9)
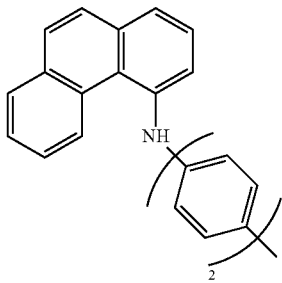
(A25-10)
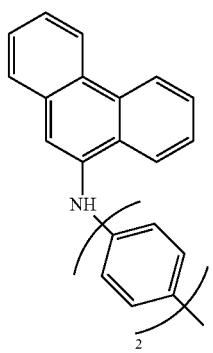
(A25-11)
[Chemical Formula 21]
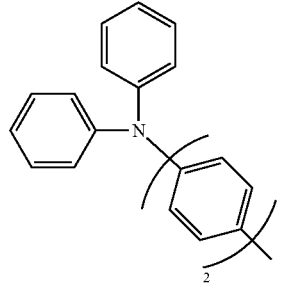
(A26-1)
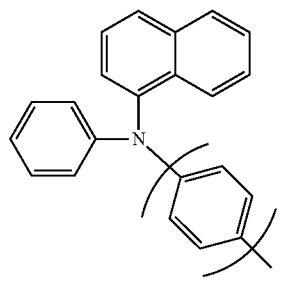
(A26-2)
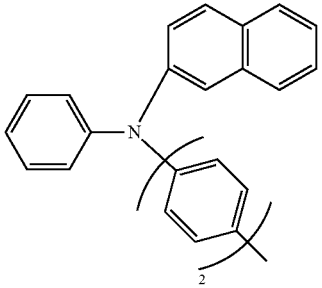
(A26-3)
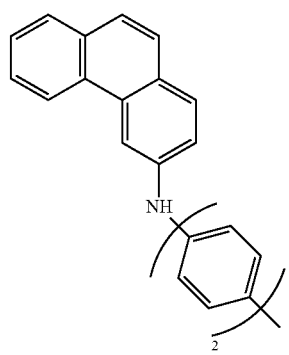

(A26-4)
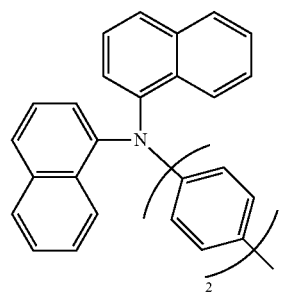
(A26-5)
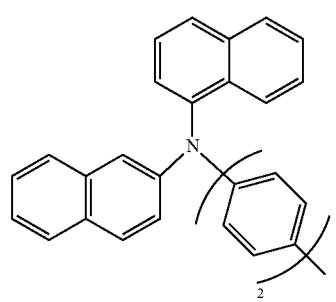
(A26-6)
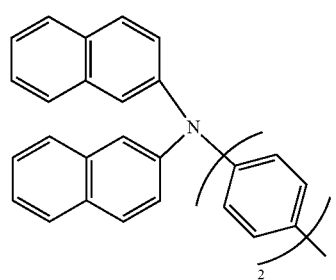
(A26-7)
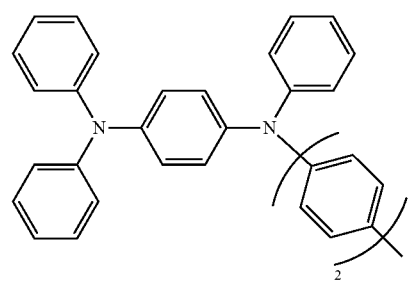
(A26-8)
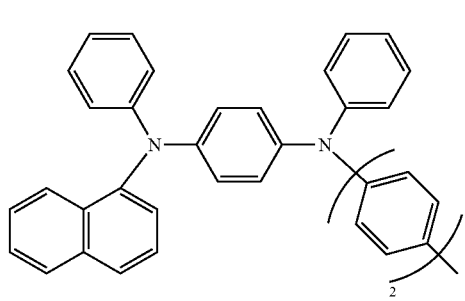
(A26-9)
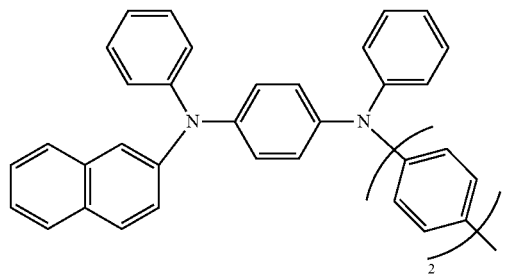
(A26-10)
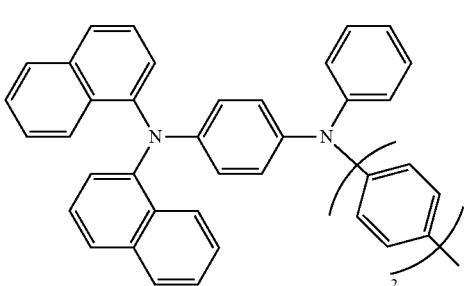
(A26-11)
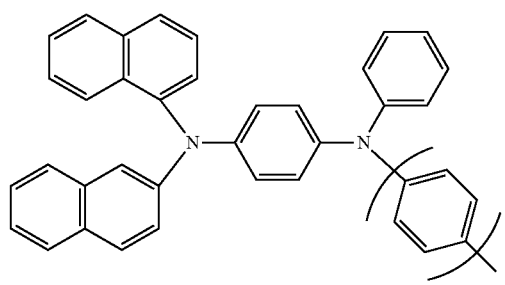
(A26-12)
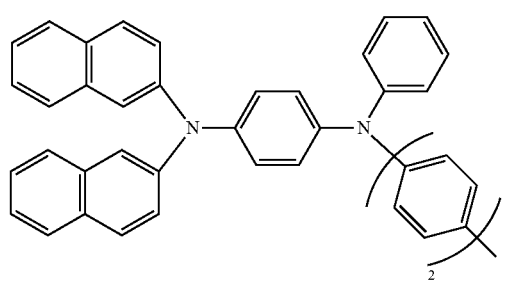
[Chemical Formula 22]
(A26-13)
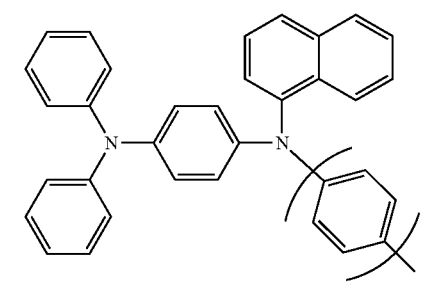

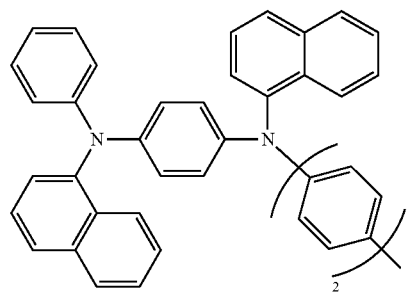
(A26-14)
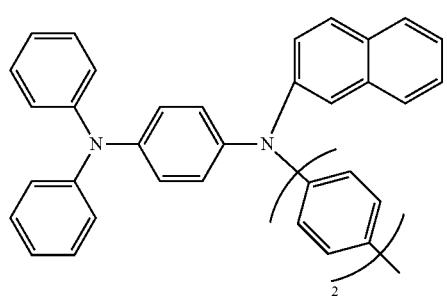
(A26-19)
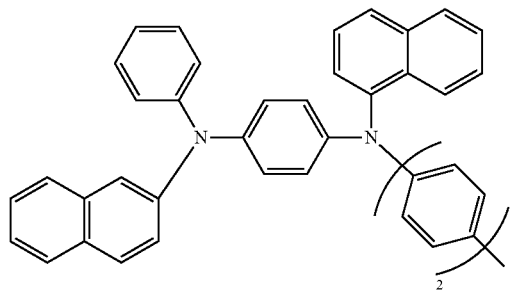
(A26-15)
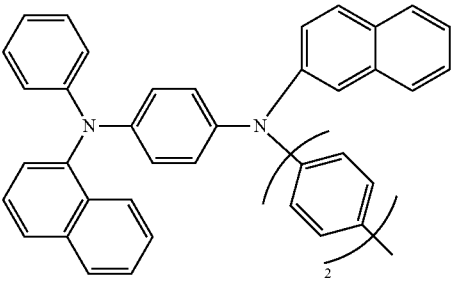
(A26-20)
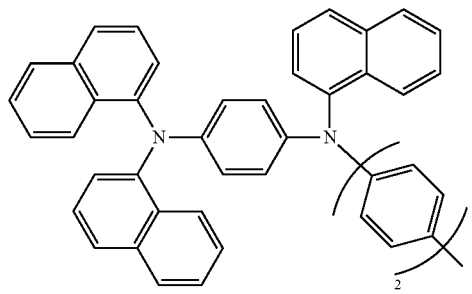
(A26-16)
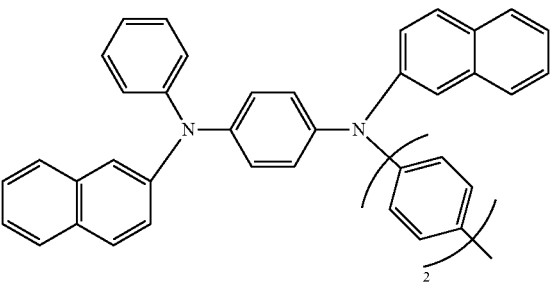
(A26-21)
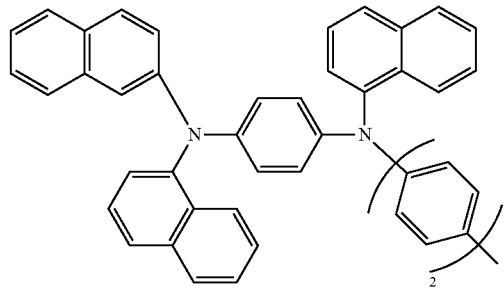
(A26-17)
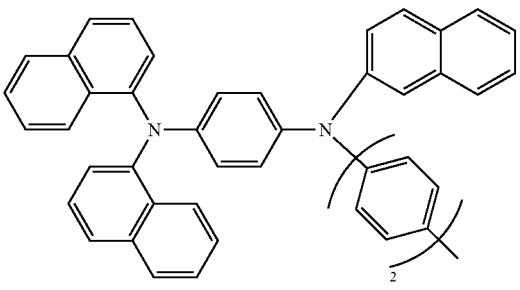
(A26-22)
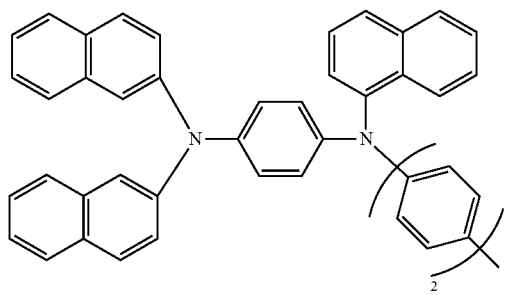
(A26-18)
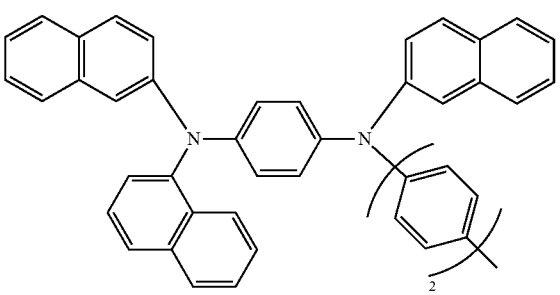
(A26-23)

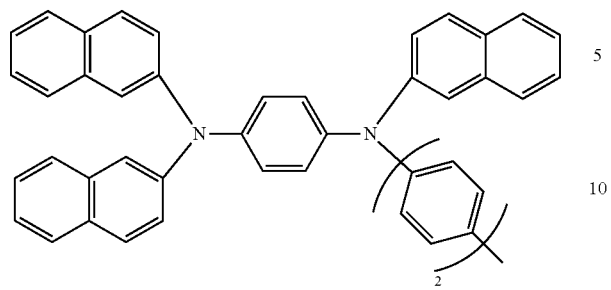 (A26-24)
[Chemical Formula 23]
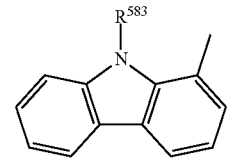 (A29-1)
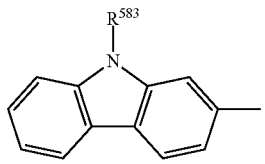 (A29-2)
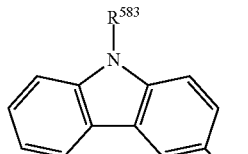 (A29-3)
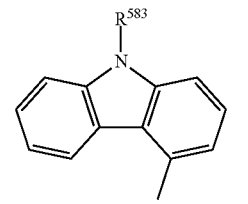 (A29-4)
(wherein R^583 is as defined above)
[Chemical Formula 24]
(A27-1)
(A27-2)
(A27-3)
(A27-4)
(A28-1)
(A28-2)
(A28-3)
(A28-4)
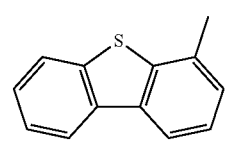
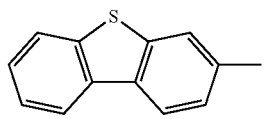
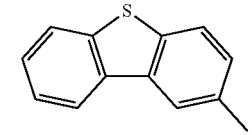
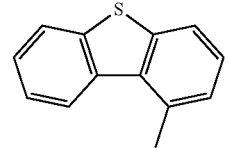
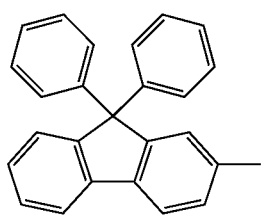 (A30-1)
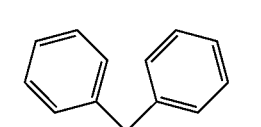 (A30-2)
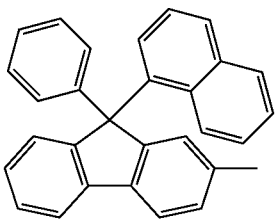 (A30-3)

(A30-4)
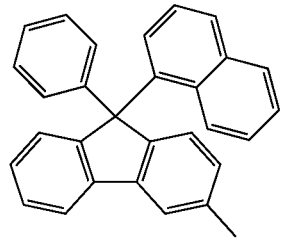
(A30-5)
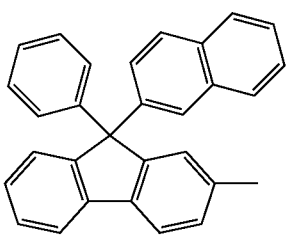
(A30-6)
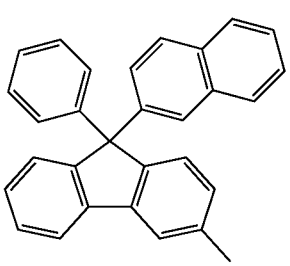
(A30-7)
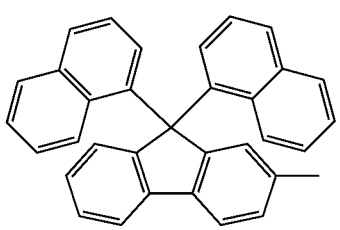
(A30-8)
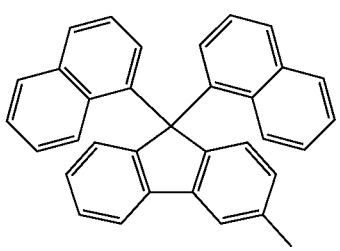
(A30-9)
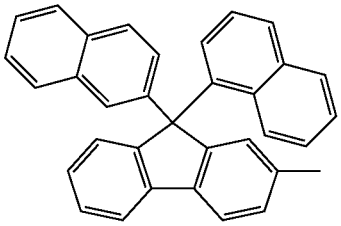
(A30-10)
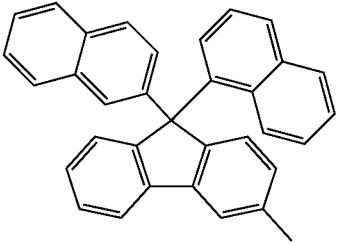
(A30-11)
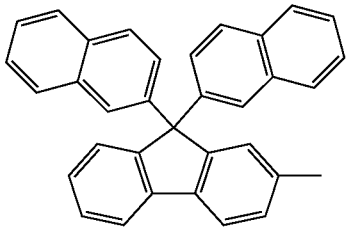
(A30-12)
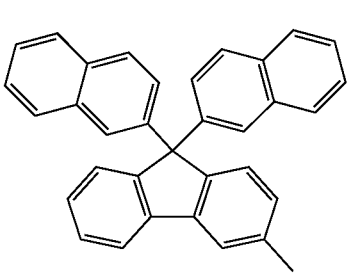
(A31-1)
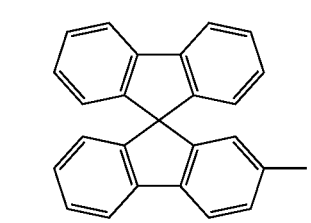
(A31-2)
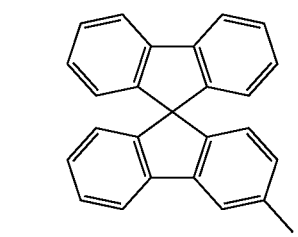
[Chemical Formula 25]
(A32-1)
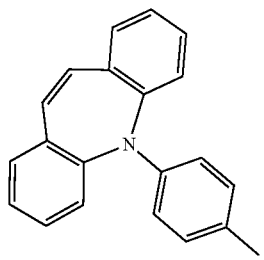

(A32-2)
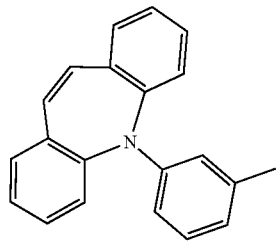
(A32-3)
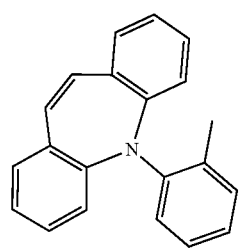
(A33-1)
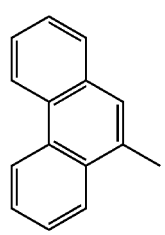
(A33-2)
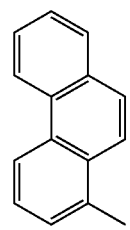
(A33-3)
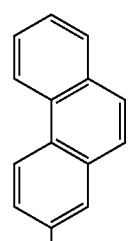
(A33-4)
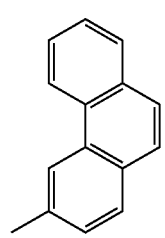
(A33-5)
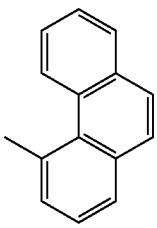
(A34-1)
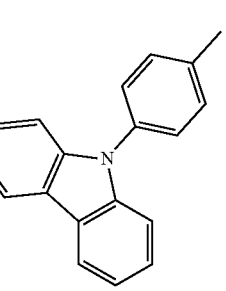
(A34-2)
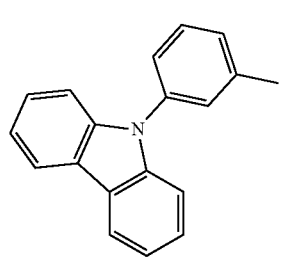
(A34-3)
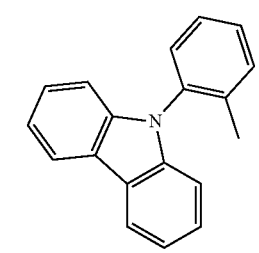
In this invention, examples of groups that are preferred as $R^3$ include, but are not limited to, the following.
[Chemical Formula 26]
(N1)
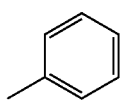
(N2)
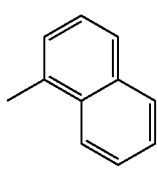

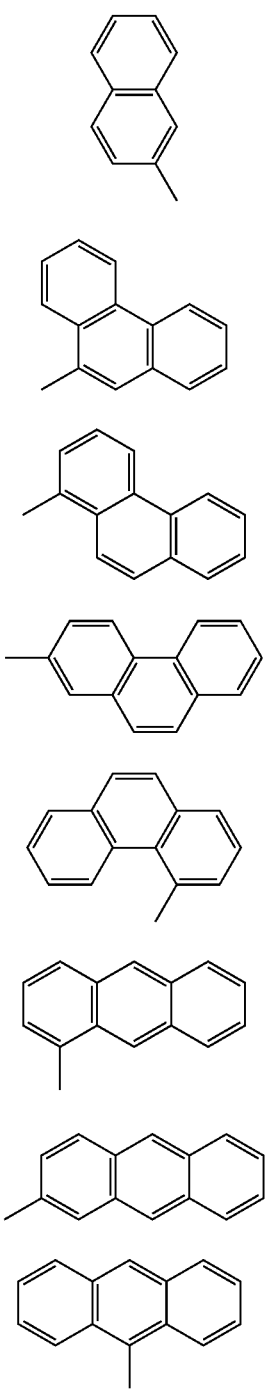
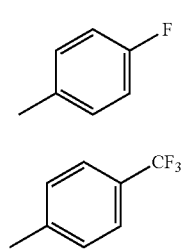

-continued
(N24) 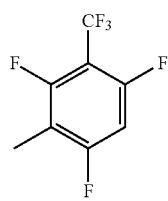
(N25) 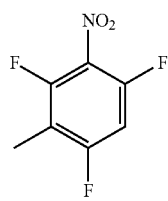
(N26) 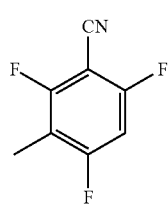
(N27) 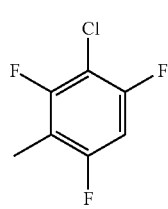
(N28) 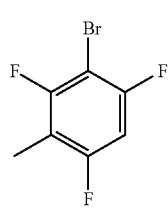
(N29) 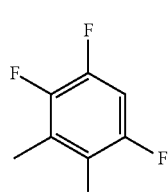
(N30) 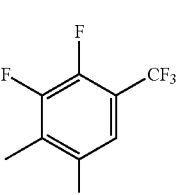
(N31) 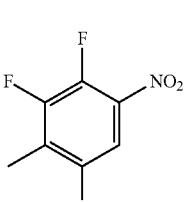
-continued
(N32) 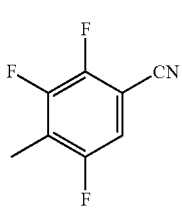
[Chemical Formula 28]
(N33) 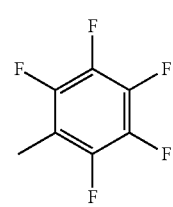
(N34) 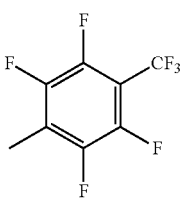
(N35) 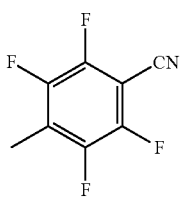
(N36) 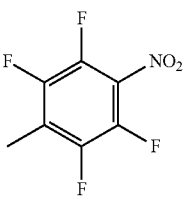
(N37) 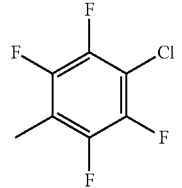
(N38) 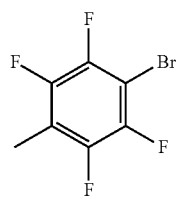

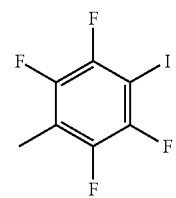 (N39)
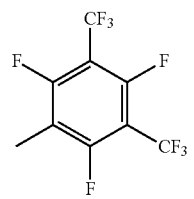 (N40)
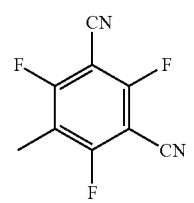 (N41)
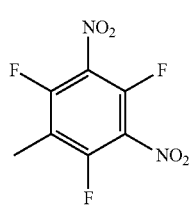 (N42)
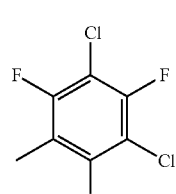 (N43)
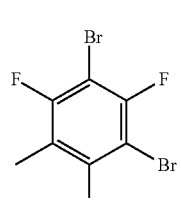 (N44)
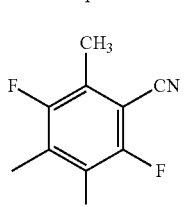 (N45)
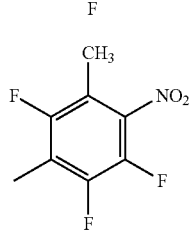 (N46)
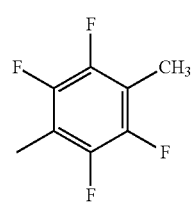 (N47)
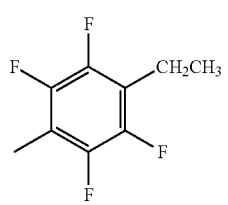 (N48)
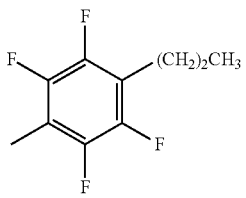 (N49)
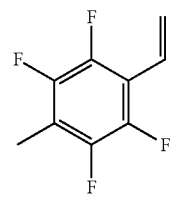 (N50)
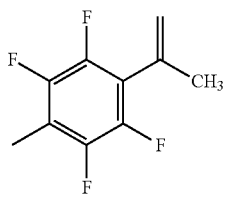 (N51)
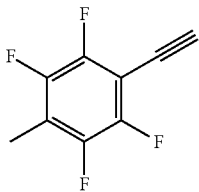 (N52)
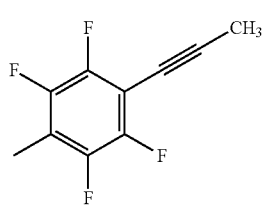 (N53)

[Chemical Formula 29]
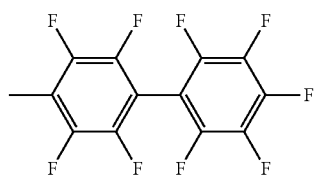
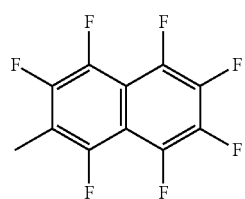
[Chemical Formula 30]
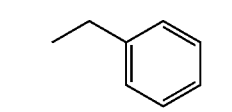
(N54)
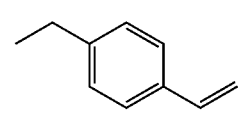
(N55)
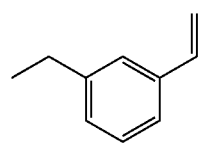
(N56)
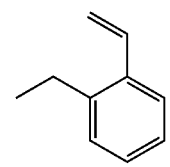
(N57)
(N58)
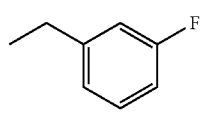
(N59)
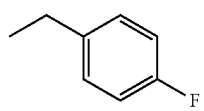
(N60)
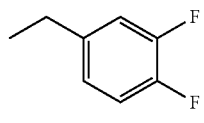
(N61)
(N50)
(N62)
(N63)
(N64)
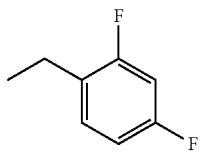
(N65)
(N66)
(N67)
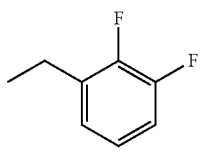
(N68)
(N69)
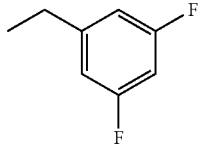
(N70)
[Chemical Formula 31]
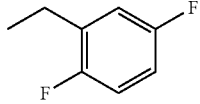
(N71)
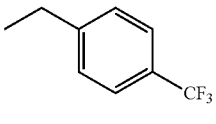
(N72)
(N73)
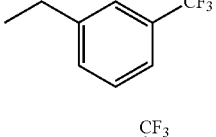
(N74)
(N75)

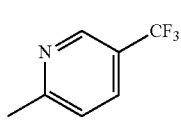

(N76)

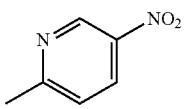

(N77)

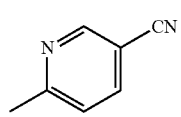

(N78)

The subscript k in formula (1) is an integer from 2 to 10. From the standpoint of increasing the solubility of the compound in organic solvents, k is preferably from 2 to 5, more preferably from 2 to 4, and even more preferably 2 or 3.

In the invention, the number of carbon atoms on the alkyl, alkenyl and alkynyl groups is preferably 10 or less, more preferably 6 or less, and even more preferably 4 or less.

The number of carbon atoms on the aryl and heteroaryl groups is preferably 14 or less, more preferably 10 or less, and even more preferably 6 or less.

The inventive aniline derivative of formula (1) can be synthesized by reacting a diamine compound of formula (2) with an aryl compound of formula (3) in the presence of a catalyst.

[Chemical Formula 32]

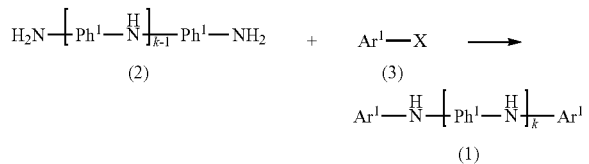

Here, X is a halogen atom or a pseudo-halogen group, and $Ar^1$, $Ph^1$ and k are as defined above.

The halogen atom is exemplified in the same way as above.

The pseudo-halogen group is exemplified by (fluoro) alkylsulfonyloxy groups such as methanesulfonyloxy, trifluoromethanesulfonyloxy and nanofluorobutanesulfonyloxy groups; and aromatic sulfonyloxy groups such as benzenesulfonyloxy and toluenesulfonyloxy groups.

The charging ratio between the diamine compound of formula (2) and the aryl compound of formula (3) is preferably set so as to make the amount of aryl compound about 1 to 1.2 equivalents, with respect to the molar amount of terminal $NH_2$ groups on the diamine compound.

The catalyst used in the reaction is exemplified by copper catalysts such as copper chloride, copper bromide and copper iodide; and palladium catalysts such as tetrakis(triphenylphosphine)palladium ($Pd(PPh_3)_4$), bis(triphenylphosphine)dichloropalladium ($Pd(PPh_3)_2Cl_2$), bis(benzylideneacetone)palladium ($Pd(dba)_2$), tris(benzylideneacetone)dipalladium ($Pd_2(dba)_3$), bis(tri(t-butylphosphine)palladium ($Pd(P-t-Bu_3)_2$) and palladium acetate ($Pd(OAc)_2$). These catalysts may be used singly, or two or more may be used in combination. Also, these catalysts may be used together with suitable known ligands.

Examples of such ligands include tertiary phosphines such as triphenylphosphine, tri-o-tolylphosphine, diphenylmethylphosphine, phenyldimethylphosphine, trimethylphosphine, triethylphosphine, tributylphosphine, tri-t-butylphosphine, di-t-butyl(phenyl)phosphine, di-t-butyl(4-dimethylaminophenyl)phosphine, 1,2-bis(diphenylphosphino)ethane, 1,3-bis(diphenylphosphino)propane, 1,4-bis(diphenylphosphino)butane and 1,1'-bis(diphenylphosphino)ferrocene; and tertiary phosphites such as trimethylphosphite, triethylphosphite and triphenylphosphite.

The amount of catalyst used may be set to about 0.2 mole per mole of the aryl compound of formula (3), with about 0.15 mole being preferred.

When ligands are used, the amount thereof may be set to from 0.1 to 5 equivalents, and preferably from 1 to 2 equivalents, with respect to the metal complex used.

In cases where the starting compounds are all solids or from the standpoint of efficiently obtaining the target aniline derivative, each of the above reactions is carried out in a solvent. When a solvent is used, the type thereof is not particularly limited, provided that it does not have an adverse influence on the reaction. Illustrative examples include aliphatic hydrocarbons (pentane, n-hexane, n-octane, n-decane, decalin, etc.), halogenated aliphatic hydrocarbons (chloroform, dichloromethane, dichloroethane, carbon tetrachloride, etc.), aromatic hydrocarbons (benzene, nitrobenzene, toluene, o-xylene, m-xylene, p-xylene, mesitylene, etc.), halogenated aromatic hydrocarbons (chlorobenzene, bromobenzene, o-dichlorobenzene, m-dichlorobenzene, p-dichlorobenzene, etc.), ethers (diethyl ether, diisopropyl ether, t-butyl methyl ether, tetrahydrofuran, dioxane, 1,2-dimethoxyethane, 1,2-diethoxyethane, etc.), ketones (acetone, methyl ethyl ketone, methyl isobutyl ketone, di-n-butyl ketone, cyclohexanone, etc.), amides (N,N-dimethylformamide, N,N-dimethylacetamide, etc.), lactams and lactones (N-methylpyrrolidone, γ-butyrolactone, etc.), ureas (N,N-dimethylimidazolidinone, tetramethylurea, etc.), sulfoxides (dimethylsulfoxide, sulfolane, etc.), and nitriles (acetonitrile, propionitrile, butyronitrile, etc.). These solvents may be used singly, or two or more may be used in admixture.

The reaction temperature may be suitably set in the range of the melting point to the boiling point of the solvent used, with a temperature of about 0 to 200° C. being preferred, and a temperature of 20 to 150° C. being more preferred.

Following reaction completion, the target aniline derivative can be obtained by work-up in the usual manner.

Illustrative examples of the aniline derivative of formula (1) include, but are not limited to, those shown below. In the tables, "Both $Ar^1$", "$Ph^1$", "k" and "$R^{583}$" represent specific entities in formula (1) for the compounds shown on the respective lines of the table. For example, the compound of formula (E1) and the compound of formula (E145) are respectively as follows.

[Chemical Formula 33]

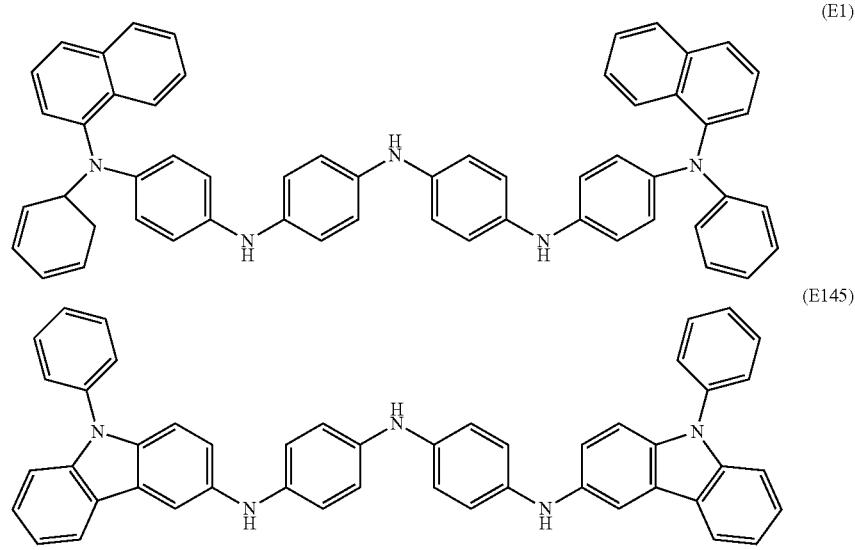

| Compound | Both Ar¹ | Ph¹ | k |
|---|---|---|---|
| (E1) | (A1-1) | (P1-1) | 2 |
| (E2) | (A2-1) | (P1-1) | 2 |
| (E3) | (A3-1) | (P1-1) | 2 |
| (E4) | (A4-1) | (P1-1) | 2 |
| (E5) | (A5-1) | (P1-1) | 2 |
| (E6) | (A6-1) | (P1-1) | 2 |
| (E7) | (A7-1) | (P1-1) | 2 |
| (E8) | (A8-1) | (P1-1) | 2 |
| (E9) | (A9-1) | (P1-1) | 2 |
| (E10) | (A10-1) | (P1-1) | 2 |
| (E11) | (A11-1) | (P1-1) | 2 |
| (E12) | (A12-1) | (P1-1) | 2 |
| (E13) | (A13-1) | (P1-1) | 2 |
| (E14) | (A14-1) | (P1-1) | 2 |
| (E15) | (A15-1) | (P1-1) | 2 |
| (E16) | (A16-1) | (P1-1) | 2 |
| (E17) | (A17-1) | (P1-1) | 2 |
| (E18) | (A18-2) | (P1-1) | 2 |
| (E19) | (A19-2) | (P1-1) | 2 |
| (E20) | (A20-1) | (P1-1) | 2 |
| (E21) | (A21-1) | (P1-1) | 2 |
| (E22) | (A22-1) | (P1-1) | 2 |
| (E23) | (A23-1) | (P1-1) | 2 |
| (E24) | (A24-1) | (P1-1) | 2 |
| (E25) | (A25-1) | (P1-1) | 2 |
| (E26) | (A25-2) | (P1-1) | 2 |
| (E27) | (A25-3) | (P1-1) | 2 |
| (E28) | (A25-4) | (P1-1) | 2 |
| (E29) | (A25-5) | (P1-1) | 2 |
| (E30) | (A25-6) | (P1-1) | 2 |
| (E31) | (A25-7) | (P1-1) | 2 |
| (E32) | (A25-8) | (P1-1) | 2 |
| (E33) | (A25-9) | (P1-1) | 2 |
| (E34) | (A25-10) | (P1-1) | 2 |
| (E35) | (A25-11) | (P1-1) | 2 |
| (E36) | (A26-1) | (P1-1) | 2 |
| (E37) | (A26-2) | (P1-1) | 2 |
| (E38) | (A26-3) | (P1-1) | 2 |
| (E39) | (A26-4) | (P1-1) | 2 |
| (E40) | (A26-5) | (P1-1) | 2 |
| (E41) | (A26-6) | (P1-1) | 2 |
| (E42) | (A26-7) | (P1-1) | 2 |
| (E43) | (A26-8) | (P1-1) | 2 |
| (E44) | (A26-9) | (P1-1) | 2 |
| (E45) | (A26-10) | (P1-1) | 2 |
| (E46) | (A26-11) | (P1-1) | 2 |
| (E47) | (A26-12) | (P1-1) | 2 |
| (E48) | (A26-13) | (P1-1) | 2 |
| (E49) | (A26-14) | (P1-1) | 2 |
| (E50) | (A26-15) | (P1-1) | 2 |
| (E51) | (A26-16) | (P1-1) | 2 |
| (E52) | (A26-17) | (P1-1) | 2 |
| (E53) | (A26-18) | (P1-1) | 2 |
| (E54) | (A26-19) | (P1-1) | 2 |
| (E55) | (A26-20) | (P1-1) | 2 |
| (E56) | (A26-21) | (P1-1) | 2 |
| (E57) | (A26-22) | (P1-1) | 2 |
| (E58) | (A26-23) | (P1-1) | 2 |
| (E59) | (A26-24) | (P1-1) | 2 |
| (E60) | (A30-1) | (P1-1) | 2 |
| (E61) | (A30-3) | (P1-1) | 2 |
| (E62) | (A30-5) | (P1-1) | 2 |
| (E63) | (A30-7) | (P1-1) | 2 |
| (E64) | (A30-9) | (P1-1) | 2 |
| (E65) | (A30-11) | (P1-1) | 2 |
| (E66) | (A31-1) | (P1-1) | 2 |
| (E67) | (A33-1) | (P1-1) | 2 |
| (E68) | (A33-2) | (P1-1) | 2 |
| (E69) | (A33-3) | (P1-1) | 2 |
| (E70) | (A33-4) | (P1-1) | 2 |
| (E71) | (A33-5) | (P1-1) | 2 |
| (E72) | (A34-1) | (P1-1) | 2 |

TABLE 2

| Compound | Both Ar¹ | Ph¹ | k |
|---|---|---|---|
| (E73) | (A1-1) | (P1-1) | 3 |
| (E74) | (A2-1) | (P1-1) | 3 |
| (E75) | (A3-1) | (P1-1) | 3 |
| (E76) | (A4-1) | (P1-1) | 3 |
| (E77) | (A5-1) | (P1-1) | 3 |
| (E78) | (A6-1) | (P1-1) | 3 |
| (E79) | (A7-1) | (P1-1) | 3 |
| (E80) | (A8-1) | (P1-1) | 3 |
| (E81) | (A9-1) | (P1-1) | 3 |
| (E82) | (A10-1) | (P1-1) | 3 |
| (E83) | (A11-1) | (P1-1) | 3 |
| (E84) | (A12-1) | (P1-1) | 3 |

TABLE 2-continued

| Compound | Both Ar¹ | Ph¹ | k |
|---|---|---|---|
| (E85) | (A13-1) | (P1-1) | 3 |
| (E86) | (A14-1) | (P1-1) | 3 |
| (E87) | (A15-1) | (P1-1) | 3 |
| (E88) | (A16-1) | (P1-1) | 3 |
| (E89) | (A17-1) | (P1-1) | 3 |
| (E90) | (A18-2) | (P1-1) | 3 |
| (E91) | (A19-2) | (P1-1) | 3 |
| (E92) | (A20-1) | (P1-1) | 3 |
| (E93) | (A21-1) | (P1-1) | 3 |
| (E94) | (A22-1) | (P1-1) | 3 |
| (E95) | (A23-1) | (P1-1) | 3 |
| (E96) | (A24-1) | (P1-1) | 3 |
| (E97) | (A25-1) | (P1-1) | 3 |
| (E98) | (A25-2) | (P1-1) | 3 |
| (E99) | (A25-3) | (P1-1) | 3 |
| (E100) | (A25-4) | (P1-1) | 3 |
| (E101) | (A25-5) | (P1-1) | 3 |
| (E102) | (A25-6) | (P1-1) | 3 |
| (E103) | (A25-7) | (P1-1) | 3 |
| (E104) | (A25-8) | (P1-1) | 3 |
| (E105) | (A25-9) | (P1-1) | 3 |
| (E106) | (A25-10) | (P1-1) | 3 |
| (E107) | (A25-11) | (P1-1) | 3 |
| (E108) | (A26-1) | (P1-1) | 3 |
| (E109) | (A26-2) | (P1-1) | 3 |
| (E110) | (A26-3) | (P1-1) | 3 |
| (E111) | (A26-4) | (P1-1) | 3 |
| (E112) | (A26-5) | (P1-1) | 3 |
| (E113) | (A26-6) | (P1-1) | 3 |
| (E114) | (A26-7) | (P1-1) | 3 |
| (E115) | (A26-8) | (P1-1) | 3 |
| (E116) | (A26-9) | (P1-1) | 3 |
| (E117) | (A26-10) | (P1-1) | 3 |
| (E118) | (A26-11) | (P1-1) | 3 |
| (E119) | (A26-12) | (P1-1) | 3 |
| (E120) | (A26-13) | (P1-1) | 3 |
| (E121) | (A26-14) | (P1-1) | 3 |
| (E122) | (A26-15) | (P1-1) | 3 |
| (E123) | (A26-16) | (P1-1) | 3 |
| (E124) | (A26-17) | (P1-1) | 3 |
| (E125) | (A26-18) | (P1-1) | 3 |
| (E126) | (A26-19) | (P1-1) | 3 |
| (E127) | (A26-20) | (P1-1) | 3 |
| (E128) | (A26-21) | (P1-1) | 3 |
| (E129) | (A26-22) | (P1-1) | 3 |
| (E130) | (A26-23) | (P1-1) | 3 |
| (E131) | (A26-24) | (P1-1) | 3 |
| (E132) | (A30-1) | (P1-1) | 3 |
| (E133) | (A30-3) | (P1-1) | 3 |
| (E134) | (A30-5) | (P1-1) | 3 |
| (E135) | (A30-7) | (P1-1) | 3 |
| (E136) | (A30-9) | (P1-1) | 3 |
| (E137) | (A30-11) | (P1-1) | 3 |
| (E138) | (A31-1) | (P1-1) | 3 |
| (E139) | (A33-1) | (P1-1) | 3 |
| (E140) | (A33-2) | (P1-1) | 3 |
| (E141) | (A33-3) | (P1-1) | 3 |
| (E142) | (A33-4) | (P1-1) | 3 |
| (E143) | (A33-5) | (P1-1) | 3 |
| (E144) | (A34-1) | (P1-1) | 3 |

TABLE 3

| Compound | Both Ar¹ | $R^{583}$ | Ph¹ | k |
|---|---|---|---|---|
| (E145) | (A29-3) | (N1) | (P1-1) | 2 |
| (E146) | (A29-3) | (N2) | (P1-1) | 2 |
| (E147) | (A29-3) | (N3) | (P1-1) | 2 |
| (E148) | (A29-3) | (N4) | (P1-1) | 2 |
| (E149) | (A29-3) | (N5) | (P1-1) | 2 |
| (E150) | (A29-3) | (N6) | (P1-1) | 2 |
| (E151) | (A29-3) | (N7) | (P1-1) | 2 |
| (E152) | (A29-3) | (N8) | (P1-1) | 2 |
| (E153) | (A29-3) | (N9) | (P1-1) | 2 |
| (E154) | (A29-3) | (N10) | (P1-1) | 2 |
| (E155) | (A29-3) | (N11) | (P1-1) | 2 |
| (E156) | (A29-3) | (N12) | (P1-1) | 2 |
| (E157) | (A29-3) | (N13) | (P1-1) | 2 |
| (E158) | (A29-3) | (N14) | (P1-1) | 2 |
| (E159) | (A29-3) | (N15) | (P1-1) | 2 |
| (E160) | (A29-3) | (N16) | (P1-1) | 2 |
| (E161) | (A29-3) | (N17) | (P1-1) | 2 |
| (E162) | (A29-3) | (N18) | (P1-1) | 2 |
| (E163) | (A29-3) | (N19) | (P1-1) | 2 |
| (E164) | (A29-3) | (N20) | (P1-1) | 2 |
| (E165) | (A29-3) | (N21) | (P1-1) | 2 |
| (E166) | (A29-3) | (N22) | (P1-1) | 2 |
| (E167) | (A29-3) | (N23) | (P1-1) | 2 |
| (E168) | (A29-3) | (N24) | (P1-1) | 2 |
| (E169) | (A29-3) | (N25) | (P1-1) | 2 |
| (E170) | (A29-3) | (N26) | (P1-1) | 2 |
| (E171) | (A29-3) | (N27) | (P1-1) | 2 |
| (E172) | (A29-3) | (N28) | (P1-1) | 2 |
| (E173) | (A29-3) | (N29) | (P1-1) | 2 |
| (E174) | (A29-3) | (N30) | (P1-1) | 2 |
| (E175) | (A29-3) | (N31) | (P1-1) | 2 |
| (E176) | (A29-3) | (N32) | (P1-1) | 2 |
| (E177) | (A29-3) | (N33) | (P1-1) | 2 |
| (E178) | (A29-3) | (N34) | (P1-1) | 2 |
| (E179) | (A29-3) | (N35) | (P1-1) | 2 |
| (E180) | (A29-3) | (N36) | (P1-1) | 2 |
| (E181) | (A29-3) | (N37) | (P1-1) | 2 |
| (E182) | (A29-3) | (N38) | (P1-1) | 2 |
| (E183) | (A29-3) | (N39) | (P1-1) | 2 |
| (E184) | (A29-3) | (N40) | (P1-1) | 2 |
| (E185) | (A29-3) | (N41) | (P1-1) | 2 |
| (E186) | (A29-3) | (N42) | (P1-1) | 2 |
| (E187) | (A29-3) | (N43) | (P1-1) | 2 |
| (E188) | (A29-3) | (N44) | (P1-1) | 2 |
| (E189) | (A29-3) | (N45) | (P1-1) | 2 |
| (E190) | (A29-3) | (N46) | (P1-1) | 2 |
| (E191) | (A29-3) | (N47) | (P1-1) | 2 |
| (E192) | (A29-3) | (N48) | (P1-1) | 2 |
| (E193) | (A29-3) | (N49) | (P1-1) | 2 |
| (E194) | (A29-3) | (N50) | (P1-1) | 2 |
| (E195) | (A29-3) | (N51) | (P1-1) | 2 |
| (E196) | (A29-3) | (N52) | (P1-1) | 2 |
| (E197) | (A29-3) | (N53) | (P1-1) | 2 |
| (E198) | (A29-3) | (N54) | (P1-1) | 2 |
| (E199) | (A29-3) | (N55) | (P1-1) | 2 |
| (E200) | (A29-3) | (N56) | (P1-1) | 2 |

TABLE 4

| Compound | Both Ar¹ | $R^{583}$ | Ph¹ | k |
|---|---|---|---|---|
| (E201) | (A29-3) | (N57) | (P1-1) | 2 |
| (E202) | (A29-3) | (N58) | (P1-1) | 2 |
| (E203) | (A29-3) | (N59) | (P1-1) | 2 |
| (E204) | (A29-3) | (N60) | (P1-1) | 2 |
| (E205) | (A29-3) | (N61) | (P1-1) | 2 |
| (E206) | (A29-3) | (N62) | (P1-1) | 2 |
| (E207) | (A29-3) | (N63) | (P1-1) | 2 |
| (E208) | (A29-3) | (N64) | (P1-1) | 2 |
| (E209) | (A29-3) | (N65) | (P1-1) | 2 |
| (E210) | (A29-3) | (N66) | (P1-1) | 2 |
| (E211) | (A29-3) | (N67) | (P1-1) | 2 |
| (E212) | (A29-3) | (N68) | (P1-1) | 2 |
| (E213) | (A29-3) | (N69) | (P1-1) | 2 |
| (E214) | (A29-3) | (N70) | (P1-1) | 2 |
| (E215) | (A29-3) | (N71) | (P1-1) | 2 |
| (E216) | (A29-3) | (N72) | (P1-1) | 2 |
| (E217) | (A29-3) | (N73) | (P1-1) | 2 |
| (E218) | (A29-3) | (N74) | (P1-1) | 2 |
| (E219) | (A29-3) | (N75) | (P1-1) | 2 |
| (E220) | (A29-3) | (N76) | (P1-1) | 2 |
| (E221) | (A29-3) | (N77) | (P1-1) | 2 |
| (E222) | (A29-3) | (N78) | (P1-1) | 2 |
| (E223) | (A29-3) | (N1) | (P1-1) | 3 |
| (E224) | (A29-3) | (N2) | (P1-1) | 3 |

TABLE 4-continued

| Compound | Both Ar$^1$ | R$^{583}$ | Ph$^1$ | k |
|---|---|---|---|---|
| (E225) | (A29-3) | (N3) | (P1-1) | 3 |
| (E226) | (A29-3) | (N4) | (P1-1) | 3 |
| (E227) | (A29-3) | (N5) | (P1-1) | 3 |
| (E228) | (A29-3) | (N6) | (P1-1) | 3 |
| (E229) | (A29-3) | (N7) | (P1-1) | 3 |
| (E230) | (A29-3) | (N8) | (P1-1) | 3 |
| (E231) | (A29-3) | (N9) | (P1-1) | 3 |
| (E232) | (A29-3) | (N10) | (P1-1) | 3 |
| (E233) | (A29-3) | (N11) | (P1-1) | 3 |
| (E234) | (A29-3) | (N12) | (P1-1) | 3 |
| (E235) | (A29-3) | (N13) | (P1-1) | 3 |
| (E236) | (A29-3) | (N14) | (P1-1) | 3 |
| (E237) | (A29-3) | (N15) | (P1-1) | 3 |
| (E238) | (A29-3) | (N16) | (P1-1) | 3 |
| (E239) | (A29-3) | (N17) | (P1-1) | 3 |
| (E240) | (A29-3) | (N18) | (P1-1) | 3 |
| (E241) | (A29-3) | (N19) | (P1-1) | 3 |
| (E242) | (A29-3) | (N20) | (P1-1) | 3 |
| (E243) | (A29-3) | (N21) | (P1-1) | 3 |
| (E244) | (A29-3) | (N22) | (P1-1) | 3 |
| (E245) | (A29-3) | (N23) | (P1-1) | 3 |
| (E246) | (A29-3) | (N24) | (P1-1) | 3 |
| (E247) | (A29-3) | (N25) | (P1-1) | 3 |
| (E248) | (A29-3) | (N26) | (P1-1) | 3 |
| (E249) | (A29-3) | (N27) | (P1-1) | 3 |
| (E250) | (A29-3) | (N28) | (P1-1) | 3 |
| (E251) | (A29-3) | (N29) | (P1-1) | 3 |
| (E252) | (A29-3) | (N30) | (P1-1) | 3 |
| (E253) | (A29-3) | (N31) | (P1-1) | 3 |
| (E254) | (A29-3) | (N32) | (P1-1) | 3 |
| (E255) | (A29-3) | (N33) | (P1-1) | 3 |
| (E256) | (A29-3) | (N34) | (P1-1) | 3 |

TABLE 5

| Compound | Both Ar$^1$ | R$^{583}$ | Ph$^1$ | k |
|---|---|---|---|---|
| (E257) | (A29-3) | (N35) | (P1-1) | 3 |
| (E258) | (A29-3) | (N36) | (P1-1) | 3 |
| (E259) | (A29-3) | (N37) | (P1-1) | 3 |
| (E260) | (A29-3) | (N38) | (P1-1) | 3 |
| (E261) | (A29-3) | (N39) | (P1-1) | 3 |
| (E262) | (A29-3) | (N40) | (P1-1) | 3 |
| (E263) | (A29-3) | (N41) | (P1-1) | 3 |
| (E264) | (A29-3) | (N42) | (P1-1) | 3 |
| (E265) | (A29-3) | (N43) | (P1-1) | 3 |
| (E266) | (A29-3) | (N44) | (P1-1) | 3 |
| (E267) | (A29-3) | (N45) | (P1-1) | 3 |
| (E268) | (A29-3) | (N46) | (P1-1) | 3 |
| (E269) | (A29-3) | (N47) | (P1-1) | 3 |
| (E270) | (A29-3) | (N48) | (P1-1) | 3 |
| (E271) | (A29-3) | (N49) | (P1-1) | 3 |
| (E272) | (A29-3) | (N50) | (P1-1) | 3 |
| (E273) | (A29-3) | (N51) | (P1-1) | 3 |
| (E274) | (A29-3) | (N52) | (P1-1) | 3 |
| (E275) | (A29-3) | (N53) | (P1-1) | 3 |
| (E276) | (A29-3) | (N54) | (P1-1) | 3 |
| (E277) | (A29-3) | (N55) | (P1-1) | 3 |
| (E278) | (A29-3) | (N56) | (P1-1) | 3 |
| (E279) | (A29-3) | (N57) | (P1-1) | 3 |
| (E280) | (A29-3) | (N58) | (P1-1) | 3 |
| (E281) | (A29-3) | (N59) | (P1-1) | 3 |
| (E282) | (A29-3) | (N60) | (P1-1) | 3 |
| (E283) | (A29-3) | (N61) | (P1-1) | 3 |
| (E284) | (A29-3) | (N62) | (P1-1) | 3 |
| (E285) | (A29-3) | (N63) | (P1-1) | 3 |
| (E286) | (A29-3) | (N64) | (P1-1) | 3 |
| (E287) | (A29-3) | (N65) | (P1-1) | 3 |
| (E288) | (A29-3) | (N66) | (P1-1) | 3 |
| (E289) | (A29-3) | (N67) | (P1-1) | 3 |
| (E290) | (A29-3) | (N68) | (P1-1) | 3 |
| (E291) | (A29-3) | (N69) | (P1-1) | 3 |
| (E292) | (A29-3) | (N70) | (P1-1) | 3 |
| (E293) | (A29-3) | (N71) | (P1-1) | 3 |
| (E294) | (A29-3) | (N72) | (P1-1) | 3 |

TABLE 5-continued

| Compound | Both Ar$^1$ | R$^{583}$ | Ph$^1$ | k |
|---|---|---|---|---|
| (E295) | (A29-3) | (N73) | (P1-1) | 3 |
| (E296) | (A29-3) | (N74) | (P1-1) | 3 |
| (E297) | (A29-3) | (N75) | (P1-1) | 3 |
| (E298) | (A29-3) | (N76) | (P1-1) | 3 |
| (E299) | (A29-3) | (N77) | (P1-1) | 3 |
| (E300) | (A29-3) | (N78) | (P1-1) | 3 |

The charge-transporting varnish of the invention includes a charge-transporting substance consisting of the aniline derivative of formula (1), and an organic solvent. Depending on the intended use of the resulting thin film, the varnish may include a dopant substance for the purpose of, for example, enhancing the charge transportability.

The dopant substance is not particularly limited, provided it dissolves in at least one of the solvents used in the varnish. Use can be made of either an inorganic dopant substance or an organic dopant substance.

The inorganic and organic dopant substances may be used singly or two or more may be used in combination.

Illustrative examples of the dopant substance include strong organic acids such as benzenesulfonic acid, tosylic acid, camphorsulfonic acid, hydroxybenzenesulfonic acid, 5-sulfosalicylic acid, dodecylbenzenesulfonic acid, polystyrenesulfonic acid, the 1,4-benzodioxanedisulfonic acid compounds mentioned in WO 2005/000832, the arylsulfonic acid compounds mentioned in WO 2006/025342 and the dinonylnaphthalenesulfonic acid compounds mentioned in JP-A 2005-108828; and inorganic oxidizing agents, including heteropolyacids such as phosphomolybdic acid, phosphotungstic acid and phosphotungstomolybdic acid mentioned in WO 2010/058777. These may be used in combination.

Of these, arylsulfonic acid compounds are preferred. Specific examples include benzenesulfonic acid, tosylic acid, p-styrenesulfonic acid, 2-naphthalenesulfonic acid, 4-hydroxybenzenesulfonic acid, 5-sulfosalicyclic acid, p-dodecylbenzenesulfonic acid, dihexylbenzenesulfonic acid, 2,5-dihexylbenzenesulfonic acid, dibutylnaphthalenesulfonic acid, 6,7-dibutyl-2-naphthalenesulfonic acid, dodecylnaphthalenesulfonic acid, 3-dodecyl-2-naphthalenesulfonic acid, hexylnaphthalenesulfonic acid, 4-hexyl-1-naphthalenesulfonic acid, octylnaphthalenesulfonic acid, 2-octyl-1-naphthalenesulfonic acid, hexylnaphthalenesulfonic acid, 7-hexyl-1-naphthalenesulfonic acid, 6-hexyl-2-naphthalenesulfonic acid, dinonylnaphthalenesulfonic acid, 2,7-dinonyl-4-naphthalenesulfonic acid, dinonylnaphthalenedisulfonic acid, 2,7-dinonyl-4,5-naphthalenedisulfonic acid, the 1,4-benzodioxanedisulfonic acid compounds mentioned in WO 2005/000832, the arylsulfonic acid compounds mentioned in WO 2006/025342 and the arylsulfonic acid compounds mentioned in WO 2009/096352.

Examples of arylsulfonic acid compounds that are preferred as the dopant substance in this invention include arylsulfonic acid compounds of formula (4) or (5).

[Chemical Formula 34]

$$\left( \begin{array}{c} A^2 - A^1 - A^3 \\ | \\ (SO_3H)_q \end{array} \right)_p \quad (4)$$

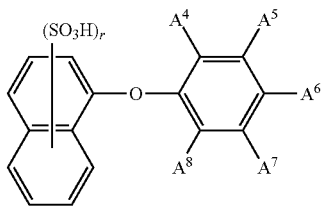

(5)

$A^1$ represents oxygen or sulfur, with oxygen being preferred.

$A^2$ represents a naphthalene ring or an anthracene ring, with a naphthalene ring being preferred.

$A^3$ represents a divalent to tetravalent perfluorobiphenyl group and the subscript p represents the number of bonds between $A^1$ and $A^3$, this being an integer that satisfies the condition $2 \leq p \leq 4$. $A^3$ is preferably a perfluorobiphenyldiyl group, especially a perfluorobiphenyl-4,4'-diyl group, and p is preferably 2.

The subscript q represents the number of sulfonic acid groups that are bonded to $A^2$, this being an integer that satisfies the condition $1 \leq q \leq 4$, and is most preferably 2.

$A^4$ to $A^8$ are each independently a hydrogen atom, a halogen atom, a cyano group, an alkyl group of 1 to 20 carbon atoms, a halogenated alkyl group of 1 to 20 carbon atoms, or a halogenated alkenyl group of 2 to 20 carbon atoms. At least three of $A^4$ to $A^8$ are halogen atoms.

Illustrative examples of halogenated alkyl groups of 1 to 20 carbon atoms include trifluoromethyl, 2,2,2-trifluoroethyl, 1,1,2,2,2-pentafluoroethyl, 3,3,3-trifluoropropyl, 2,2,3,3,3-pentafluoropropyl, 1,1,2,2,3,3,3-heptafluoropropyl, 4,4,4-trifluorobutyl, 3,3,4,4,4-pentafluorobutyl, 2,2,3,3,4,4,4-heptafluorobutyl and 1,1,2,2,3,3,4,4,4-nonafluorobutyl groups.

Illustrative examples of halogenated alkenyl groups of 2 to 20 carbon atoms include perfluorovinyl, perfluoropropenyl (allyl) and perfluorobutenyl groups.

Aside from this, the halogen atoms and alkyl groups of 1 to 20 carbon atoms are exemplified in the same way as above, although the halogen atoms are preferably fluorine atoms.

Of these, $A^4$ to $A^8$ are each preferably a hydrogen atom, a halogen atom, a cyano group, an alkyl group of 1 to 10 carbon atoms, a halogenated alkyl group of 1 to 10 carbon atoms, or a halogenated alkenyl group of 2 to 10 carbon atoms, with at least three of $A^4$ to $A^8$ being fluorine atoms; more preferably a hydrogen atom, a fluorine atom, a cyano group, an alkyl group of 1 to 5 carbon atoms, a fluorinated alkyl group of 1 to 5 carbon atoms, or a fluorinated alkenyl group of 2 to 5 carbon atoms, with at least three of $A^4$ to $A^8$ being fluorine atoms; and even more preferably a hydrogen atom, a fluorine atom, a cyano group, a perfluoroalkyl group of 1 to 5 carbon atoms, or a perfluoroalkenyl group of 1 to 5 carbon atoms, with $A^4$, $A^5$ and $A^8$ being fluorine atoms.

As used herein, "perfluoroalkyl group" refers to an alkyl group in which all the hydrogen atoms are substituted with fluorine atoms, and "perfluoroalkenyl group" refers to an alkenyl group in which all the hydrogen atoms are substituted with fluorine atoms.

The subscript r represents the number of sulfonic acid groups bonded to the naphthalene ring, this being an integer that satisfies the condition $1 \leq r \leq 4$, preferably from 2 to 4, and more preferably 2.

The molecular weight of the arylsulfonic acid compound used as a dopant substance is not particularly limited. However, taking into account the solubility in an organic solvent in cases where the arylsulfonic acid compound is used together with the aniline derivative of the invention, the molecular weight is preferably not more than 2,000, and more preferably not more than 1,500.

Examples of suitable arylsulfonic acid compounds include, but are not limited to, the following.

[Chemical Formula 35]

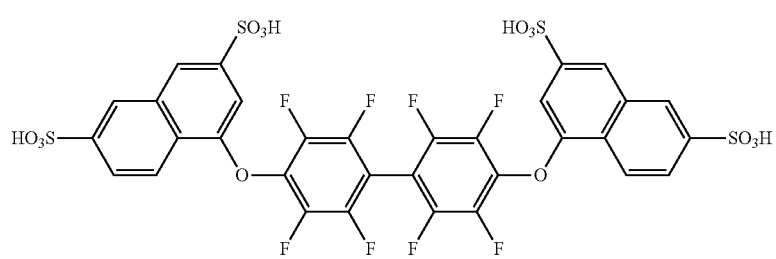

(4-1)

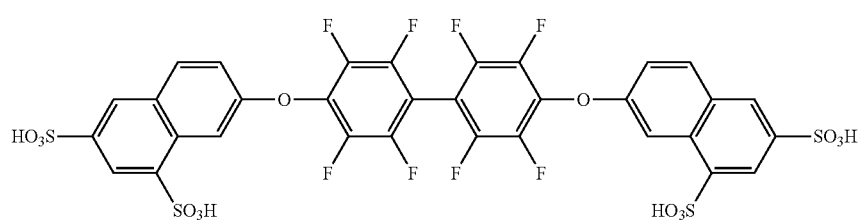

(4-2)

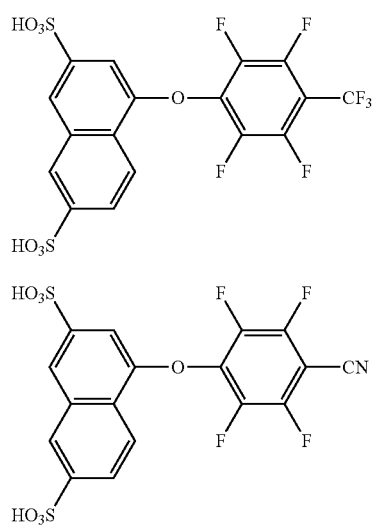

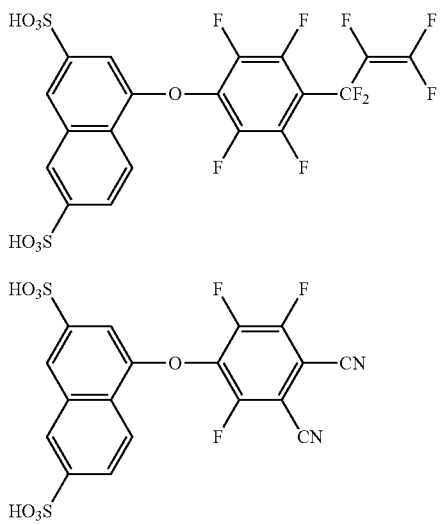

The content of arylsulfonic acid compound in the charge-transporting varnish of the invention, when expressed relative to unity (1) for the aniline derivative of formula (1), is preferably from 0.1 to 10 equivalents, more preferably from 0.5 to 5 equivalents, and even more preferably from 0.8 to 3 equivalents.

A commercial product may be used as the arylsulfonic acid compound, although it is also possible to synthesize the arylsulfonic acid compound by a known method described in, for example, WO 2006/025342 or WO 2009/096352.

In addition, when the resulting thin film is to be used as a hole-injecting layer in an organic EL device, to reproducibly obtain devices having a good longevity, it is preferable for the charge-transporting varnish of the invention to include an organosilane compound.

The organosilane compound is exemplified by dialkoxysilane compounds, trialkoxysilane compounds and tetraalkoxysilane compounds. These may be used singly, or two or more may be used in combination.

In particular, the organosilane compound is preferably a dialkoxysilane compound or a trialkoxysilane compound, and more preferably a trialkoxysilane compound.

Examples of organosilane compounds that may be used in this invention include, but are not limited to, the following.

Specific examples of dialkoxysilane compounds include dimethyldimethoxysilane, dimethyldiethoxysilane, methylethyldimethoxysilane, diethyldimethoxysilane, diethyldiethoxysilane, methylpropyldimethoxysilane, methylpropyldiethoxysilane, diisopropyldimethoxysilane, phenylmethyldimethoxysilane, vinylmethyldimethoxysilane, 3-glycidoxypropylmethyldimethoxysilane, 3-glycidoxypropylmethyldiethoxysilane, 3-(3,4-epoxycyclohexyl)ethylmethyldimethoxysilane, 3-methacryloxypropylmethyldimethoxysilane, 3-methacryloxypropylmethyldiethoxysilane, 3-mercaptopropylmethyldimethoxysilane, γ-aminopropylmethyldiethoxysilane, N-(2-aminoethyl)aminopropylmethyldimethoxysilane and 3,3,3-trifluoropropylmethyldimethoxysilane.

Specific examples of trialkoxysilane compounds include methyltrimethoxysilane, methyltriethoxysilane, ethyltrimethoxysilane, ethyltriethoxysilane, propyltrimethoxysilane, propyltriethoxysilane, butyltrimethoxysilane, butyltriethoxysilane, pentyltrimethoxysilane, pentyltriethoxysilane, heptyltrimethoxysilane, heptyltriethoxysilane, octyltrimethoxysilane, octyltriethoxysilane, dodecyltrimethoxysilane, dodecyltriethoxysilane, hexadecyltrimethoxysilane, hexadecyltriethoxysilane, octadecyltrimethoxysilane, octadecyltriethoxysilane, phenyltrimethoxysilane, phenyltriethoxysilane, vinyltrimethoxysilane, vinyltriethoxysilane, γ-aminopropyltrimethoxysilane, 3-aminopropyltriethoxysilane, γ-glycidoxypropyltrimethoxysilane, 3-glycidoxypropyltriethoxysilane, γ-methacryloxypropyltrimethoxysilane, γ-methacryloxypropyltriethoxysilane, triethoxy(4-(trifluoromethyl)phenyl)silane, dodecyltriethoxysilane, 3,3,3-trifluoropropyltrimethoxysilane, (triethoxysilyl)cyclohexane, perfluorooctylethyltriethoxysilane, triethoxyfluorosilane, tridecafluoro-1,1,2,2,-tetrahydrooctyltriethoxysilane, pentafluorophenyltrimethoxysilane, pentafluorophenyltriethoxysilane, 3-(heptafluoroisopropoxy)propyltriethoxysilane, heptadecafluoro-1,1,2,2-tetrahydrodecyltriethoxysilane, triethoxy-2-thienylsilane and 3-(triethoxysilyl)furan.

Specific examples of tetraalkoxysilane compounds include tetraethoxysilane, tetramethoxysilane and tetrapropoxysilane.

Of these, 3,3,3-trifluoropropylmethyldimethoxysilane, triethoxy(4-(trifluoromethyl)phenyl)silane, 3,3,3-trifluoropropyltrimethoxysilane, perfluorooctylethyltriethoxysilane, pentafluorophenyltrimethoxysilane and pentafluorophenyltriethoxysilane are preferred.

When the charge-transporting varnish of the invention includes an organosilane compound, the content thereof, based on the combined mass of the charge-transporting substance and the dopant substance, is generally about 0.1 to 50 mass %. However, to suppress a decrease in the charge transportability of the resulting thin film and also increase the ability to inject holes into a layer deposited so as to be in contact with the above-described hole-injecting layer on the cathode side, the content is preferably about 0.5 to 40 mass %, more preferably about 0.8 to 30 mass %, and even more preferably about 1 to 20 mass %.

In addition to a charge-transporting substance consisting of the above-described aniline derivative, the charge-transporting varnish of the invention may include also another charge-transporting substance that is known.

Highly solvating solvents which are capable of dissolving well the charge-transporting substance and the dopant substance may be used as the organic solvent employed when preparing the charge-transporting varnish.

Examples of such highly solvating solvents that may be used include, but are not limited to, organic solvents such as cyclohexanone, N,N-dimethylformamide, N,N-dimethylacetamide, N-methylpyrrolidone, 1,3-dimethyl-2-imidazolidinone and diethylene glycol monomethyl ether. These solvents may be used singly, or two or more may be used in admixture. The amount thereof may be set to from 5 to 100 mass %, based on the overall solvent used in the varnish.

The charge-transporting substance and dopant substance are preferably in a state where both are either completely dissolved or uniformly dispersed in the solvent; and are more preferably completely dissolved.

In the practice of the invention, by including in the varnish at least one high-viscosity organic solvent having a viscosity at 25° C. of 10 to 200 mPa·s, especially 35 to 150 mPa·s, and a boiling point at standard pressure (atmospheric pressure) of 50 to 300° C., especially 150 to 250° C., the viscosity of the varnish is easily adjusted, thus making it possible to prepare a varnish which reproducibly gives thin films of high flatness and is suited to the coating method to be used.

Examples of high-viscosity organic solvents include, but are not limited to, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol and hexylene glycol. These solvents may be used singly, or two or more may be used in admixture.

The amount of high-viscosity organic solvent added, as a proportion of the overall solvent used in the varnish of the invention, is preferably within a range where no precipitation of solids occurs. The amount of such addition is preferably 5 to 80 mass %, provided that no precipitation of solids occurs.

In addition, other solvents may be admixed in a proportion, with respect to the overall solvent used in the varnish, of 1 to 90 mass %, and preferably 1 to 50 mass %, for such purposes as to enhance the substrate wettability by the varnish, adjust the solvent surface tension, adjust the polarity, and adjust the boiling point.

Examples of such solvents include, but are not limited to, propylene glycol monomethyl ether, ethylene glycol monobutyl ether, diethylene glycol diethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyl lactate and n-hexyl acetate. These solvents may be used singly, or two or more may be used in admixture.

The viscosity and surface tension of the inventive varnish are set as appropriate for the thickness and other properties of the thin film to be produced and the solids concentration of the varnish while taking into account the coating method used, with the viscosity generally being from 1 to 50 mPa·s at 25° C. and the surface tension generally being from 20 to 50 mN/m.

The solids concentration of the charge-transporting varnish of this invention is set as appropriate based on such considerations as the viscosity, surface tension and other properties of the varnish and the thickness and other properties of the thin film to be produced, and is generally about 0.1 to 10.0 mass %. To improve the coating properties of the varnish, the solids concentration of the varnish is preferably about 0.5 to 5.0 mass %, and more preferably about 1.0 to 3.0 mass %.

Examples of methods for preparing the charge-transporting varnish include, but are not particularly limited to, the method of dissolving the aniline derivative of the invention in a solvent and adding thereto other ingredients such as the dopant substance, and the method of dissolving a mixture of the charge-transporting substance and the other ingredients in a solvent.

Alternatively, in cases where there are a plurality of organic solvents, first the charge-transporting substance and the like may be dissolved in a solvent that dissolves these well, and the other solvents may be added thereto, or the charge-transporting substance and the other ingredients may be successively dissolved in a mixed solvent of the plurality of organic solvents or may all be dissolved therein at the same time.

In this invention, from the standpoint of reproducibly obtaining a high-flatness thin film, it is desirable for the charge-transporting varnish to be obtained by dissolving the charge-transporting substance and other ingredients in the organic solvent and then filtering the solution using a submicron-order filter or the like.

A charge-transporting thin film can be formed on a substrate by coating the charge-transporting varnish described above onto the substrate and baking.

Examples of the varnish coating method include, but are not particularly limited to, dipping, spin coating, transfer printing, roll coating, brush coating, inkjet printing, spraying and slit coating. It is preferable for the viscosity and surface tension of the varnish to be adjusted according to the coating method.

When using the varnish of the invention, the baking atmosphere is not particularly limited. A thin film having a uniform film surface can be obtained not only in an open-air atmosphere, but even in an inert gas such as nitrogen or in a vacuum. However, from the standpoint of reproducibly obtaining a thin film having a high charge transportability, an open-air atmosphere is preferred.

The baking temperature is suitably set in the range of about 100 to 260° C. while taking into account such factors as the intended use of the resulting thin film, the degree of charge transportability to be imparted to the thin film, and the type and boiling point of the solvent. When the thin film thus obtained is to be used as a hole-injecting layer in an organic EL device, the baking temperature is preferably between about 140° C. and about 250° C., and more preferably between about 145° C. and about 240° C.

During baking, a temperature change in two or more steps may be applied for such purposes as to achieve more uniform film formability or to cause the reaction to proceed on the substrate. Heating may be carried out using a suitable apparatus such as a hot plate or an oven.

The thickness of the charge-transporting thin film is not particularly limited. However, when the thin film is to be used as a hole-injecting layer in an organic EL device, a film thickness of from 5 to 200 nm is preferred. Methods for changing the film thickness include, for example, changing the solids concentration in the varnish and changing the amount of solution on the substrate during coating.

The charge-transporting thin film of the invention can be suitably used as a hole-injecting layer in an organic EL device, although use as a charge-transporting functional layer such as a hole-injecting-and-transporting layer is also possible.

The materials and method employed to fabricate organic light-emitting diode (OLED) devices using the charge-transporting varnish of the invention are exemplified by, but not limited to, those mentioned below.

The electrode substrate to be used is preferably cleaned beforehand by liquid washing with, for example, a cleaning agent, alcohol or pure water. When the substrate is an anode substrate, it is preferably subjected to surface treatment such as UV/ozone treatment or oxygen-plasma treatment just prior to use. However, surface treatment need not be carried out if the anode material is composed primarily of organic substances.

A method of fabricating an OLED device having a hole-injecting layer consisting of a thin-film obtained from the charge-transporting varnish of the invention is described below by way of illustration.

A hole-injecting layer is formed on an electrode by coating the charge-transporting varnish of the invention onto an anode substrate and baking in the manner described above. The workpiece is then introduced into a vacuum deposition system, where a hole-transporting layer, light-emitting layer, electron-transporting layer, electron-transporting layer/hole-blocking layer and cathode metal are vapor-deposited in this order to form the OLED device. Where necessary, an electron-blocking layer may be provided between the light-emitting layer and the hole-transporting layer.

Illustrative examples of anode materials include transparent electrodes such as indium-tin oxide (ITO) and indium-zinc oxide (IZO), and metal anodes made of a metal such as aluminum or an alloy of such a metal. An anode material on which planarizing treatment has been carried out is preferred. Use can also be made of polythiophene derivatives and polyaniline derivatives having high charge transportability.

Examples of other metals making up the metal anode include, but are not limited to, scandium, titanium, vanadium, chromium, manganese, iron, cobalt, nickel, copper, zinc, gallium, yttrium, zirconium, niobium, molybdenum, ruthenium, rhodium, palladium, cadmium, indium, scandium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and alloys thereof.

Specific examples of hole-transporting layer-forming materials include triarylamines such as (triphenylamine) dimer derivatives, [(triphenylamine) dimer] spirodimer, N,N'-bis(naphthalen-1-yl)-N,N'-bis(phenyl)benzidine (α-NPD), N,N'-bis(naphthalen-2-yl)-N,N'-bis(phenyl)benzidine, N,N'-bis(3-methylphenyl)-N,N'-bis(phenyl)benzidine, N,N'-bis(3-methylphenyl)-N,N'-bis(phenyl)-9,9-spirobifluorene, N,N'-bis(naphthalen-1-yl)-N,N'-bis(phenyl)-9,9-spirobifluorene, N,N'-bis(3-methylphenyl)-N,N'-bis(phenyl)-9,9-dimethylfluorene, N,N'-bis(naphthalen-1-yl)-N,N'-bis(phenyl)-9,9-dimethylfluorene, N,N'-bis(3-methylphenyl)-N,N'-bis(phenyl)-9,9-diphenylfluorene, N,N'-bis(naphthalen-1-yl)-N,N'-bis(phenyl)-9,9-diphenylfluorene, N,N'-bis(naphthalen-1-yl)-N,N'-bis(phenyl)-2,2'-dimethylbenzidine, 2,2',7,7'-tetrakis(N,N-diphenylamino)-9,9-spirobifluorene, 9,9-bis[4-(N,N-bisbiphenyl-4-ylamino)phenyl]-9H-fluorene, 9,9-bis[4-(N,N-bisnaphthalen-2-ylamino)phenyl]-9H-fluorene, 9,9-bis[4-(N-naphthalen-1-yl-N-phe-nylamino)phenyl]-9H-fluorene, 2,2',7,7'-tetrakis[N-naphthalenyl(phenyl)amino]-9,9-spirobifluorene, N,N'-bis(phenanthren-9-yl)-N,N'-bis(phenyl)benzidine, 2,2'-bis[N,N-bis(biphenyl-4-yl)amino]-9,9-spirobifluorene, 2,2'-bis(N,N-diphenylamino)-9,9-spirobifluorene, di[4-(N,N-di(p-tolyl)amino)phenyl]cyclohexane, 2,2',7,7'-tetra(N,N-di(p-tolyl)) amino-9,9-spirobifluorene, N,N,N',N'-tetranaphthalen-2-ylbenzidine, N,N,N',N'-tetra(3-methylphenyl)-3,3'-dimethylbenzidine, N,N'-di(naphthalenyl)-N,N'-di(naphthalen-2-yl)benzidine, N,N,N',N'-tetra(naphthalenyl)benzidine, N,N'-di(naphthalen-2-yl)-N,N'-diphenylbenzidine-1-4-diamine, $N^1,N^4$-diphenyl-$N^1,N^4$-di(m-tolyl)benzene-1,4-diamine, $N^2,N^2,N^6,N^6$-tetraphenylnaphthalene-2,6-diamine, tris(4-(quinolin-8-yl)phenyl)amine, 2,2'-bis(3-(N,N-di(p-tolyl)amino)phenyl)biphenyl, 4,4',4''-tris[3-methylphenyl(phenyl)amino]triphenylamine (m-MTDATA) and 4,4',4''-tris[1-naphthyl(phenyl)amino]triphenylamine (1-TNATA); and oligothiophenes such as 5,5''-bis-{4-[bis(4-methylphenyl)amino]phenyl}-2,2':5',2''-terthiophene (BMA-3T).

Specific examples of light-emitting layer-forming materials include tris(8-quinolinolate) aluminum(III) ($Alq_3$), bis(8-quinolinolate) zinc(II) ($Znq_2$), bis(2-methyl-8-quinolinolate)-4-(p-phenylphenolate) aluminum(III) (BAlq), 4,4'-bis(2,2-diphenylvinyl)biphenyl, 9,10-di(naphthalen-2-yl)anthracene, 2-t-butyl-9,10-di(naphthalen-2-yl)anthracene, 2,7-bis[9,9-di(4-methylphenyl)fluoren-2-yl]-9,9-di(4-methylphenyl)fluorene, 2-methyl-9,10-bis(naphthalen-2-yl)anthracene, 2-(9,9-spirobifluoren-2-yl)-9,9-spirobifluorene, 2,7-bis(9,9-spirobifluoren-2-yl)-9,9-spirobifluorene, 2-[9,9-di(4-methylphenyl)fluoren-2-yl]-9,9-di(4-methylphenyl)fluorene, 2,2'-dipyrenyl-9,9-spirobifluorene, 1,3,5-tris(pyren-1-yl)benzene, 9,9-bis[4-(pyrenyl)phenyl]-9H-fluorene, 2,2'-bi(9,10-diphenylanthracene), 2,7-dipyrenyl-9,9-spirobifluorene, 1,4-di(pyren-1-yl)benzene, 1,3-di(pyren-1-yl)benzene, 6,13-di(biphenyl-4-yl)pentacene, 3,9-di(naphthalen-2-yl)perylene, 3,10-di(naphthalen-2-yl)perylene, tris[4-(pyrenyl)phenyl]amine, 10,10'-di(biphenyl-4-yl)-9,9'-bianthracene, N,N'-di(naphthalen-1-yl)-N,N'-diphenyl[1,1':4',1'':4'',1'''-quaterphenyl]-4,4'''-diamine, 4,4'-di[10-(naphthalen-1-yl)anthracen-9-yl]biphenyl, dibenzo{[f,f']-4,4',7,7'-tetraphenyl}diindeno[1,2,3-cd:1',2',3'-lm]perylene, 1-(7-(9,9'-bianthracen-10-yl)-9,9-dimethyl-9H-fluoren-2-yl)pyrene, 1-(7-(9,9'-bianthracen-10-yl)-9,9-dihexyl-9H-fluoren-2-yl)pyrene, 1,3-bis(carbazol-9-yl)benzene, 1,3,5-tris(carbazol-9-yl)benzene, 4,4',4''-tris(carbazol-9-yl)triphenylamine, 4,4'-bis(carbazol-9-yl)biphenyl (CBP), 4,4'-bis(carbazol-9-yl)-2,2'-dimethylbiphenyl, 2,7-bis(carbazol-9-yl)-9,9-dimethylfluorene, 2,2',7,7'-tetrakis(carbazol-9-yl)-9,9-spirobifluorene, 2,7-bis(carbazol-9-yl)-9,9-di(p-tolyl)fluorene, 9,9-bis[4-(carbazol-9-yl)phenyl]fluorene, 2,7-bis(carbazol-9-yl)-9,9-spirobifluorene, 1,4-bis(triphenylsilyl)benzene, 1,3-bis(triphenylsilyl)benzene, bis(4-N,N-diethylamino 2-methylphenyl)-4-methylphenylmethane, 2,7-bis(carbazol-9-yl)-9,9-dioctylfluorene, 4,4''-di(triphenylsilyl)-p-terphenyl, 4,4'-di(triphenylsilyl)biphenyl, 9-(4-t-butylphenyl)-3,6-bis(triphenylsilyl)-9H-carbazole, 9-(4-t-butylphenyl)-3,6-ditrityl-9H-carbazole, 9-(4-t-butylphenyl)-3,6-bis(9-(4-methoxyphenyl)-9H-fluoren-9-yl)-9H-carbazole, 2,6-bis(3-(9H-carbazol-9-yl)phenyl)pyridine, triphenyl(4-(9-phenyl-9H-fluoren-9-yl)phenyl)silane, 9,9-dimethyl-N,N-diphenyl-7-(4-(1-phenyl-1H-benzo[d]imidazol-2-yl)phenyl-9H-fluoren-2-amine, 3,5-bis(3-(9H-carbazol-9-yl)phenyl)pyridine, 9,9-spirobifluoren-2-yldiphenylphosphine oxide, 9,9'-(5-triphenylsilyl)-1,3-phenylene)bis(9H-carbazole), 3-(2,7-bis(diphenylphosphoryl)-9-phenyl-9H-fluoren-9-yl)-9-phenyl-9H-carbazole, 4,4,8,8,12,12-hexa(p-tolyl)-4H-8H-12H-12C-azadibenzo[cd,mn]pyrene, 4,7-di(9H-carbazol-9-yl)-1,10-phenanthroline, 2,2'-bis(4-(carbazol-9-yl)phenyl)

biphenyl, 2,8-bis(diphenylphosphoryl)dibenzo[b,d]thiophene, bis(2-methylphenyl)diphenylsilane, bis[3,5-di(9H-carbazol-9-yl)phenyl]diphenylsilane, 3,6-bis(carbazol-9-yl)-9-(2-ethylhexyl)-9H-carbazole, 3-(diphenylphosphoryl)-9-(4-(diphenylphosphoryl)phenyl)-9H-carbazole and 3,6-bis[(3,5-diphenyl)phenyl]-9-phenylcarbazole. The light-emitting layer may be formed by co-deposition of any of these materials with a light-emitting dopant.

Specific examples of light-emitting dopants include 3-(2-benzothiazolyl)-7-(diethylamino)coumarin, 2,3,6,7-tetrahydro-1,1,7,7-tetramethyl-1H,5H,11H-10-(2-benzothiazolyl)quinolidino-[9,9a,1gh]coumarin, quinacridone, N,N'-dimethylquinacridone, tris(2-phenylpyridine) iridium(III) (Ir(ppy)$_3$), bis(2-phenylpyridine)(acetylacetonate) iridium (III) (Ir(ppy)$_2$(acac)), tris[2-(p-tolyl)pyridine] iridium(III) (Ir(mppy)$_3$), 9,10-bis[N,N-di(p-tolyl)amino]anthracene, 9,10-bis[phenyl(m-tolyl)amino]anthracene, bis[2-(2-hydroxyphenyl)benzothiazolate] zinc(II), $N^{10},N^{10},N^{10'},N^{10'}$-tetra(p-tolyl)-9,9'-bianthracene-10,10'-diamine, $N^{10},N^{10},N^{10'},N^{10'}$-tetraphenyl-9,9'-bianthracene-10,10'-diamine, $N^{10},N^{10'}$-diphenyl-$N^{10},N^{10'}$-dinaphthalenyl-9,9'-bianthracen-10,10'-diamine, 4,4'-bis(9-ethyl-3-carbazovinylene)-1,1'-biphenyl, perylene, 2,5,8,11-tetra-t-butylperylene, 1,4-bis[2-(3-N-ethylcarbazolyl)vinyl]benzene, 4,4'-bis[4-(di-p-tolylamino)styryl]biphenyl, 4-(di-p-tolylamino)-4'-[(di-p-tolylamino)styryl]stilbene, bis[3,5-difluoro-2-(2-pyridyl)phenyl-(2-carboxypyridyl)] iridium(III), 4,4'-bis[4-(diphenylamino)styryl]biphenyl, bis(2,4-difluorophenylpyridinato)tetrakis(1-pyrazolyl)borate iridium(III), N,N'-bis(naphthalen-2-yl)-N,N'-bis(phenyl)tris(9,9-dimethylfluorenylene), 2,7-bis{2-[phenyl(m-tolyl)amino]-9,9-dimethylfluoren-7-yl}-9,9-dimethylfluorene, N-(4-((E)-2-(6((E)-4-(diphenylamino)styryl)naphthalen-2-yl)vinyl)phenyl)-N phenylbenzenamine, fac-iridium(III) tris(1-phenyl-3-methylbenzimidazolin-2-ylidene-C,C$^{2'}$), mer-iridium(III) tris(1-phenyl-3-methylbenzimidazolin-2-ylidene-C,C$^{2'}$), 2,7-bis[4-(diphenylamino)styryl]-9,9-spirobifluorene, 6-methyl-2-(4-(9-(4-(6-methylbenzo[d]thiazol-2-yl)phenyl)anthracen-10-yl)phenyl)-benzo[d]thiazole, 1,4-di[4-(N,N-diphenyl)amino]styrylbenzene, 1,4-bis(4 (9H-carbazol-9-yl)styryl)benzene, (E)-6-(4-(diphenylamino)styryl)-N,N-diphenylnaphthalene-2-amine, bis(2,4-difluorophenylpyridinato)(5-(pyridin-2-yl)-1H-tetrazolate) iridium(III), bis(3-trifluoromethyl-5-(2-pyridyl)pyrazole)(2,4-difluorobenzyl)diphenylphosphinate) iridium (III), bis(3-trifluoromethyl-5-(2-pyridyl)pyrazolate)(benzyldiphenylphosphinate) iridium(III), bis(1-(2,4-difluorobenzyl)-3-methylbenzimidazolium)(3-(trifluoromethyl)-5-(2-pyridyl)-1,2,4-triazolate) iridium(III), bis(3-trifluoromethyl-5-(2-pyridyl)pyrazolate)(4',6'-difluorophenylpyridinate) iridium(III), bis(4',6'-diflu- orophenylpyridinato)(3,5-bis(trifluoromethyl)-2-(2'-pyridyl)pyrrolate) iridium(III), bis(4',6'-difluorophenylpyridinato)(3-(trifluoromethyl)-5-(2-pyridyl)-1,2,4-triazolate) iridium (III), (Z)-6-mesityl-N-(6 mesitylquinoline-2(1H)-ylidene)quinoline-2-amine-BF$_2$, (E)-2-(2-(4-(dimethylamino)styryl)-6-methyl-4H-pyran-4-ylidene)malononitrile, 4-(dicyanomethylene)-2-methyl-6-julolidyl-9-enyl-4-H-pyran, 4-(dicyanomethylene)-2-methyl-6-(1,1,7,7-tetramethyljulolidyl-9-enyl)-4H-pyran, 4-(dicyanomethylene)-2-t-butyl-6-(1,1,7,7-tetramethyljulolidin-4-ylvinyl)-4H-pyran, tris (dibenzoylmethane)phenanthroline europium(II), 5,6,11,12-tetraphenylnaphthacene, bis(2-benzo[b]thiophen-2-yl-pyridine)(acetylacetonate) iridium(III), tris(1-phenylisoquinoline) iridium(III), bis(1-phenylisoquinoline) (acetylacetonate) iridium(III), bis[1-(9,9-dimethyl-9H-fluoren-2-yl)isoquinoline](acetylacetonate) iridium(III), bis[2-(9,9-dimethyl-9H-fluoren-2-yl)quinoline](acetylacetonate) iridium(III), tris[4,4'-di-t-butyl-(2,2')-bipyridine] ruthenium(III) bis(hexafluorophosphate), tris(2-phenylquinoline) iridium(III), bis(2-phenylquinoline) (acetylacetonate) iridium(III), 2,8-di-t-butyl-5,11-bis(4-t-butylphenyl)-6,12-diphenyltetrazene, bis(2-phenyl-benzothiazolate)(acetylacetonate) iridium(III), platinum 5,10,15,20-tetraphenyltetrabenzoporphyrin, osmium(II) bis (3-trifluoromethyl-5-(2-pyridine)pyrazolate)dimethylphenylphosphine, osmium(II) bis(3-trifluoromethyl)-5-(4-t-butylpyridyl)-1,2,4-triazolate)diphenylmethylphosphine, osmium(II) bis(3-(trifluoromethyl)-5-(2-pyridyl)-1,2,4-triazole)dimethylphenylphosphine, osmium(II) bis(3-(trifluoromethyl)-5-(4-t-butylpyridyl)-1,2,4-triazolate)dimethylphenylphosphine, bis[2-(4-n-hexylphenyl)quinoline] (acetylacetonate) iridium(III), tris[2-(4-n-hexylphenyl)quinoline] iridium(III), tris[2-phenyl-4-methylquinoline] iridium(III), bis(2-phenylquinoline)(2-(3-methylphenyl) pyridinate) iridium(III), bis-(2-(9,9-diethylfluoren-2-yl)-1-phenyl-1H-benzo[d]imidazolato)(acetylacetonate) iridium (III), bis(2-phenylpyridine)(3-(pyridin-2-yl)-2H-chromen-9-onate) iridium(III), bis(2-phenylquinoline)(2,2,6,6-tetramethylheptane-3,5-dionate) iridium(III), bis (phenylisoquinoline)(2,2,6,6-tetramethylheptane-3,5-dionate) iridium(III), iridium(III) bis(4-phenylthieno[3,2-c] pyridinato-N,C$^{2'}$)acetylacetonate, (E)-2-(2-t-butyl-6-(2-(2,6,6-trimethyl-2,4,5,6-tetrahydro-1H-pyrrolo[3,2,1-ij]
quinolin-8 yl)vinyl)-4H-pyran-4-ylidene)malononitrile, bis (3-trifluromethyl-5-(1-isoquinolyl)pyrazolate)(methyldiphenylphosphine) ruthenium, bis[(4-n-hexylphenyl)isoquinoline](acetylacetonate) iridium(III), platinum(II) octaethylporphin, bis(2-methyldibenzo[f,h]quinoxaline)(acetylacetonate) iridium(III) and tris[(4-n-hexylphenyl) isoquinoline] iridium(III).

Specific examples of electron-transporting layer-forming materials include lithium 8-hydroxyquinolinate, 2,2',2''-(1,3,5-benzenetriyl)-tris(1-phenyl-1-H-benzimidazole), 2-(4-biphenyl)-5-(4-t-butylphenyl)-1,3,4-oxadiazol, 2,9-dimethyl-4,7-diphenyl-1,10-phenanthroline, 4,7-diphenyl-1,10-phenanthroline, bis(2-methyl-8-quinolinolate)-4-(phenylphenolato)aluminum, 1,3-bis[2-(2,2'-bipyridin-6-yl)-1,34-oxadiazo-5-yl]benzene, 6,6'-bis[5-(biphenyl-4-yl)-1,3,4-oxadiazo-2-yl]-2,2'-bipyridine, 3-(4-biphenyl)-4-phenyl-5-t-butylphenyl-1,2,4-triazole, 4-(naphthalen-1-yl)-3,5-diphenyl-4H-1,2,4-triazole, 2,9-bis(naphthalen-2-yl)-4,7-diphenyl-1,10-phenanthroline, 2,7-bis[2-(2,2'-bipyridin-6-yl)-1,3,4-oxadiazo-5-yl]-9,9-dimethylfluorene, 1,3-bis[2-(4-t-butylphenyl)-1,3,4-oxadiazo-5-yl]benzene, tris(2,4,6-trimethyl-3-(pyridin-3-yl)phenyl)borane, 1-methyl-2-(4-(naphthalen-2-yl)phenyl)-1H-imidazo[4,5f][1,10]
phenanthroline, 2-(naphthalen-2-yl)-4,7-diphenyl-1,10-phenanthroline, phenyldipyrenylphosphine oxide, 3,3',5,5'-tetra[(m-pyridyl)phen-3-yl]biphenyl, 1,3,5-tris[(3-pyridyl) phen-3-yl]benzene, 4,4'-bis(4,6-diphenyl-1,3,5-triazin-2-yl) biphenyl, 1,3-bis[3,5-di(pyridin-3-yl)phenyl]benzene, bis (10-hydroxybenzo[h]quinolinato)beryllium, diphenylbis(4-(pyridin-3-yl)phenyl)silane and 3,5-di(pyren-1-yl)pyridine.

Examples of electron-injecting layer-forming materials include lithium oxide (Li$_2$O), magnesium oxide (MgO), alumina (Al$_2$O$_3$), lithium fluoride (LiF), sodium fluoride (NaF), magnesium fluoride (MgF$_2$), cesium fluoride (CsF), strontium fluoride (SrF$_2$), molybdenum trioxide (MoO$_3$), aluminum, Li(acac), lithium acetate and lithium benzoate.

Examples of cathode materials include aluminum, magnesium-silver alloys, aluminum-lithium alloys, lithium, sodium, potassium and cesium.

Another example of a method for fabricating an organic EL device having a hole-injecting layer consisting of a thin film obtained from the charge-transporting varnish of the invention is as follows.

An organic EL device having a charge-transporting thin-film formed using the charge-transporting varnish of the invention can be fabricated by, in the production of an EL device as described above, successively forming a hole-transporting layer (referred to below as a "hole-transporting polymer layer") and a light-emitting layer (referred to below as a "light-transmitting polymer layer") instead of carrying out vacuum deposition operations for a hole-transporting layer, a light-emitting layer, an electron-transporting layer and an electron-injecting layer.

Specifically, the charge-transporting varnish of the invention is coated onto an anode substrate, thus forming a hole-injecting layer by the above-described method. A hole-transporting polymer layer and a light-emitting polymer layer are then successively formed thereon, following which a cathode is vapor-deposited on top, thereby forming the organic EL device.

The cathode and anode materials used here may be similar to those mentioned above, and similar cleaning treatment and surface treatment may be carried out.

The method of forming the hole-transporting polymer layer and the light-emitting polymer layer is exemplified by a film-forming method in which a solvent is added to a hole-transporting polymer material or a light-emitting polymer material, or to the material obtained by adding to these a dopant substance, thereby dissolving or uniformly dispersing the material, following which the resulting solution or dispersion is coated onto the hole-injecting layer or hole-transporting polymer layer and subsequently baked.

Examples of hole-transporting polymer materials include poly[(9,9-dihexylfluorenyl-2,7-diyl)-co-(N,N'-bis{p-butylphenyl}-1,4-diaminophenylene)], poly[(9,9-dioctylfluorenyl-2,7-diyl)-co-(N,N'-bis{p-butylphenyl}-1,1'-biphenylene-4,4-diamine)], poly[(9,9-bis{1'-penten-5'-yl}fluorenyl-2,7-diyl)-co-(N,N'-bis{p-butylphenyl}-1,4-diaminophenylene)], poly[N,N'-bis(4-butylphenyl)-N,N'-bis(phenyl)benzidine] end-capped with polysilsesquioxane and poly[(9,9-dioctylfluorenyl-2,7-diyl)-co-(4,4'-(N-(p-butylphenyl))diphenylamine)].

Examples of light-emitting polymer materials include polyfluorene derivatives such as poly(9,9-dialkylfluorene) (PDAF), poly(phenylene vinylene) derivatives such as poly(2-methoxy-5-(2'-ethylhexoxy)-1,4-phenylene vinylene) (MEH-PPV), polythiophene derivatives such as poly(3-alkylthiophene) (PAT), and polyvinylcarbazole (PVCz).

Examples of the solvent include toluene, xylene and chloroform. Examples of the method of dissolution or uniform dispersion include stirring, stirring under applied heat, and ultrasonic dispersion.

Examples of the coating method include, but are not particularly limited to, inkjet printing, spraying, dipping, spin coating, transfer printing, roll coating and brush coating. Coating is preferably carried out in an inert gas atmosphere such as nitrogen or argon.

Examples of the baking method include methods that involve heating in an oven or on a hot plate, either in an inert gas atmosphere or in a vacuum.

A hole-blocking layer, an electron-blocking layer or the like may be optionally provided between the electrodes and any of the above layers. By way of illustration, an example of a material that forms an electron-blocking layer is tris(phenylpyrazole)iridium.

The materials which make up the layers that form the anode, the cathode and the layers formed therebetween differ according to whether a device provided with a bottom emission structure or a top emission structure is to be fabricated, and so are suitably selected while taking this into account.

Generally, in a device having a bottom emission structure, a transparent anode is used on the substrate side and light is extracted from the substrate side, whereas in a device having a top emission structure, a reflective anode made of metal is used and light is extracted from a transparent electrode (cathode) side in the opposite direction from the substrate. Accordingly, with regard to, for example, the anode material, when fabricating a device having a bottom emission structure, a transparent anode of (ITO) or the like is used, and when fabricating a device having a top emission structure, a reflective anode of Al/Nd or the like is used.

To prevent a deterioration in device characteristics, the organic EL device of the invention may be sealed in the usual manner with, if necessary, a desiccant or the like.

EXAMPLES

Production Examples and Working Examples are given below to more concretely illustrate the invention, although the invention is not limited by these Examples. The equipment used was as follows.

(1) MALDI-TOF-MS: Autoflex III SmartBeam, from Bruker Daltonics (2) $^1$H-NMR: JNM-ECP-300FT NMR system, from JEOL Ltd.

(3) Substrate Cleaning: Substrate cleaning machine (reduced-pressure plasma system), from Choshu Industry Co., Ltd.

(4) Varnish Coating: MS-A100 Spin Coater, from Mikasa Co., Ltd.

(5) Film Thickness Measurement: Surfcorder ET-4000 microfigure measuring instrument, from Kosaka Laboratory, Ltd.

(6) EL Device Fabrication: C-E2L1G1-N Multifunction Vapor Deposition System, from Choshu Industry Co., Ltd.

(7) Measurement of Brightness, etc. of EL Device: I-V-L Measurement System from Tech World, Inc.

(8) Measurement of EL Device Longevity (Measurement of Brightness Half-Life): PEL-105S EL Brightness Life Evaluation System, from EHC K.K.

[1] Compound Synthesis

[Synthesis Example 1] Synthesis of N1-(Phenanthren-9-yl)-N4-(4-(phenanthren-9-ylamino)phenyl)benzene-1,4-diamine

[Chemical Formula 36]

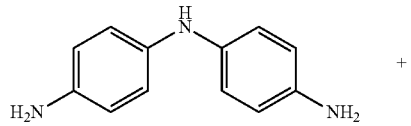

-continued

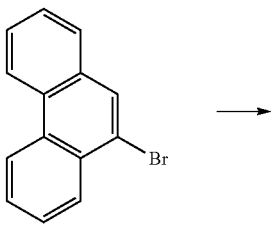

[Chemical Formula 37]

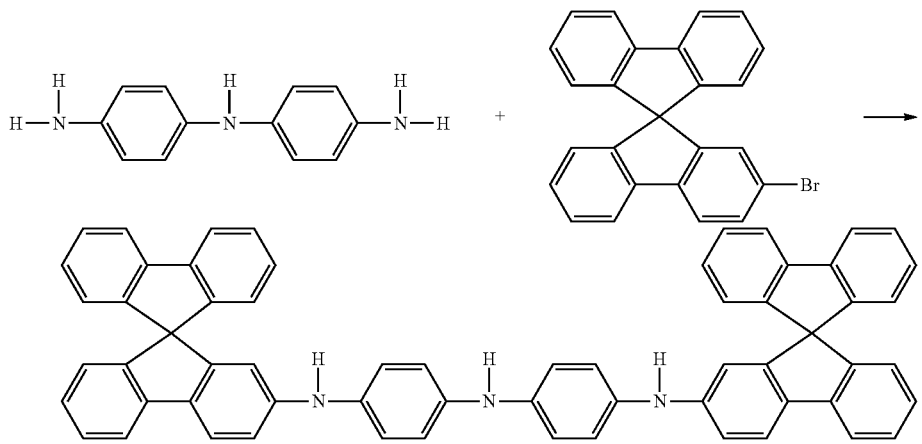

-continued

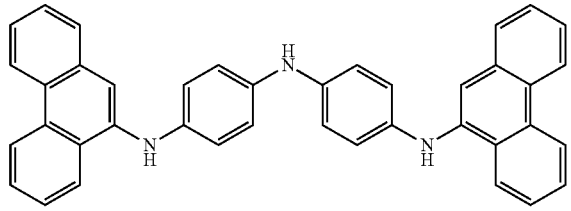

A reactor was charged with 2.01 g of N1-(4-aminophenyl)benzene-1,4-diamine, 5.68 g of 9-bromophenanthrene, 0.46 g of Pd(PPh$_3$)$_4$ and 2.32 g of sodium tert-butoxide and the interior of the reactor was flushed with nitrogen, following which 50 mL of xylene was added and the mixture was stirred for 5 hours under heating and refluxing conditions, thereby effecting the reaction. The reaction mixture was cooled to room temperature, after which toluene and saturated saline were added, and the insoluble matter that formed was filtered off. The filtered matter was washed in turn with deionized water, methanol and toluene. After being washed, the filtered matter was dissolved in tetrahydrofuran (THF), activated carbon was added to the solution, and the system was stirred for 1 hour at 50° C. The activated carbon was removed by filtration, and the resulting filtrate was concentrated and dried, giving 3.48 g (yield, 63%) of the target N1-(phenanthren-9-yl)-N4-(4-(phenanthren-9-ylamino)phenyl)benzene-1,4-diamine (Aniline Derivative 1).

$^1$H-NMR (300 MHz, DMSO-d6) δ [ppm]:
8.83 (d, J=8.9 Hz, 2H), 8.67 (d, J=8.9 Hz, 2H), 8.41 (d, J=7.7 Hz, 2H), 7.97 (s, 2H), 7.87 (s, 1H), 7.65-7.76 (m, 6H), 7.39-7.50 (m, 4H), 7.24 (s, 2H), 7.17 (d, J=8.9 Hz, 4H), 7.10 (d, J=8.9 Hz, 4H).

[Synthesis Example 2] Synthesis of N1-(9,9'-Spirobi[fluoren]-2-yl)-N4-(4-(9,9'-spirobi[fluoren]-2-ylamino)phenyl)benzene-1,4-diamine A flask was charged with 0.500 g of bis(4-aminophenyl)amine, 2.18 g of 2-bromo-9,9'-spirobi[fluorene], 0.117 g of Pd(PPh$_3$)$_4$ and 0.579 g of sodium tert-butoxide, following which the interior of the reactor was flushed with nitrogen. To this was added 20 mL of xylene, and the flask contents were stirred for 5 hours under heating and refluxing conditions.

Next, the reaction mixture was cooled to room temperature, following which the cooled reaction mixture, toluene and deionized water were mixed together and separatory treatment was carried out. The organic layer thus obtained was washed with deionized water, and was additionally washed with saturated saline.

Next, the washed organic layer was dried over sodium sulfate and then concentrated. Silica gel column chromatography (developing solvent: toluene) was carried out on the concentrated liquid and, using thin-layer chromatography (TLC) to check for the presence of the target substance, the fractions containing the target substance were collected.

Lastly, the solvent was removed under reduced pressure from the collected fractions, giving 0.926 g (yield, 46%) of the target N1-(9,9'-spirobi[fluoren]-2-yl)-N4-(4-(9,9'-spirobi[fluoren]-2-ylamino)phenyl)benzene-1,4-diamine (Aniline Derivative 2).

MALDI-TOF-MS, m/Z; found: 826.45 ([M]$^+$ calculated: 827.33).

[Synthesis Example 3] Synthesis of N1-(Naphthalen-1-yl)-N4-(4-((4-naphthalen-1-yl(phenyl)amino)phenylamino)phenylamino)phenyl)-N1-phenylbenzene-1,4-diamine

[Chemical Formula 38]

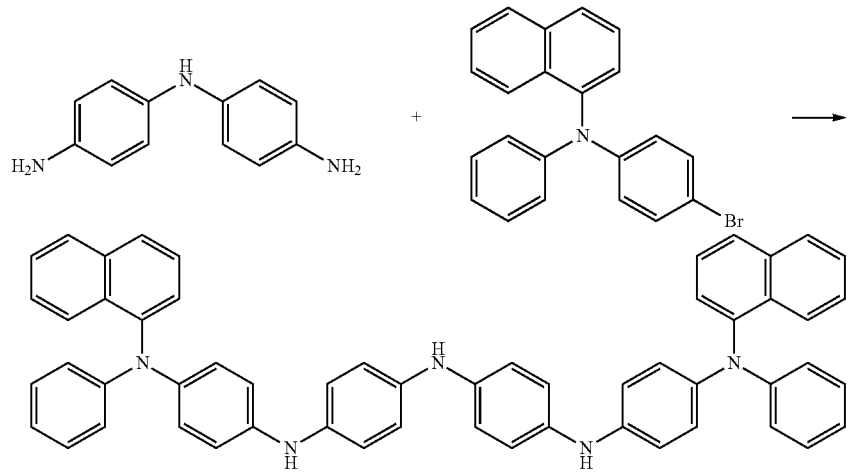

A flask was charged with 1.59 g of bis(4-aminophenyl)amine, 6.29 g of N-(4-bromophenyl)-N-phenylnaphthalen-1-amine, 0.373 g of Pd(PPh$_3$)$_4$ and 1.84 g of sodium tert-butoxide, following which the interior of the flask was flushed with nitrogen. To this was added 100 mL of xylene, and the flask contents were stirred for 4.5 hours under heating and refluxing conditions.

After the completion of stirring, the reaction mixture was cooled to room temperature, following which the cooled reaction mixture, ethyl acetate and deionized water were mixed together and separatory treatment was carried out. The organic layer thus obtained was washed in turn with deionized water and saturated saline, and then dried over magnesium sulfate. The organic phase was then filtered and the solvent was driven off under reduced pressure, following which separation and purification were carried out by silica gel column chromatography (developing solvent: chloroform/ethyl acetate=100/0→0/100). The fractions containing the target substance were collected and the solvent was driven off under reduced pressure, following which recrystallization was carried out in 1,4-dioxane/ethanol. Lastly, the crystals were filtered off, and the resulting filtered matter was dried, giving 0.994 g (yield, 16%) of N1-(naphthalen-1-yl)-N4-(4-((4-naphthalen-1-yl(phenyl)amino)-phenylamino)phenylamino)phenyl)-N1-phenylbenzene-1,4-diamine (Aniline Derivative 3).

$^1$H-NMR (400 MHz, THF-d8) δ [ppm]: 7.97 (d, J=8.4 Hz, 2H), 7.85 (d, J=8.0 Hz, 2H), 7.71 (d, J=8.0 Hz, 2H), 7.38-7.44 (m, 4H), 7.25-7.33 (m, 4H), 6.73-7.07 (m, 29H).

MALDI-TOF-MS, m/Z; found: 785.00 ([M]$^+$ calculated: 785.35).

[Synthesis Example 4] Synthesis of N1-(9-Phenyl-9H-carbazol-3-yl)-N4-(4-((9-phenyl-9H-carbazol-3-yl)amino)phenyl)benzene-1,4-diamine

[Chemical Formula 39]

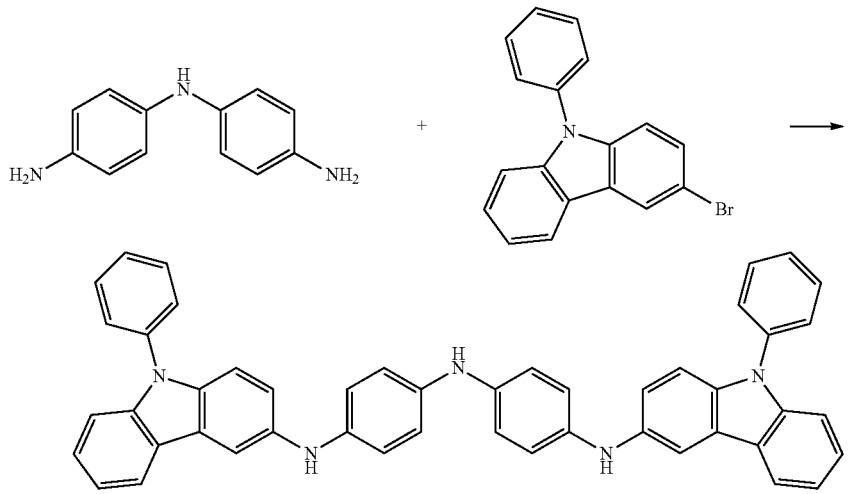

A flask was charged with 3.18 g of bis(4-aminophenyl)amine, 11.3 g of 3-bromo-9-phenyl-9H-carbazole, 0.183 g of Pd(dba)$_2$ and 3.39 g of sodium tert-butoxide, following which the interior of the flask was flushed with nitrogen. Next, 200 mL of toluene and 1.45 mL of a toluene solution of di-t-butyl(phenyl)phosphine prepared beforehand (concentration, 98 g/L) were added and the flask contents were stirred at 50° C. After 2 hours, the temperature was raised to 80° C., and the flask contents were stirred again for 3 hours. Following the completion of stirring, the reaction mixture was cooled to room temperature and filtered. The solvent in the filtrate was driven off under reduced pressure, following which separation and purification were carried out by silica gel column chromatography (developing solvent: toluene/ethyl acetate=100/0→70/30). The fractions containing the target substance were collected and the solvent was driven off under reduced pressure. This was then dissolved in THF, the solution was added dropwise to methanol being stirred, and the resulting slurry was further stirred at room temperature. Lastly, the slurry was filtered and the filtered matter was dried, giving 5.14 g (yield, 47%) of N1-(9-phenyl-9H-carbazol-3-yl)-N4-(4-((9-phenyl-9H-carbazol-3-yl)amino)phenyl)-benzene-1,4-diamine (Aniline Derivative 4).

$^1$H-NMR (400 MHz, DMSO-d6) δ[ppm]: 8.12-8.14 (m, 2H), 7.81 (d, J=1.6 Hz, 2H), 7.49-7.74 (m, 13H), 7.37-7.39 (m, 4H), 7.30 (d, J=8.8 Hz, 2H), 7.19-7.23 (m, 2H), 7.14 (dd, J=8.8, 2.0 Hz, 2H), 6.96-7.04 (m, 8H).

MALDI-TOF-MS, m/Z; found: 681.04 ([M]$^+$ calculated: 681.29).

[2] Preparation of Charge-Transporting Varnishes

Working Example 1-1

A charge-transporting varnish was prepared by dissolving 0.105 g of Aniline Derivative 1 as the charge-transporting substance and 0.139 g of the arylsulfonic acid compound of formula (4-1) above synthesized in accordance with the method described in WO 2006/025342 as the dopant substance in 4.0 g of 1,3-dimethyl-2-imidazolidinone (DMI), and then further adding 6.0 g of cyclohexanol and 2.0 g of propylene glycol and stirring.

Working Example 1-2

A charge-transporting varnish was prepared by dissolving 0.088 g of Aniline Derivative 1 as the charge-transporting substance and 0.116 g of the arylsulfonic acid compound of formula (4-1) in 3.3 g of DMI, and then further adding 4.0 g of 2,3-butanediol (2,3-BD) and 2.7 g of dipropylene glycol monomethyl ether (DPM) and stirring.

Working Example 1-3

Aside from changing the amounts in which Aniline Derivative 1 and the arylsulfonic acid compound of formula (4-1) were used to respectively 0.068 g and 0.136 g, a charge-transporting varnish was prepared in the same way as in Working Example 1-2.

Working Example 1-4

Aside from changing the amounts in which Aniline Derivative 1 and the arylsulfonic acid compound of formula (4-1) were used to respectively 0.058 g and 0.148 g, a charge-transporting varnish was prepared in the same way as in Working Example 1-2.

Working Example 1-5

Aside from using 0.135 g of Aniline Derivative 2 and 0.110 g of the arylsulfonic acid compound of formula (4-1), a charge-transporting varnish was prepared in the same way as in Working Example 1-1.

Working Example 1-6

Aside from using 0.112 g of Aniline Derivative 2 and 0.092 g of the arylsulfonic acid compound of formula (4-1), a charge-transporting varnish was prepared in the same way as in Working Example 1-2.

Working Example 1-7

Aside from using 0.092 g of Aniline Derivative 2 and 0.112 g of the arylsulfonic acid compound of formula (4-1), a charge-transporting varnish was prepared in the same way as in Working Example 1-2.

Working Example 1-8

Aside from using 0.075 g of Aniline Derivative 3 and 0.129 g of the arylsulfonic acid compound of formula (4-1), a charge-transporting varnish was prepared in the same way as in Working Example 1-2.

Working Example 1-9

Aside from using 0.065 g of Aniline Derivative 3 and 0.139 g of the arylsulfonic acid compound of formula (4-1), a charge-transporting varnish was prepared in the same way as in Working Example 1-2.

Working Example 1-10

Aside from using 0.057 g of Aniline Derivative 3 and 0.147 g of the arylsulfonic acid compound of formula (4-1), a charge-transporting varnish was prepared in the same way as in Working Example 1-2.

Working Example 1-11

A charge-transporting varnish was prepared by dissolving 0.137 g of Aniline Derivative 4 and 0.271 g of the arylsulfonic acid compound of formula (4-1) in 6.6 g of DMI, and then further adding 8.0 g of 2,3-BD and 5.4 g of DPM and stirring.

Working Example 1-12

Aside from using 0.117 g of Aniline Derivative 4 and 0.291 g of the arylsulfonic acid compound of formula (4-1), a charge-transporting varnish was prepared in the same way as in Working Example 1-11.

Working Example 1-13

Aside from using 0.103 g of Aniline Derivative 4 and 0.306 g of the arylsulfonic acid compound of formula (4-1), a charge-transporting varnish was prepared in the same way as in Working Example 1-11.

[3] Fabrication of Organic EL Device and Evaluation of Device Characteristics

[Working Example 2-1]

The varnish obtained in Working Example 1-1 was coated onto an ITO substrate using a spin coater, then dried for 1 minute at 80° C. and subsequently baked for 15 minutes at 230° C. in an open-air atmosphere, thereby forming a uniform 30 nm thin film on the ITO substrate. A glass substrate with dimensions of 25 mm×25 mm×0.7 mm (t) and having indium-tin oxide (ITO) patterned on the surface to a film thickness of 150 nm was used as the ITO substrate. Prior to use, impurities on the surface were removed with an $O_2$ plasma cleaning system (150 W, 30 seconds).

Next, using a vapor deposition system (degree of vacuum, $1.0 \times 10^{-5}$ Pa), thin films of N,N'-di(1-naphthyl)-N,N'-diphenylbenzidine (α-NPD), tris(8-quinolinolate)aluminum (III) ($Alq_3$), lithium fluoride and aluminum were successively deposited on the ITO substrate where the thin film was formed, thereby giving an organic EL device. At this time, vapor deposition was carried out at a rate of 0.2 nm/s for α-NPD, $Alq_3$ and aluminum, and at a rate of 0.02 nm/s for lithium fluoride. The film thicknesses were set to, respectively, 30 nm, 40 nm, 0.5 nm and 100 nm.

To prevent the device characteristics from deteriorating due to the influence of oxygen, moisture and the like in air, the organic EL device was sealed with sealing substrates, following which the characteristics were evaluated (the same applies below). Sealing was carried out by the following procedure. In a nitrogen atmosphere having an oxygen concentration of not more than 2 ppm and a dew point of not more than −85° C., the organic EL device was placed between sealing substrates and the sealing substrates were laminated together using an adhesive (MORESCO Moisture Cut WB90US(P), from Moresco Corporation). At this time, a desiccant (HD-071010W-40, from Dynic Corporation) was placed, together with the organic EL device, within the sealing substrates. The laminated sealing substrates were irradiated with UV light (wavelength, 365 nm; dosage, 6,000 $mJ/cm^2$), and then annealed at 80° C. for 1 hour to cure the adhesive.

Working Examples 2-2 to 2-7

Aside from using the varnishes obtained in Working Examples 1-2 to 1-12, 1-14, 1-16, 1-18 and 1-20 to 1-24 instead of the varnish obtained in Working Example 1-1, organic EL devices were fabricated in the same way as in Working Example 2-1.

Working Example 2-8

The varnish obtained in Working Example 1-8 was coated onto an ITO substrate using a spin coater, subsequently dried for 1 minute at 80° C., and then baked for 15 minutes at 230° C. in open air, thereby forming a uniform 30 nm thin film on the ITO substrate. A glass substrate with dimensions of 25 mm×25 mm×0.7 mm (t) and having indium-tin oxide (ITO) patterned on the surface to a film thickness of 150 nm was used as the ITO substrate. Prior to use, impurities on the surface were removed with an $O_2$ plasma cleaning system (150 W, 30 seconds).

Using a vapor deposition system (degree of vacuum, $1.0 \times 10^{-5}$ Pa), a 30 nm film of α-NPD was then formed at a deposition rate of 0.2 nm/s on the ITO substrate where the thin film was formed. CBP and $Ir(PPy)_3$ were subsequently co-deposited. Co-deposition was carried out to a thickness of 40 nm while controlling the deposition rate so that the $Ir(PPy)_3$ concentration becomes 6%. Next, thin films of lithium fluoride and aluminum were successively deposited, giving an organic EL device. At this time, vapor deposition was carried out at a rate of 0.2 nm/s for aluminum and at a rate of 0.02 nm/s for lithium fluoride. The film thicknesses were set to, respectively, 0.5 nm and 100 nm.

Working Examples 2-9 to 2-13

Aside from using the varnishes obtained in, respectively, Working Examples 1-9 to 1-13 instead of the varnish obtained in Working Example 1-8, organic EL devices were fabricated in the same way as in Working Example 2-8.

The driving voltage, current density and emission efficiency when the devices fabricated in Working Examples 2-1 to 2-7 were driven at a brightness of 1,000 $cd/m^2$, the driving voltage, current density and emission efficiency when the devices fabricated in Working Examples 2-8 to 2-13 were driven at a brightness of 5,000 $cd/m^2$, and the brightness half-lives (initial brightness, 5,000 $cd/m^2$) of the devices fabricated in Working Examples 2-1, 2-2, 2-5, 2-6, 2-8 and 2-9 were measured. The results are shown in Table 6.

TABLE 6

| Example | Driving voltage (V) | Current density (mA/cm²) | Emission efficiency (cd/A) | Half-life (hours) |
|---|---|---|---|---|
| 2-1 | 5.5 | 27.7 | 3.6 | 145 |
| 2-2 | 5.9 | 27.3 | 3.7 | 197 |
| 2-3 | 5.9 | 30.4 | 3.3 | — |
| 2-4 | 5.8 | 28.1 | 3.6 | — |
| 2-5 | 5.2 | 27.4 | 3.7 | 299 |
| 2-6 | 5.2 | 27.0 | 3.7 | 294 |
| 2-7 | 6.0 | 27.5 | 3.6 | — |
| 2-8 | 9.0 | 10.6 | 28.2 | 260 |
| 2-9 | 9.0 | 10.9 | 27.6 | 257 |
| 2-10 | 9.0 | 11.0 | 27.3 | 201 |
| 2-11 | 9.4 | 11.2 | 26.8 | — |
| 2-12 | 9.3 | 11.3 | 26.5 | — |
| 2-13 | 9.3 | 11.4 | 26.3 | — |

As shown in Table 6, organic EL devices in which a charge-transporting thin film obtained from a charge-transporting varnish of the invention serves as the hole-injecting layer have an excellent durability.

The invention claimed is:

1. An aniline derivative of formula (1)

[Chemical Formula 1]

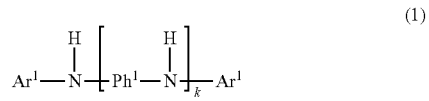

wherein Ph¹ is a group of formula (P1)

[Chemical Formula 2]

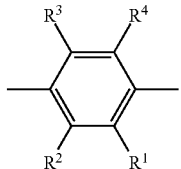
(P1)

(wherein $R^1$ to $R^4$ are each independently a hydrogen atom, a halogen atom, a nitro group, a cyano group or an alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with a halogen atom);

each $Ar^1$ is independently any moiety of formulas (A1) to (A34) below

[Chemical Formula 3]

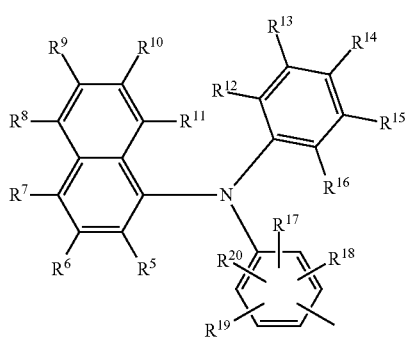
(A1)

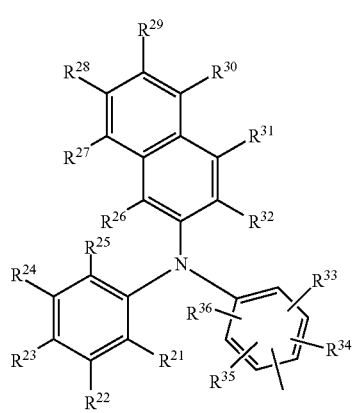
(A2)

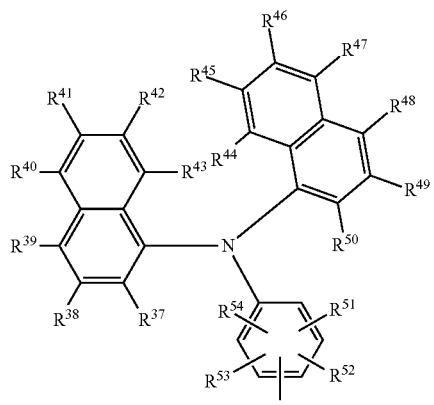
(A3)

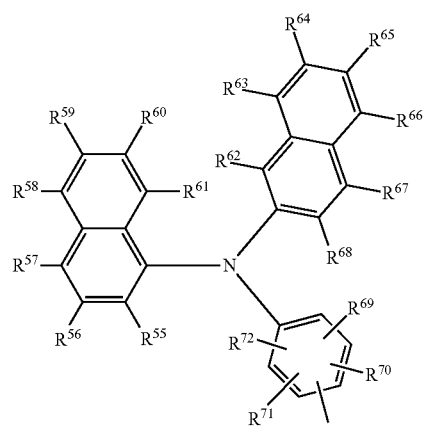
(A4)

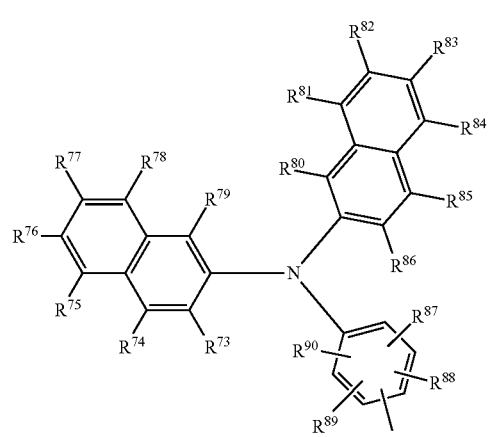
(A5)

(A6)
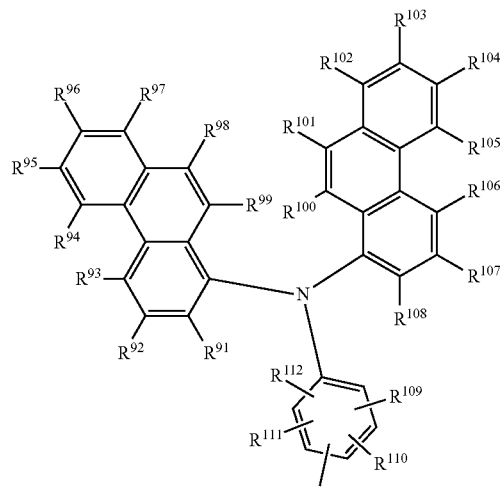
(A7)
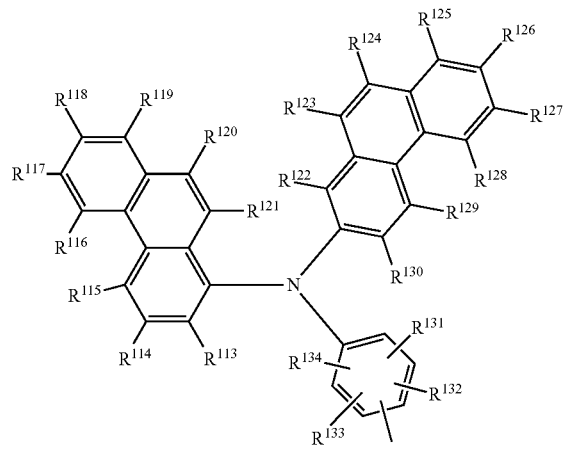
(A8)
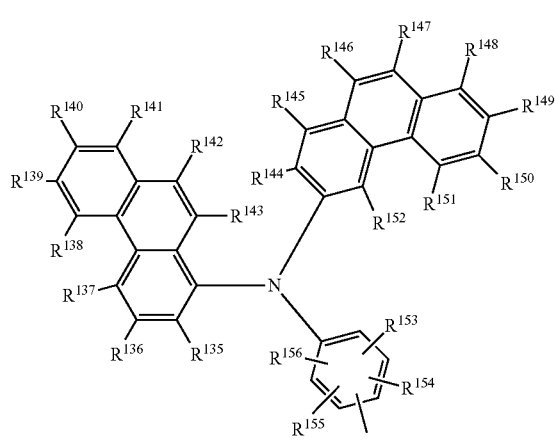
(A9)
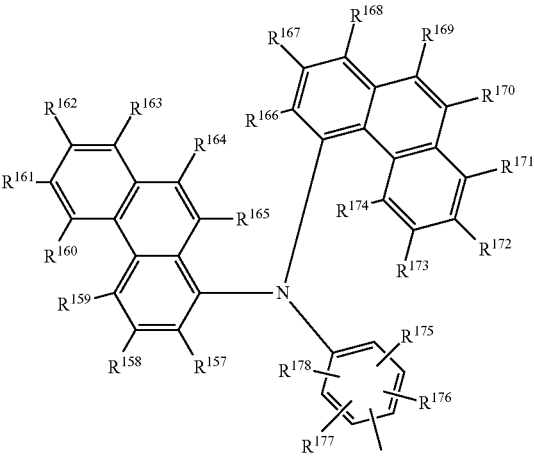
(A10)
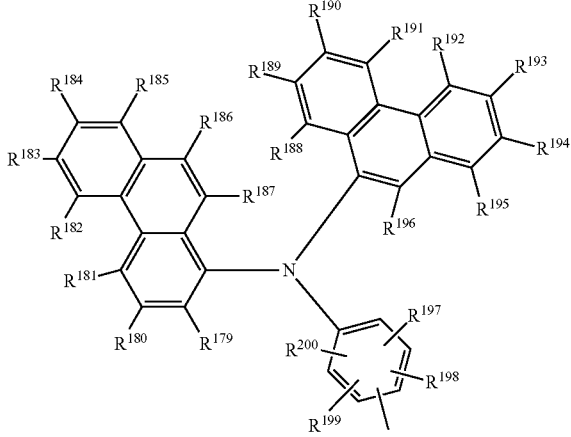
[Chemical Formula 4]
(A11)
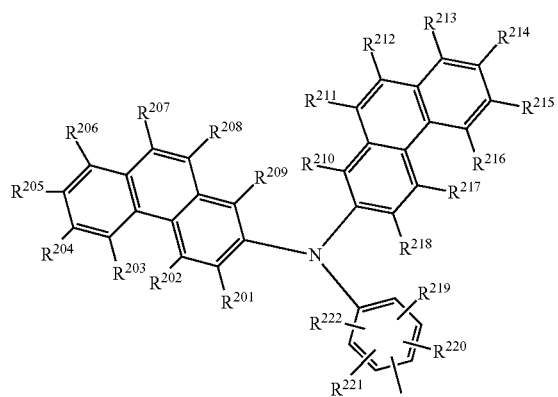

-continued
(A12)
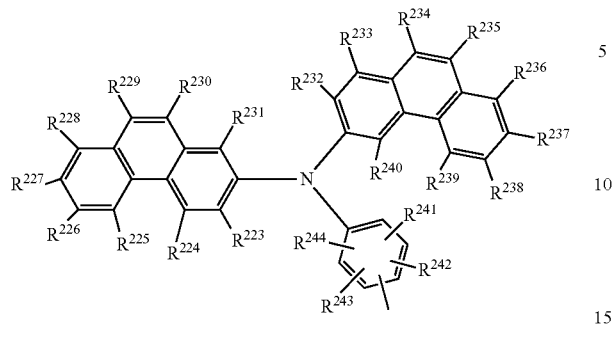
(A13)
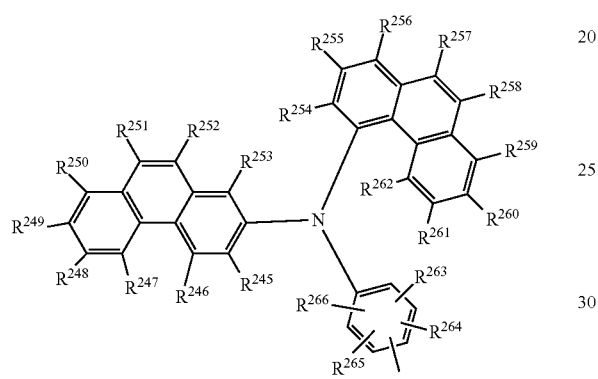
(A14)
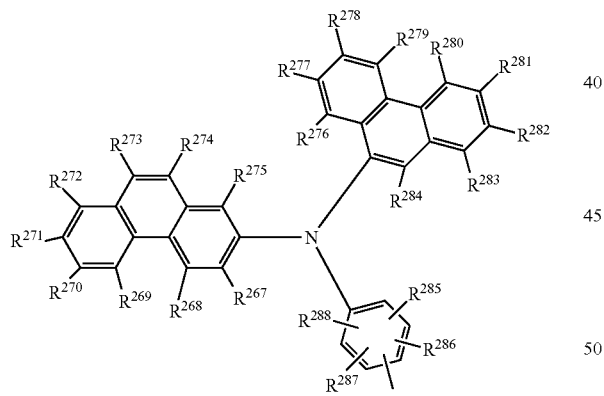
(A15)
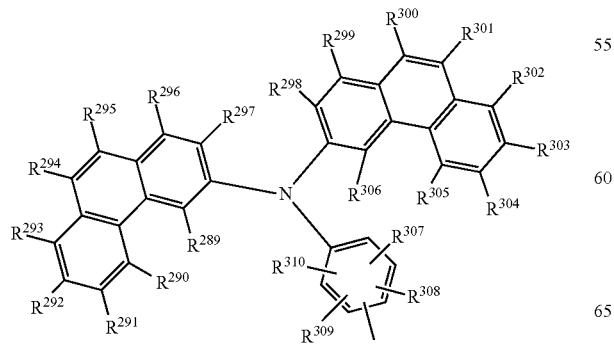
-continued
(A16)
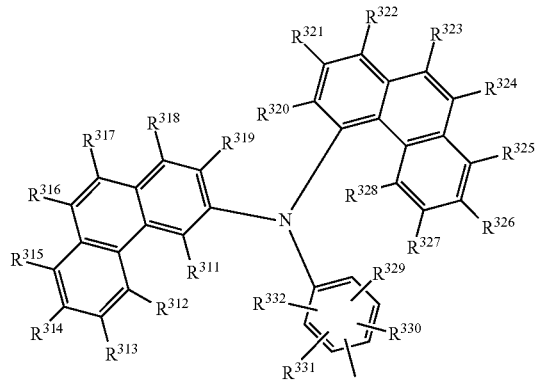
(A17)
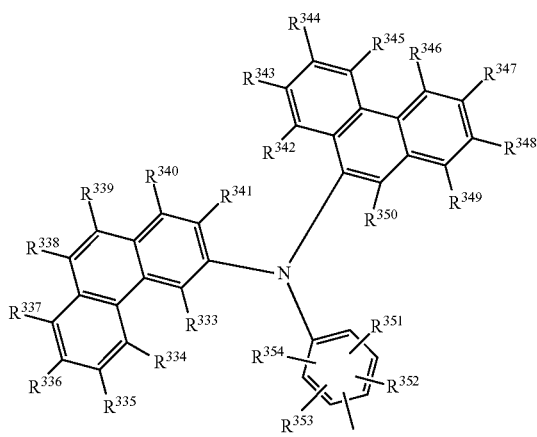
(A18)
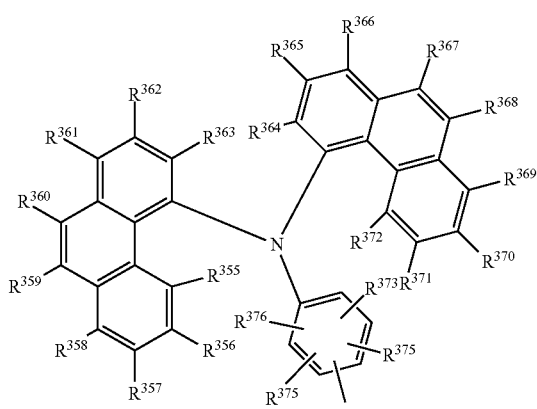

[Chemical Formula 5]
(A19)
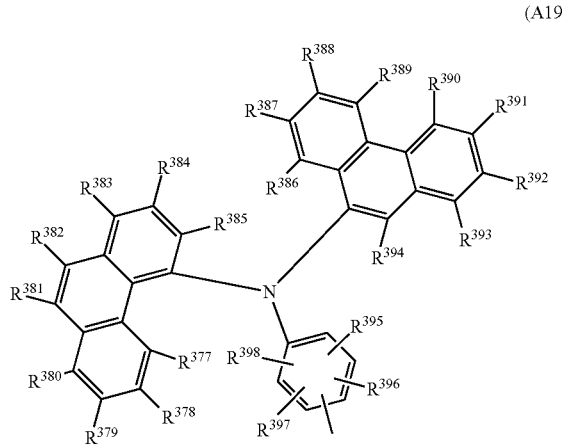
(A20)
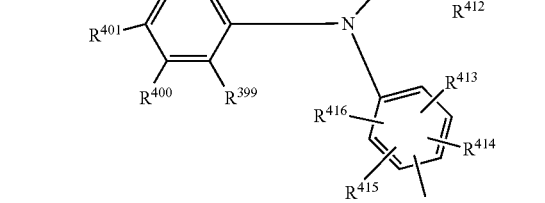
(A21)
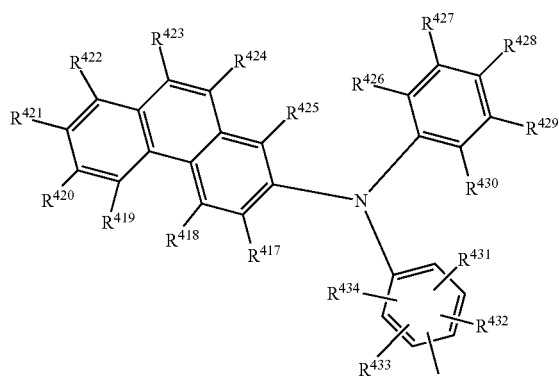
(A22)
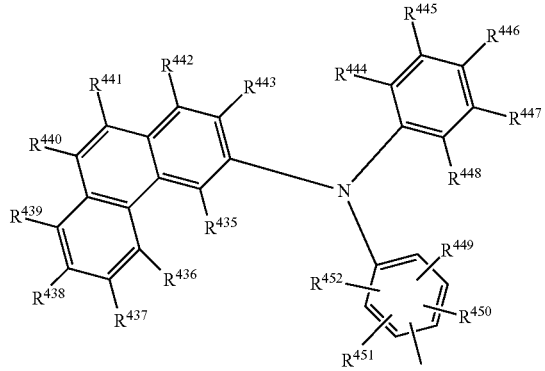
(A23)
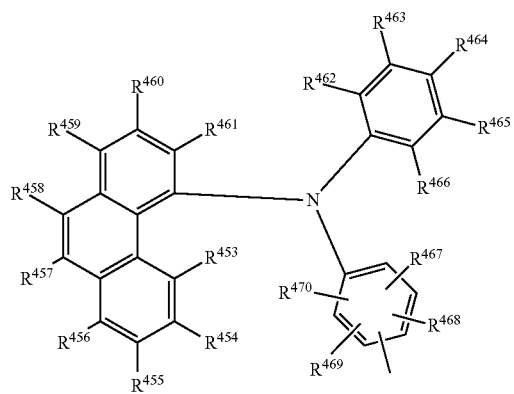
(A24)
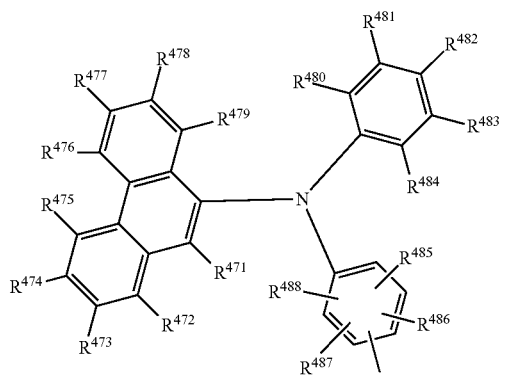
[Chemical Formula 6]
(A25)
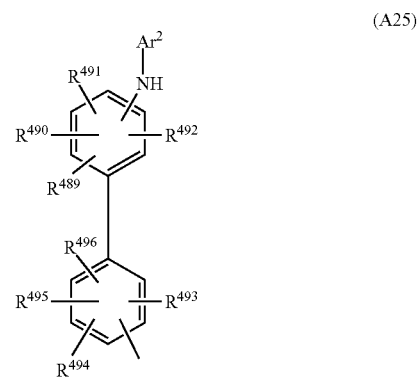

(A26) 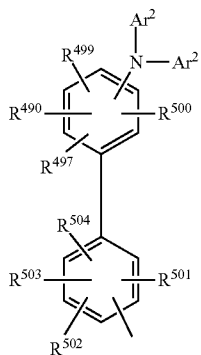

(A31) 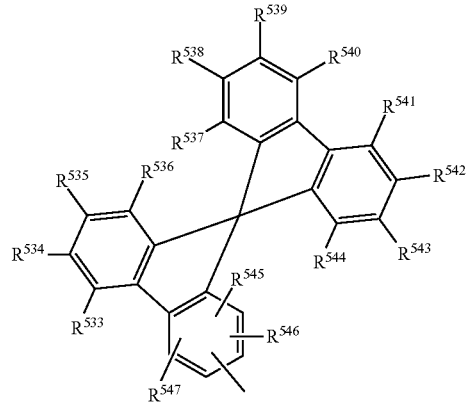

(A27) 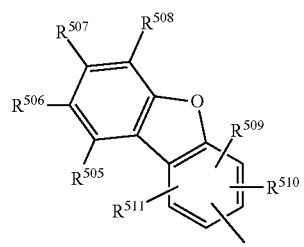

(A32) 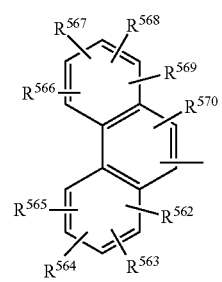

(A28) 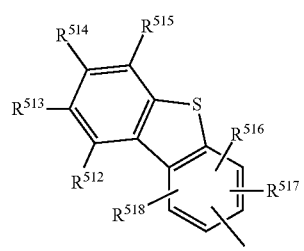

(A33) 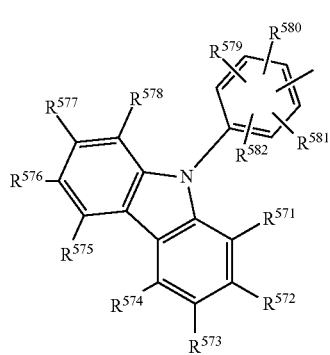

(A29) 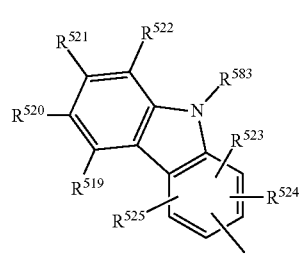

(A34)

(A30) 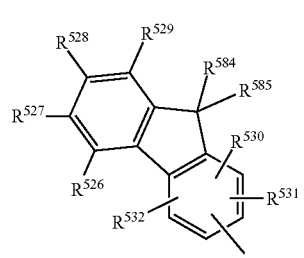

(wherein $R^5$ to $R^{582}$ are each independently a hydrogen atom, a halogen atom, a nitro group, a cyano group, or a diphenylamino group, alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with a halogen atom;

each $Ar^2$ is independently an aryl group of 6 to 20 carbon atoms which may be substituted with a di($C_{6-20}$ aryl)amino group;

$R^{583}$ is a hydrogen atom, an alkyl group of 1 to 20 carbon atoms, alkenyl group of 2 to 20 carbon atoms or alkynyl group of 2 to 20 carbon atoms which may be substituted with $Z^1$, or an aryl group of 6 to 20 carbon atoms or heteroaryl group of 2 to 20 carbon atoms which may be substituted with $Z^4$;

$R^{584}$ and $R^{585}$ are each independently an aryl group of 6 to 20 carbon atoms or a heteroaryl group of 2 to 20 carbon atoms which may be substituted with $Z^4$;

$Z^1$ is a halogen atom, a nitro group, a cyano group, or an aryl group of 6 to 20 carbon atoms or heteroaryl group of 2 to 20 carbon atoms which may be substituted with $Z^2$; $Z^2$ is a halogen atom, a nitro group, a cyano group, or an alkyl group of 1 to 20 carbon atoms, alkenyl group of 2 to 20 carbon atoms or alkynyl group of 2 to 20 carbon atoms which may be substituted with $Z^3$; $Z^3$ is a halogen atom, a nitro group or a cyano group;

$Z^4$ is a halogen atom, a nitro group, a cyano group, or an alkyl group of 1 to 20 carbon atoms, alkenyl group of 2 to 20 carbon atoms or alkynyl group of 2 to 20 carbon atoms which may be substituted with $Z^5$; and $Z^5$ is a halogen atom, a nitro group, a cyano group, or an aryl group of 6 to 20 carbon atoms or heteroaryl group of 2 to 20 carbon atoms which may be substituted with $Z^3$); and k is an integer from 2 to 10.

2. The aniline derivative of claim 1, wherein $R^1$ to $R^4$ are all hydrogen atoms.

3. The aniline derivative of claim 1 or 2, wherein $R^5$ to $R^{582}$ are all hydrogen atoms.

4. A charge-transporting substance consisting of the aniline derivative of claim 1.

5. A charge-transporting material comprising the charge-transporting substance of claim 4.

6. A charge-transporting varnish comprising the charge-transporting substance of claim 4 and an organic solvent.

7. The charge-transporting varnish of claim 6, further comprising a dopant substance.

8. The charge-transporting varnish of claim 7, wherein the dopant substance is an arylsulfonic acid compound.

9. A charge-transporting thin film produced using the charge-transporting varnish of any one of claims 6 to 8.

10. An organic electroluminescent device comprising the charge-transporting thin film of claim 9.

11. A method for producing a charge-transporting thin film, comprising the step of coating a substrate with the charge-transporting varnish of any one of claims 6 to 8 and evaporating off the solvent.

* * * * *